US012336713B2

(12) United States Patent
Shelton, IV et al.

(10) Patent No.: US 12,336,713 B2
(45) Date of Patent: Jun. 24, 2025

(54) SURGICAL STAPLES COMPRISING HARDNESS VARIATIONS FOR IMPROVED FASTENING OF TISSUES

(71) Applicant: Cilag Gmbh International, Zug (CH)

(72) Inventors: Frederick E. Shelton, IV, Hillsboro, OH (US); Jeffrey S. Swayze, West Chester, OH (US); Chester O. Baxter, III, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/764,537

(22) Filed: Jul. 5, 2024

(65) Prior Publication Data
US 2024/0358373 A1    Oct. 31, 2024

Related U.S. Application Data

(63) Continuation of application No. 17/746,488, filed on May 17, 2022, now Pat. No. 12,035,915, which is a
(Continued)

(51) Int. Cl.
A61B 17/072    (2006.01)
A61B 17/04    (2006.01)
(Continued)

(52) U.S. Cl.
CPC ........ *A61B 17/105* (2013.01); *A61B 17/0469* (2013.01); *A61B 17/064* (2013.01);
(Continued)

(58) Field of Classification Search
CPC .......... A61B 17/00491; A61B 17/0469; A61B 17/0644; A61B 17/0686; A61B 17/072;
(Continued)

(56) References Cited

U.S. PATENT DOCUMENTS 5,342,396 A    8/1994 Cook
5,403,312 A    4/1995 Yates et al.
(Continued)

FOREIGN PATENT DOCUMENTS

CN    201617885 U    11/2010
CN    103429172 A    12/2013
(Continued)

OTHER PUBLICATIONS

Brar, et al., "Investigation of the mechanical and degradation properties of Mg-Sr and Mg-Zn-Sr alloys for use as potential biodegradable implant materials," J Mech Behavior of Biomed Mat, 2012, 7:87-95, 9 pgs.
(Continued)

*Primary Examiner* — Scott A Smith
(74) *Attorney, Agent, or Firm* — Frost Brown Todd LLP

(57) ABSTRACT

A surgical staple cartridge is disclosed comprising a plurality of staples removably stored within the surgical staple cartridge. The staples comprise staple legs which extend from a staple base portion. The staple legs comprise staple tips configured to pierce tissue and contact a corresponding forming pocket of an anvil of surgical stapling instrument. The staples further comprise zones having different hardnesses.

20 Claims, 66 Drawing Sheets

Related U.S. Application Data continuation of application No. 17/022,499, filed on Sep. 16, 2020, now Pat. No. 11,510,675, which is a continuation of application No. 16/288,697, filed on Feb. 28, 2019, now Pat. No. 10,966,724, which is a continuation of application No. 14/836,411, filed on Aug. 26, 2015, now Pat. No. 10,357,251.

(51) Int. Cl.

| | |
|---|---|
| *A61B 17/064* | (2006.01) |
| *A61B 17/068* | (2006.01) |
| *A61B 17/10* | (2006.01) |
| *A61B 17/115* | (2006.01) |
| *A61B 17/32* | (2006.01) |
| *A61L 31/02* | (2006.01) |
| *A61L 31/10* | (2006.01) |
| *A61L 31/14* | (2006.01) |
| *A61B 17/00* | (2006.01) |
| *A61B 17/06* | (2006.01) |
| *A61B 17/11* | (2006.01) |
| *A61B 17/29* | (2006.01) |
| *A61B 90/00* | (2016.01) |

(52) U.S. Cl.
CPC ........ *A61B 17/0644* (2013.01); *A61B 17/068* (2013.01); *A61B 17/072* (2013.01); *A61B 17/07207* (2013.01); *A61B 17/07292* (2013.01); *A61B 17/115* (2013.01); *A61B 17/1155* (2013.01); *A61B 17/32* (2013.01); *A61L 31/022* (2013.01); *A61L 31/10* (2013.01); *A61L 31/148* (2013.01); *A61B 2017/00004* (2013.01); *A61B 2017/00398* (2013.01); *A61B 17/00491* (2013.01); *A61B 2017/00526* (2013.01); *A61B 2017/00831* (2013.01); *A61B 2017/00889* (2013.01); *A61B 2017/00893* (2013.01); *A61B 2017/00964* (2013.01); *A61B 17/0401* (2013.01); *A61B 2017/0464* (2013.01); *A61B 2017/0472* (2013.01); *A61B 2017/06042* (2013.01); *A61B 2017/0645* (2013.01); *A61B 2017/07214* (2013.01); *A61B 2017/07221* (2013.01); *A61B 2017/07228* (2013.01); *A61B 2017/07235* (2013.01); *A61B 2017/07242* (2013.01); *A61B 2017/07264* (2013.01); *A61B 2017/07271* (2013.01); *A61B 2017/07278* (2013.01); *A61B 2017/1142* (2013.01); *A61B 2017/2929* (2013.01); *A61B 2017/320052* (2013.01); *A61B 2090/037* (2016.02); *A61B 2090/038* (2016.02); *A61B 2090/08021* (2016.02)

(58) Field of Classification Search
CPC ........ A61B 17/07207; A61B 17/07292; A61B 17/105; A61B 17/115; A61B 2017/00017; A61B 2017/00022; A61B 2017/00398; A61B 2017/00473; A61B 2017/00477; A61B 2017/07214; A61B 2017/07228; A61B 2017/320052; A61B 2017/2927; A61B 2017/2943; A61B 34/30; A61B 34/71
USPC ..... 227/19, 175.1, 176.1, 180.1, 902; 606/1, 606/139, 213, 219
See application file for complete search history.

(56) References Cited

U.S. PATENT DOCUMENTS

| | | | |
|---|---|---|---|
| 6,626,916 B1 | 9/2003 | Yeung et al. | |
| 7,000,818 B2 | 2/2006 | Shelton, IV et al. | |
| 7,422,139 B2 | 9/2008 | Shelton, IV et al. | |
| 7,464,849 B2 | 12/2008 | Shelton, IV et al. | |
| 7,670,334 B2 | 3/2010 | Hueil et al. | |
| 7,721,930 B2 * | 5/2010 | McKenna | A61B 17/07207 227/176.1 |
| 7,753,245 B2 | 7/2010 | Boudreaux et al. | |
| 7,845,537 B2 | 12/2010 | Shelton, IV et al. | |
| 7,980,443 B2 | 7/2011 | Scheib et al. | |
| 8,210,411 B2 | 7/2012 | Yates et al. | |
| 8,220,688 B2 | 7/2012 | Laurent et al. | |
| 8,308,040 B2 | 11/2012 | Huang et al. | |
| 8,393,514 B2 | 3/2013 | Shelton, IV et al. | |
| 8,561,870 B2 | 10/2013 | Baxter, III et al. | |
| 8,608,045 B2 | 12/2013 | Smith et al. | |
| 8,733,613 B2 | 5/2014 | Huitema et al. | |
| 9,072,535 B2 | 7/2015 | Shelton, IV et al. | |
| 9,101,358 B2 | 8/2015 | Kerr et al. | |
| 9,345,481 B2 | 5/2016 | Hall et al. | |
| D775,336 S | 12/2016 | Shelton, IV et al. | |
| 9,549,735 B2 | 1/2017 | Shelton, IV et al. | |
| 9,585,662 B2 | 3/2017 | Shelton, IV et al. | |
| 9,642,620 B2 | 5/2017 | Baxter, III et al. | |
| 9,681,870 B2 | 6/2017 | Baxter, III et al. | |
| 9,687,232 B2 | 6/2017 | Shelton, IV et al. | |
| 9,724,092 B2 | 8/2017 | Baxter, III et al. | |
| 9,763,662 B2 | 9/2017 | Shelton, IV et al. | |
| 9,839,428 B2 | 12/2017 | Baxter, III et al. | |
| 9,968,354 B2 | 5/2018 | Shelton, IV et al. | |
| 10,028,744 B2 | 7/2018 | Shelton, IV et al. | |
| 10,098,642 B2 | 10/2018 | Baxter, III et al. | |
| 10,166,026 B2 | 1/2019 | Shelton, IV et al. | |
| 10,188,394 B2 | 1/2019 | Shelton, IV et al. | |
| 10,213,203 B2 | 2/2019 | Swayze et al. | |
| 10,265,065 B2 | 4/2019 | Shelton, IV et al. | |
| 10,357,251 B2 * | 7/2019 | Shelton, IV | A61B 17/072 |
| 10,390,829 B2 | 8/2019 | Eckert et al. | |
| 10,433,845 B2 | 10/2019 | Baxter, III et al. | |
| 10,470,769 B2 | 11/2019 | Shelton, IV et al. | |
| 10,517,599 B2 | 12/2019 | Baxter, III et al. | |
| 10,966,724 B2 * | 4/2021 | Shelton, IV | A61B 17/105 |
| 11,058,804 B2 * | 7/2021 | Widenhouse | A61B 17/07292 |
| 11,510,675 B2 * | 11/2022 | Shelton, IV | A61B 17/115 |
| 11,534,167 B2 * | 12/2022 | Diaz-Chiosa | A61B 17/0644 |
| 12,035,915 B2 * | 7/2024 | Shelton, IV | A61B 17/0644 |
| 2002/0029044 A1 | 3/2002 | Monassevitch et al. | |
| 2002/0169465 A1 | 11/2002 | Bowman et al. | |
| 2004/0254608 A1 * | 12/2004 | Huitema | A61B 17/0644 606/219 |
| 2006/0167459 A1 | 7/2006 | Groiso | |
| 2006/0235469 A1 * | 10/2006 | Viola | A61B 17/0643 606/219 |
| 2007/0175955 A1 | 8/2007 | Shelton et al. | |
| 2008/0015598 A1 | 1/2008 | Prommersberger | |
| 2008/0078800 A1 | 4/2008 | Hess et al. | |
| 2008/0082126 A1 * | 4/2008 | Murray | A61B 17/07292 606/221 |
| 2009/0001121 A1 | 1/2009 | Hess et al. | |
| 2010/0331880 A1 * | 12/2010 | Stopek | A61B 17/0644 523/118 |
| 2013/0041406 A1 * | 2/2013 | Bear | A61L 31/10 427/2.24 |
| 2013/0068815 A1 * | 3/2013 | Bruewer | A61B 17/07207 227/175.1 |
| 2014/0166726 A1 | 6/2014 | Schellin et al. | |
| 2014/0263552 A1 | 9/2014 | Hall et al. | |
| 2015/0173749 A1 | 6/2015 | Shelton, IV et al. | |
| 2015/0173756 A1 | 6/2015 | Baxter, III et al. | |
| 2015/0173789 A1 | 6/2015 | Baxter, III et al. | |
| 2017/0056000 A1 | 3/2017 | Nalagatla et al. | |
| 2017/0056002 A1 | 3/2017 | Nalagatla et al. | |
| 2017/0056005 A1 | 3/2017 | Shelton, IV et al. | |

(56) References Cited

U.S. PATENT DOCUMENTS

| | | | |
|---|---|---|---|
| 2022/0031310 A1* | 2/2022 | De La Rosa | A61B 17/0644 |
| 2022/0313264 A1 | 10/2022 | Shelton, IV et al. | |
| 2022/0370065 A1* | 11/2022 | Shelton, IV | A61B 17/07292 |

FOREIGN PATENT DOCUMENTS

| | | |
|---|---|---|
| EP | 1878391 A1 | 1/2008 |
| EP | 2060234 A1 | 5/2009 |
| EP | 2886063 A1 | 6/2015 |
| JP | H08-159124 A | 6/1996 |
| JP | H08-507708 A | 8/1996 |
| JP | 2011-041805 A | 3/2011 |
| JP | 2011-078790 A | 4/2011 |
| RU | 94014856 A | 11/1996 |
| RU | 2152756 C1 | 7/2000 |
| WO | 2012/013577 A1 | 2/2012 |

OTHER PUBLICATIONS

Erdmann, et al., "Evaluation of the soft tissue biocompatibility of MgCa0.8 and surgical steel 316L in vivo: a comparative study in rabbits," Biomed Eng OnLine, 2010, 9:63, 17 pgs.

Li, et al., "Mg-Zr-Sr alloys as biodegradable implant materials," Acta Biomaterialia, 2012, 8:3177-3188, 12 pgs.

Pellicer, et al., "On the biodegradability, mechanical behavior, and cytocompatibility of amorphous Mg72Zn23Ca5 and Crystalline Mg70Zn23Ca5Pd2 alloys as temporary implant materials," J Biomed Res, Part A, 2013, 101A:502-517, 16 pgs.

Yan, et al., "Comparison of the Effects of Mg-6Zn and Ti-3Ai-2.5V Alloys on TGF-B/TNF- a/VEGF/b-FGF in the Healing of the Intestinal Tract in vivo," Biomed Mater, 2014, 9:025011, 11 pgs.

Yan, et al., "Comparison of the Effects of Mg-6Zn and Titanium on Intestinal Tract in vivo," J Mater Sci: Mater Med, 2013, 24:1515-1525, 11 pgs.

Brazilian Search Report dated Jun. 12, 2020 for Application No. BR 112018003687-0, 4 pgs.

European Search Report and Written Opinion dated Feb. 8, 2017 for Application No. EP 16185873.3, 15 pgs.

Chinese Search Report dated Apr. 8, 2020 for Application No. CN 201680062460.4, 2 pgs.

International Search Report and Written Opinion dated Nov. 3, 2016 for Application No. PCT/US2016/046316, 19 pgs.

Japanese Office Action, Notification of Reasons for Refusal, dated Jul. 21, 2020 for Application No. JP 2018-510449, 4 pgs.

Russian Search Report dated Feb. 19, 2020 for Application No. RU 2018110061, 2 pgs.

U.S. Appl. No. 12/031,573, filed Feb. 14, 2008, entitled: "Surgical Cutting and Fastening Instrument Having RF Electrodes.".

* cited by examiner

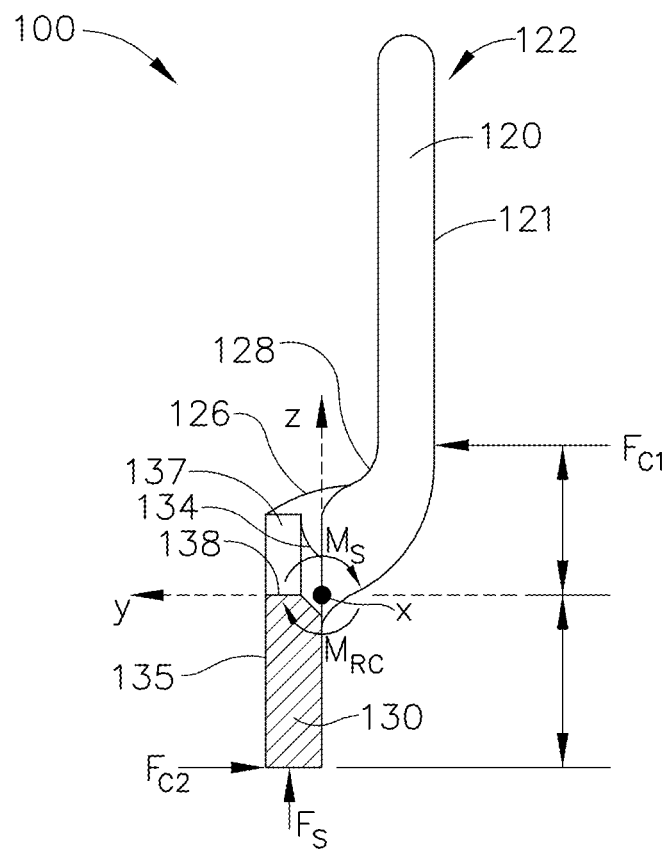
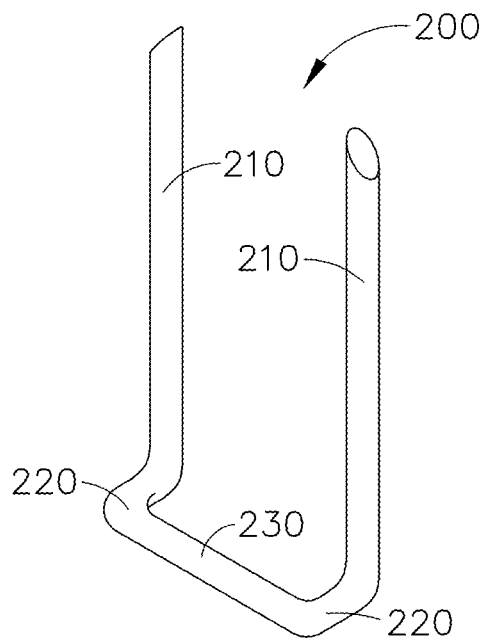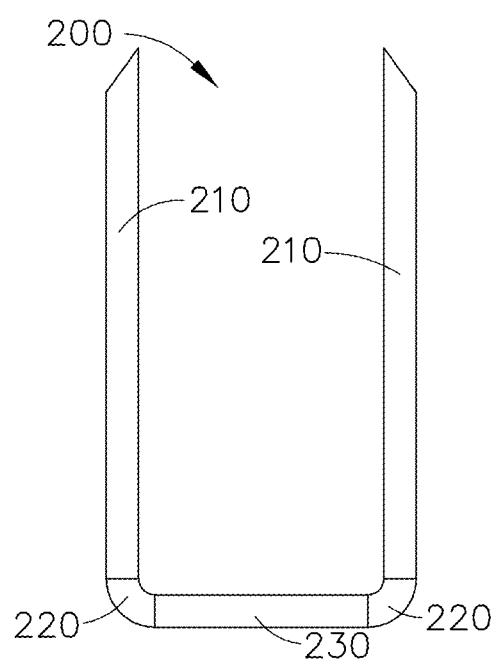
FIG. 4
FIG. 5
FIG. 6

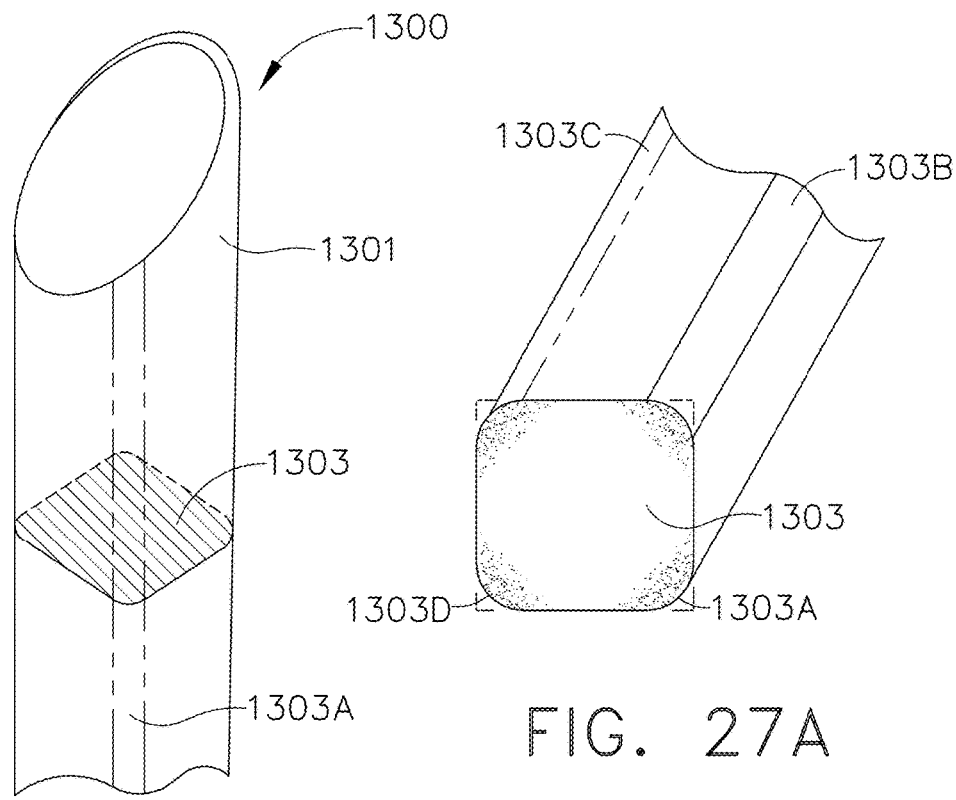
FIG. 27
FIG. 27A
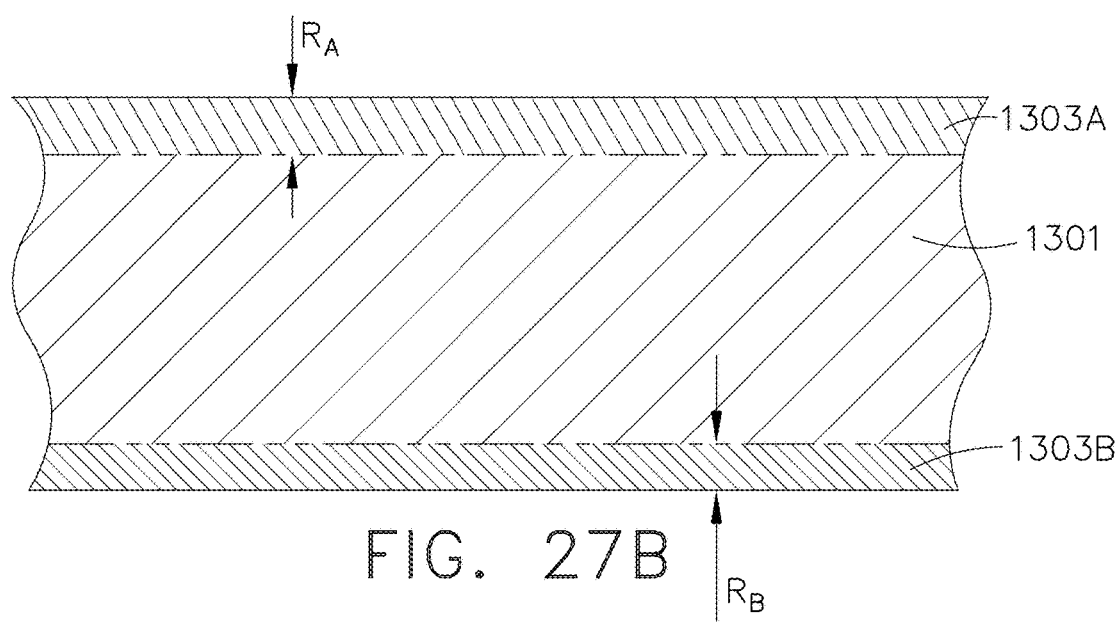
FIG. 27B

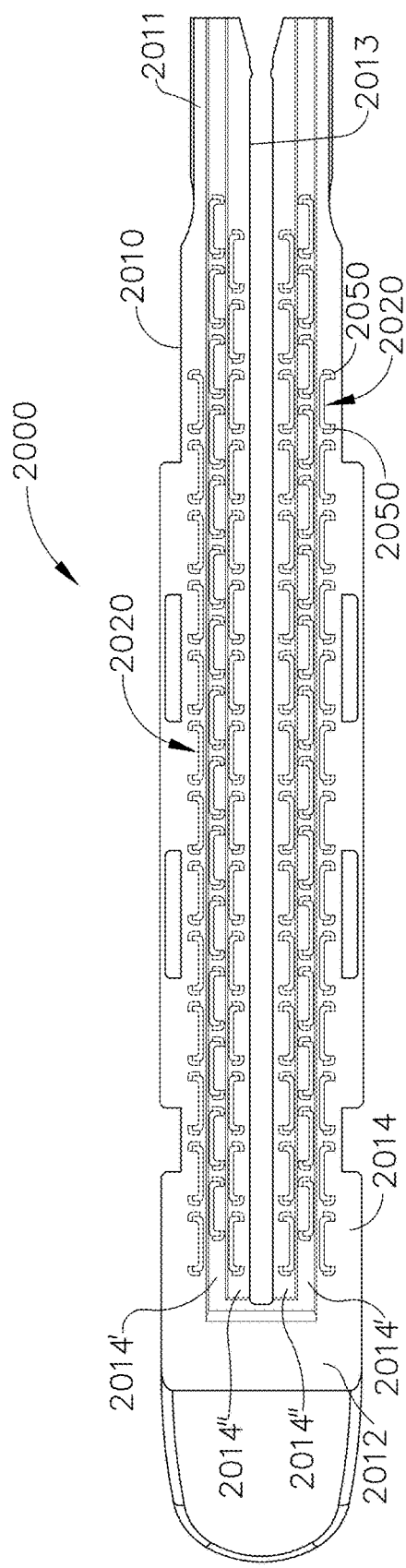
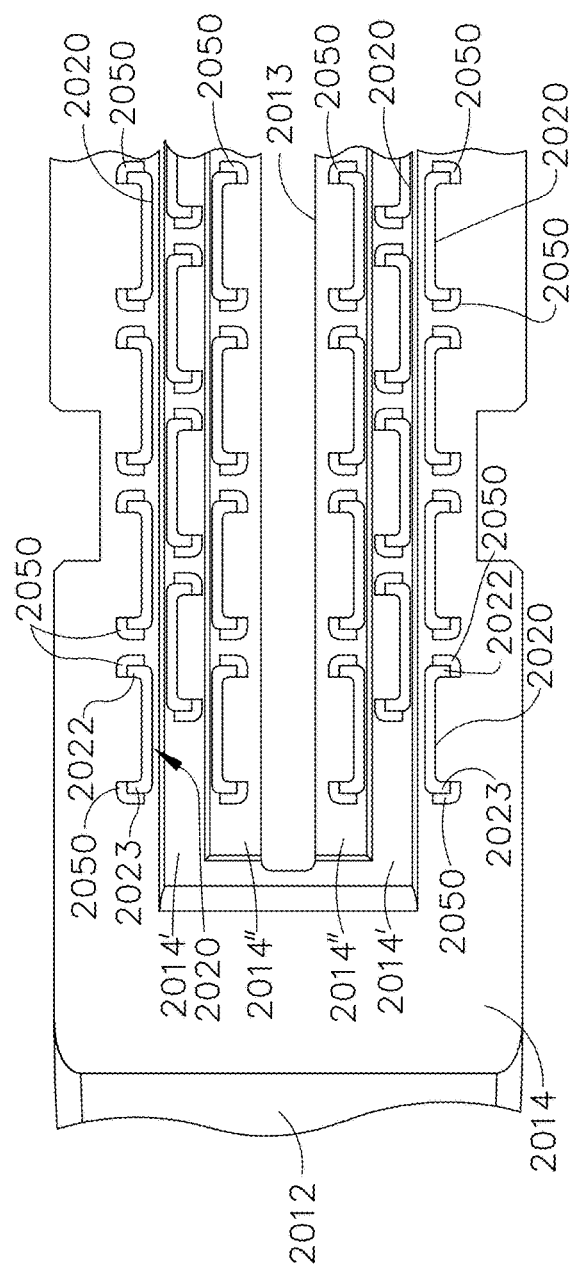
FIG. 33
FIG. 34

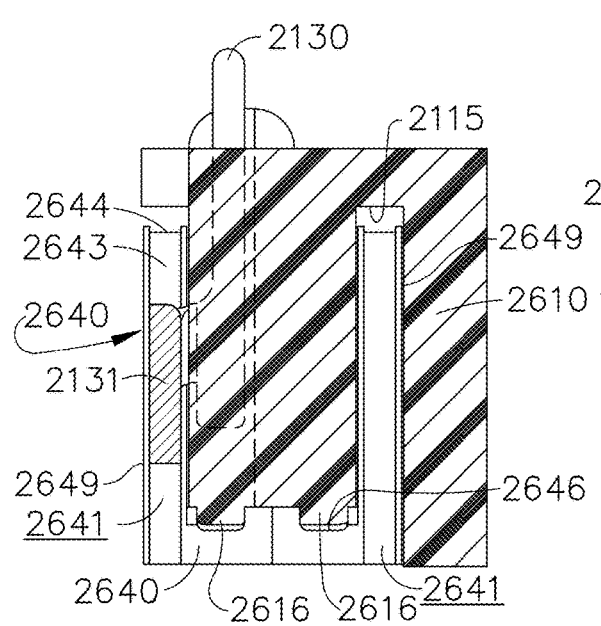
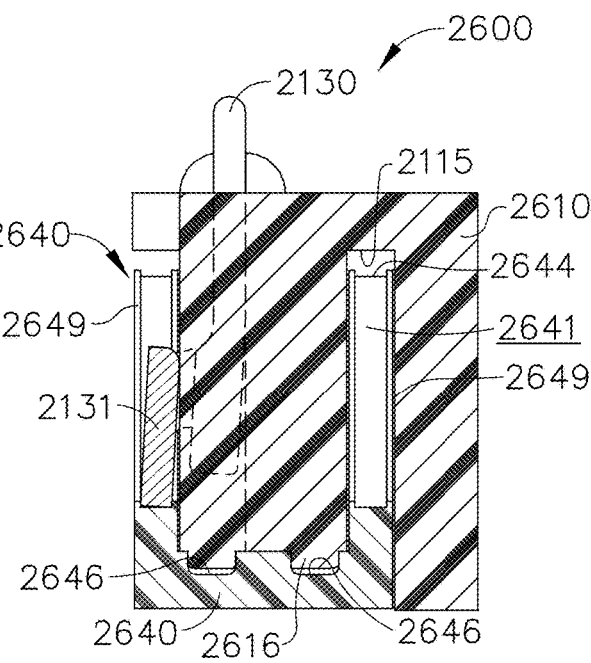
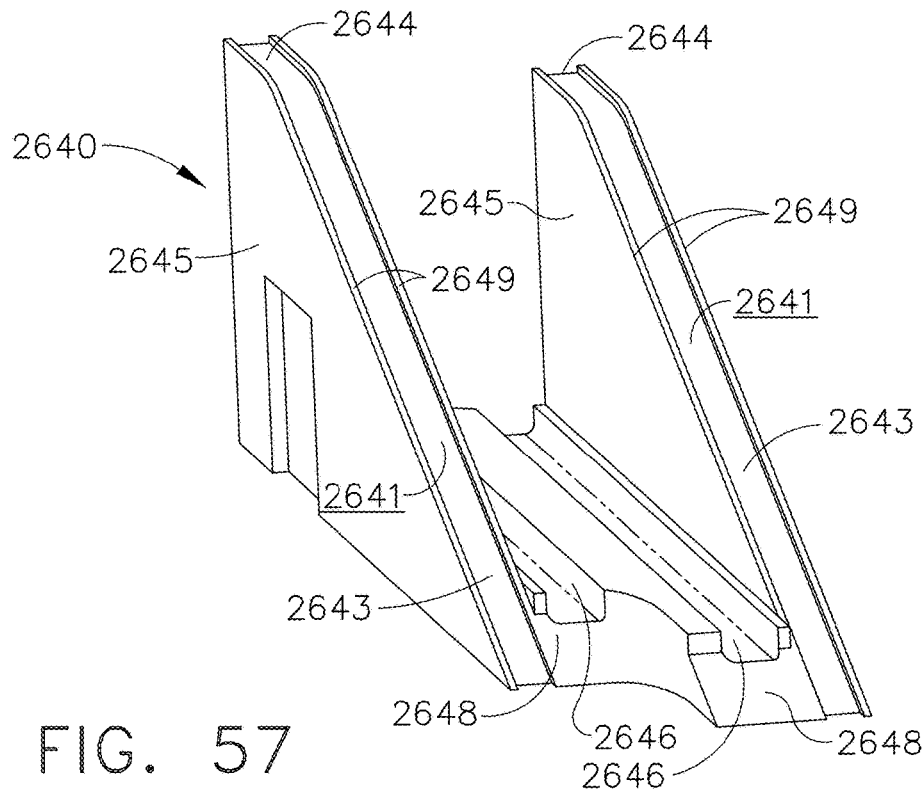

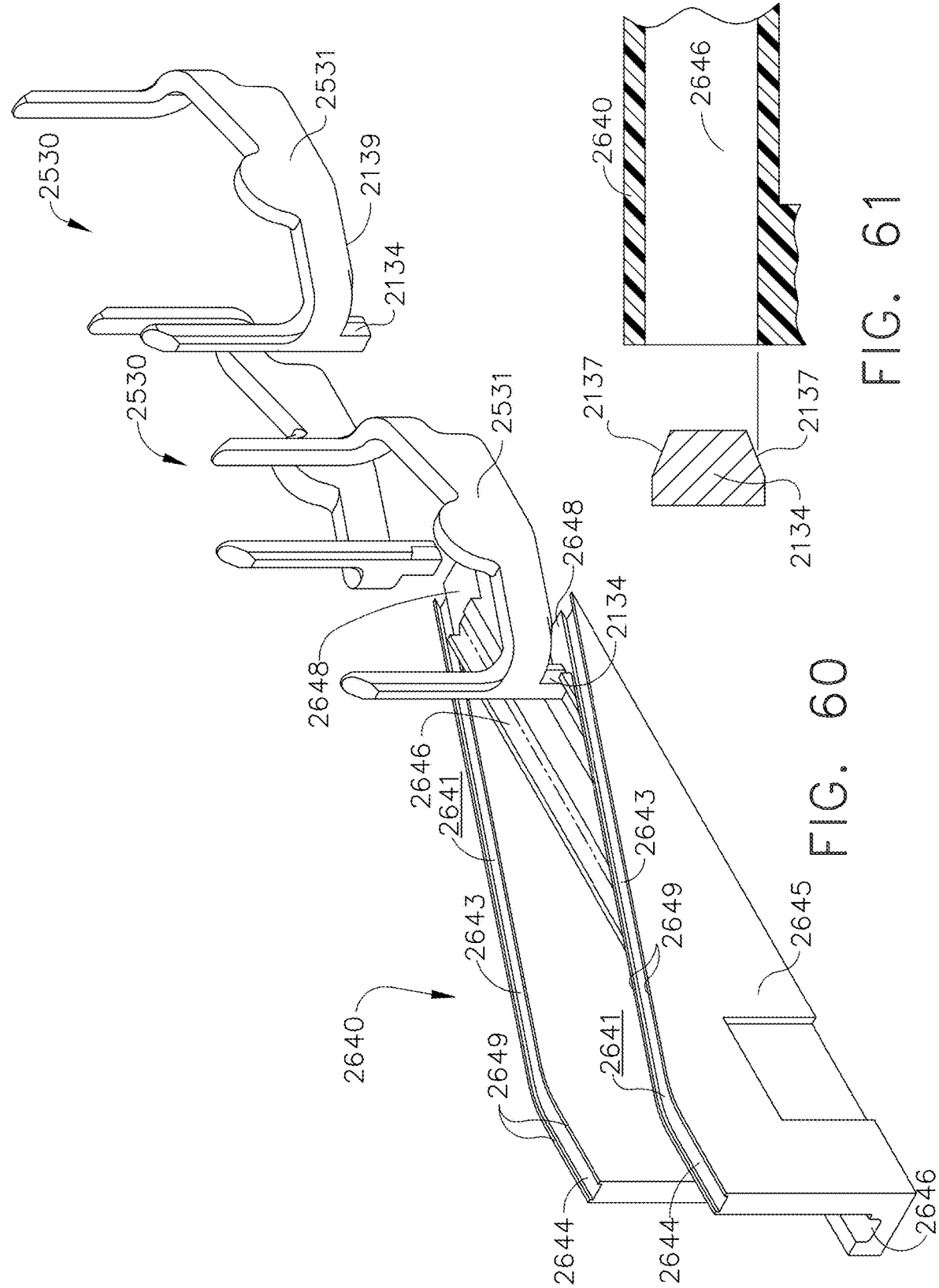

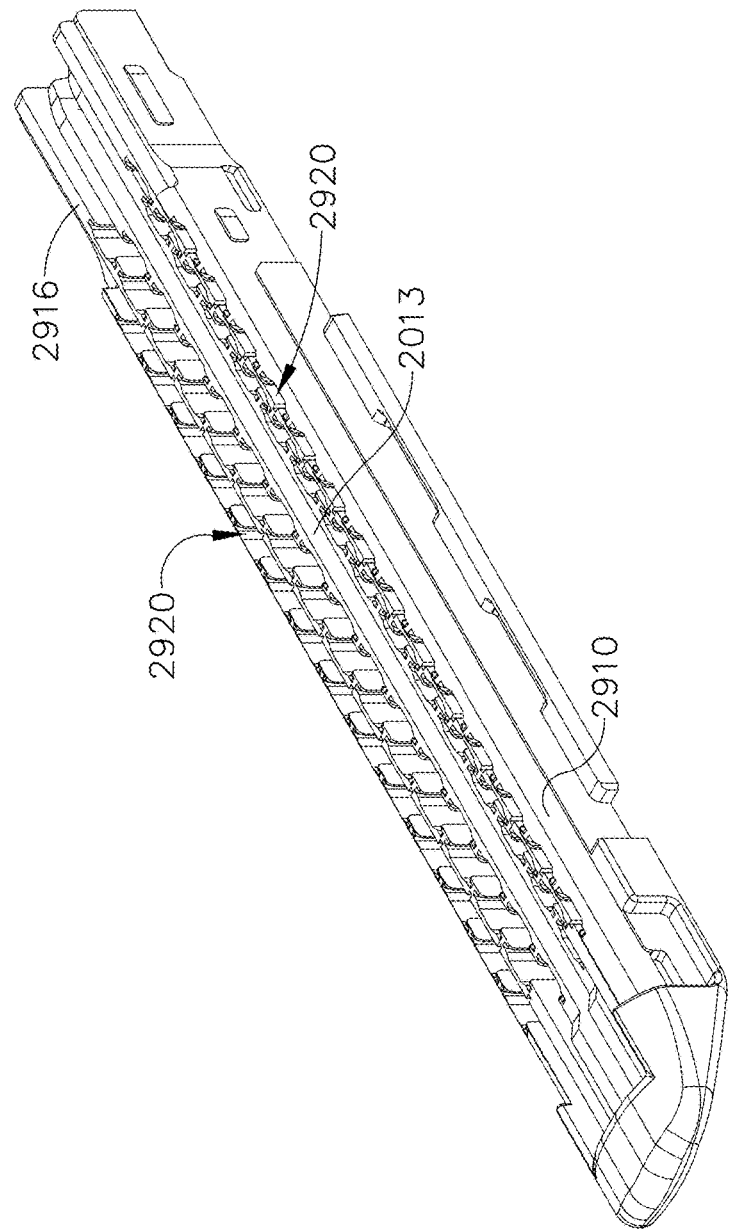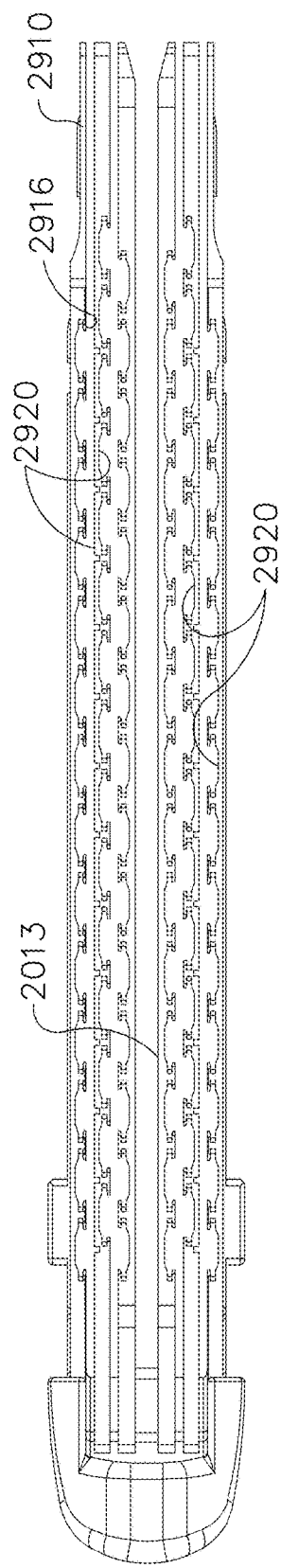

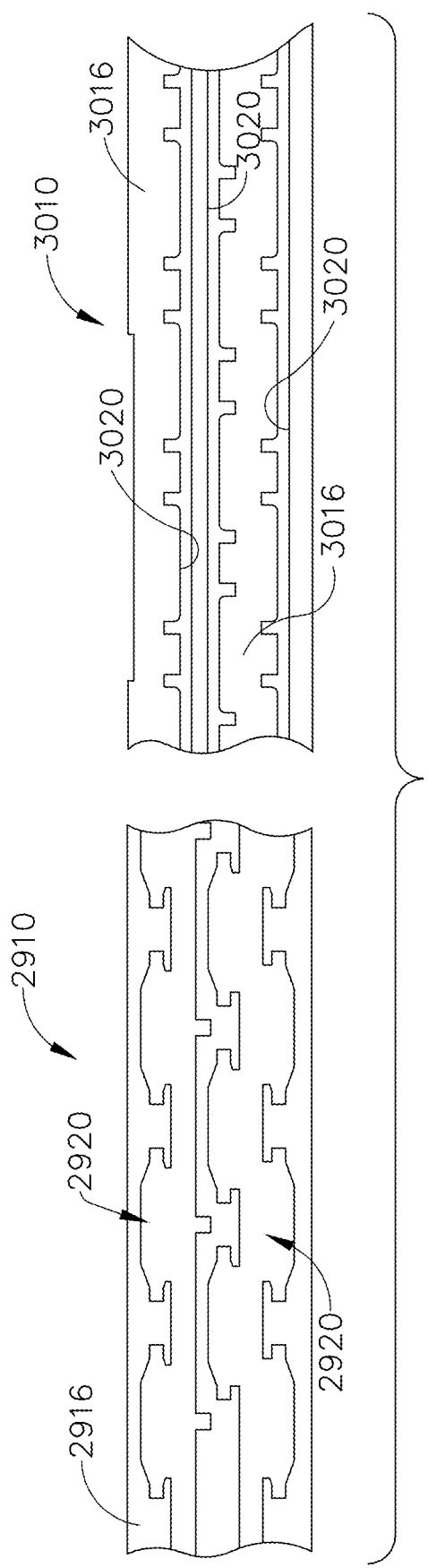
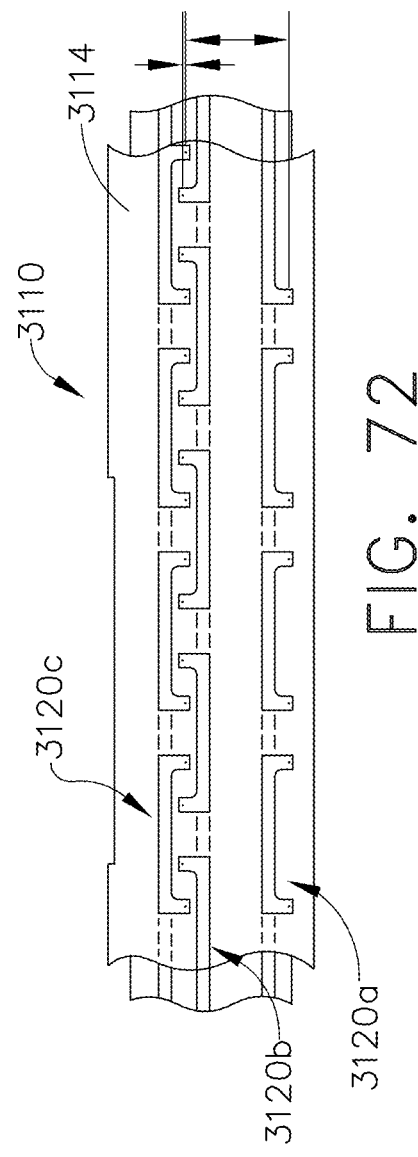
FIG. 71
FIG. 72

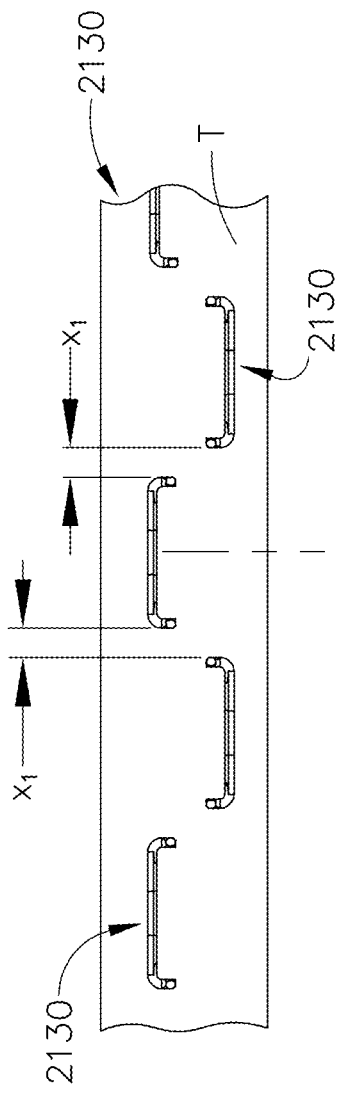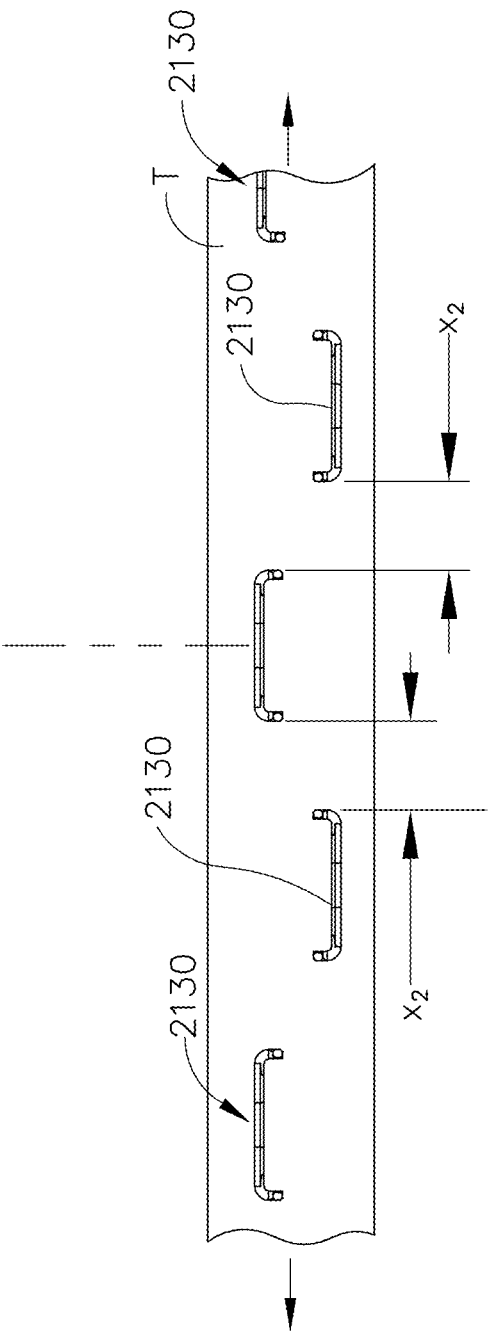

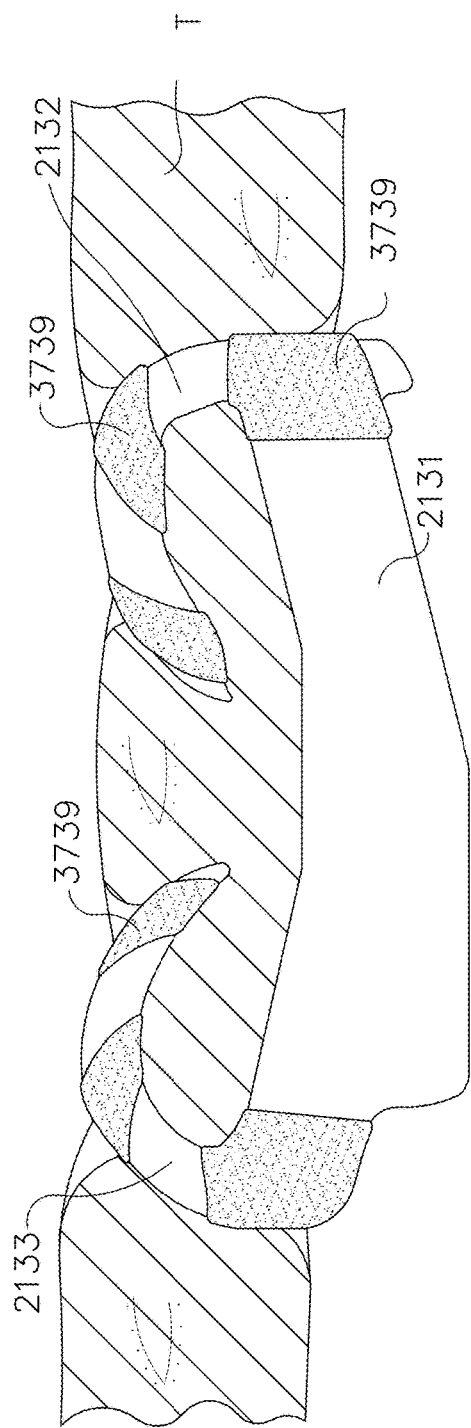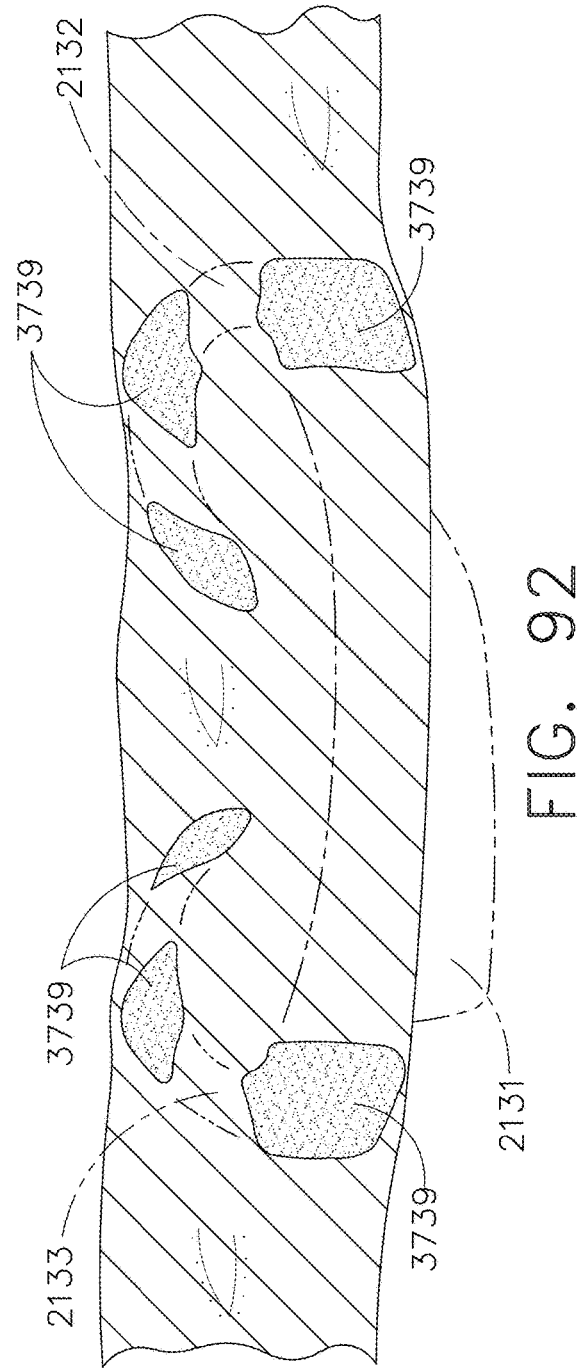

SURGICAL STAPLES COMPRISING HARDNESS VARIATIONS FOR IMPROVED FASTENING OF TISSUES

CROSS-REFERENCE TO RELATED APPLICATIONS

This application is a continuation application claiming priority under 35 U.S.C. § 120 to U.S. patent application Ser. No. 17/746,488, entitled SURGICAL STAPLES COMPRISING HARDNESS VARIATIONS FOR IMPROVED FASTENING OF TISSUE, filed May 17, 2022, issued as U.S. Pat. No. 12,035,915 on Jul. 16, 2024, which is a continuation application claiming priority under 35 U.S.C. § 120 to U.S. patent application Ser. No. 17/022,499, entitled SURGICAL STAPLES COMPRISING HARDNESS VARIATIONS FOR IMPROVED FASTENING OF TISSUE, filed Sep. 16, 2020, which issued on Nov. 29, 2022 as U.S. Pat. No. 11,510,675, which is a continuation application claiming priority under 35 U.S.C. § 120 to U.S. patent application Ser. No. 16/288,697, entitled SURGICAL STAPLES COMPRISING HARDNESS VARIATIONS FOR IMPROVED FASTENING OF TISSUE, filed Feb. 28, 2019, which issued on Apr. 6, 2021 as U.S. Pat. No. 10,966,724, which is continuation application claiming priority under 35 U.S.C. § 120 to U.S. patent application Ser. No. 14/836,411, entitled SURGICAL STAPLES COMPRISING HARDNESS VARIATIONS FOR IMPROVED FASTENING OF TISSUE, filed Aug. 26, 2015, which issued on Jul. 23, 2019 as U.S. Pat. No. 10,357,251, the entire disclosures of which are hereby incorporated by reference herein.

BACKGROUND

The present invention relates to surgical instruments and, in various embodiments, to surgical stapling and cutting instruments and staple cartridges for use therewith.

A stapling instrument can include a pair of cooperating elongate jaw members, wherein each jaw member can be adapted to be inserted into a patient and positioned relative to tissue that is to be stapled and/or incised. In various embodiments, one of the jaw members can support a staple cartridge with at least two laterally spaced rows of staples contained therein, and the other jaw member can support an anvil with staple-forming pockets aligned with the rows of staples in the staple cartridge. Generally, the stapling instrument can further include a pusher bar and a knife blade which are slidable relative to the jaw members to sequentially eject the staples from the staple cartridge via camming surfaces on the pusher bar and/or camming surfaces on a wedge sled that is pushed by the pusher bar. In at least one embodiment, the camming surfaces can be configured to activate a plurality of staple drivers carried by the cartridge and associated with the staples in order to push the staples against the anvil and form laterally spaced rows of deformed staples in the tissue gripped between the jaw members. In at least one embodiment, the knife blade can trail the camming surfaces and cut the tissue along a line between the staple rows.

The foregoing discussion is intended only to illustrate various aspects of the related art in the field of the invention at the time, and should not be taken as a disavowal of claim scope.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows:

FIG. 4 is a cross-sectional view of the staple of FIG. 1 taken along line 4-4 in FIG. 3;

FIG. 5 is a perspective view of a staple for use with a surgical stapling instrument in accordance with at least one embodiment;

FIG. 6 is a side elevation view of the staple of FIG. 5;

FIG. 27 is a partial perspective view of a staple leg in accordance with at least one embodiment;

FIG. 27A is a partial cross-sectional end view of the staple leg of FIG. 27;

FIG. 27B is a partial longitudinal cross-section of the staple leg of FIG. 27;

FIG. 33 is a top plan view of the staple cartridge assembly of FIG. 32;

FIG. 34 is a detail view of a distal end of the staple cartridge assembly of FIG. 32;

FIG. 57 is a perspective view of a firing member of a staple cartridge assembly in accordance with at least one embodiment comprising alignment channels;

FIG. 58 is a diagram illustrating the firing member of FIG. 57 and a staple positioned in a staple cavity of a staple cartridge assembly;

FIG. 59 is a diagram illustrating the firing member of FIG. 57 aligning the staple of FIG. 58 within the staple cavity of FIG. 58;

FIG. 60 is a perspective view of the firing member of FIG. 57 and staples arranged in two longitudinal rows;

FIG. 61 is a partial cross-sectional view of an alignment channel of the firing member of FIG. 57 and a portion of the staple of FIG. 58;

FIG. 67 is a bottom perspective view of a cartridge body of a staple cartridge assembly;

FIG. 68 is a bottom view of the cartridge body of FIG. 67;

FIG. 71 is a diagram illustrating the cartridge body of FIG. 67 to an alternative embodiment of a cartridge body;

FIG. 72 is a partial top plan view of a staple cartridge assembly in accordance with at least one embodiment;

FIG. 88 illustrates the spacing of the staples of FIG. 35 in unstretched tissue;

FIG. 89 illustrates the spacing of the staples of FIG. 35 in stretched tissue;

FIG. 91 illustrates the staple of FIG. 90 implanted into tissue;

FIG. 92 illustrates the staple of FIG. 90 after being partially dissolved;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
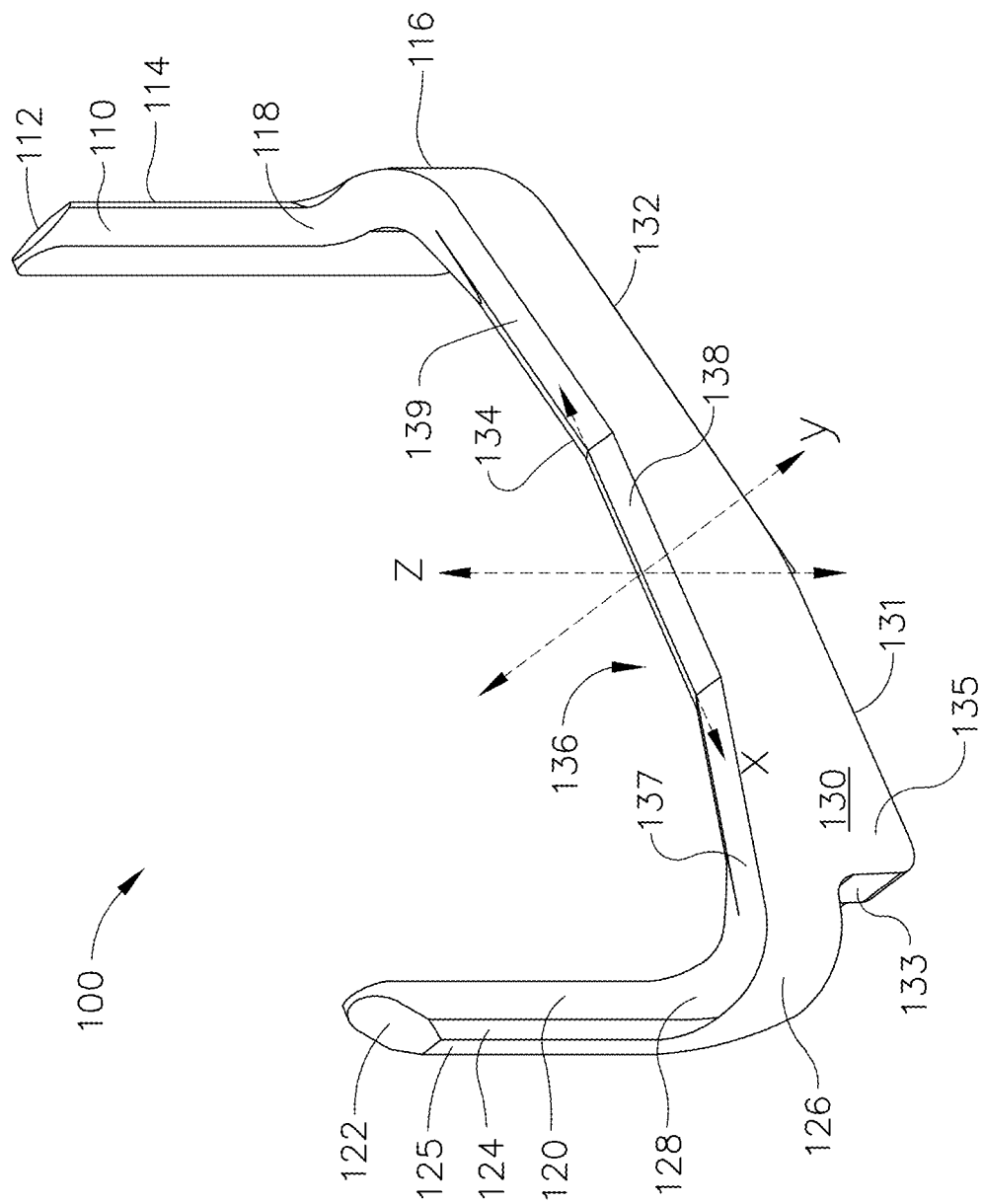
FIG. 1 is a perspective view of a staple for use with a surgical stapling instrument in accordance with at least one embodiment.

The Applicant of the present application owns the following U.S. Patent Applications that were filed on Aug. 26, 2015 and which are each herein incorporated by reference in their respective entireties:

U.S. patent application Ser. No. 14/836,324, entitled SURGICAL STAPLES FOR MINIMIZING STAPLE ROLL, now U.S. Patent Application Publication No. 2017/0056005;

U.S. patent application Ser. No. 14/836,020, entitled SURGICAL STAPLES COMPRISING FEATURES FOR IMPROVED FASTENING OF TISSUE, now U.S. Pat. No. 10,098,642;

U.S. patent application Ser. No. 14/836,058, entitled SURGICAL STAPLE STRIPS FOR PERMITTING VARYING STAPLE PROPERTIES AND ENABLING EASY CARTRIDGE LOADING, now U.S. Pat. No. 10,433,845;

U.S. patent application Ser. No. 14/836,110, entitled SURGICAL STAPLING CONFIGURATIONS FOR CURVED AND CIRCULAR STAPLING INSTRUMENTS, now U.S. Patent Application Publication No. 2017/0056000;

U.S. patent application Ser. No. 14/836,036, entitled STAPLE CARTRIDGE ASSEMBLY WITHOUT A BOTTOM COVER, now U.S. Pat. No. 10,213,203;

U.S. patent application Ser. No. 14/836,077, entitled STAPLE CARTRIDGE ASSEMBLY COMPRISING STAPLE CAVITIES FOR PROVIDING BETTER STAPLE GUIDANCE, now U.S. Pat. No. 10,517,599;

U.S. patent application Ser. No. 14/836,225, entitled STAPLE CARTRIDGE ASSEMBLY INCLUDING STAPLE GUIDES, now U.S. Pat. No. 10,028,744;

U.S. patent application Ser. No. 14/836,351, entitled STAPLE CARTRIDGE ASSEMBLY COMPRISING STAPLE ALIGNMENT FEATURES ON A FIRING MEMBER, now U.S. Pat. No. 10,470,769;

U.S. patent application Ser. No. 14/836,163, entitled STAPLE CARTRIDGE ASSEMBLY COMPRISING VARIOUS TISSUE COMPRESSION GAPS AND STAPLE FORMING GAPS, now U.S. Patent Application Publication No. 2017/0056002;

U.S. patent application Ser. No. 14/836,294, entitled STAPLES CONFIGURED TO SUPPORT AN IMPLANTABLE ADJUNCT, now U.S. Pat. No. 10,188,394;

U.S. patent application Ser. No. 14/836,375, entitled STAPLES COMPRISING A COVER, now U.S. Pat. No. 10,390,829; and U.S. patent application Ser. No. 14/836,137, entitled STAPLE CARTRIDGE ASSEMBLY INCLUDING FEATURES FOR CONTROLLING THE ROTATION OF STAPLES WHEN BEING EJECTED THEREFROM, now U.S. Pat. No. 10,166,026.

Applicant of the present application also owns the following patent applications that were filed on Dec. 23, 2013 and which are each incorporated by reference herein in their respective entireties:

U.S. patent application Ser. No. 14/138,554, entitled SURGICAL INSTRUMENTS WITH ARTICULATABLE SHAFT ARRANGEMENTS, now U.S. Patent Application Publication No. 2015/0173789;

U.S. patent application Ser. No. 14/138,465, entitled SURGICAL STAPLES AND STAPLE CARTRIDGES, now U.S. Pat. No. 10,265,065;

U.S. patent application Ser. No. 14/138,474, entitled ARTICULATABLE SURGICAL INSTRUMENTS WITH SEPARATE AND DISTINCT CLOSING AND FIRING SYSTEMS, now U.S. Pat. No. 9,681,870;

U.S. patent application Ser. No. 14/138,485 entitled SURGICAL CUTTING AND STAPLING INSTRUMENTS WITH INDEPENDENT JAW CONTROL FEATURES, now U.S. Pat. No. 9,839,428;

U.S. patent application Ser. No. 14/138,475, entitled SURGICAL STAPLES AND STAPLE CARTRIDGES, now U.S. Patent Application Publication No. 2015/0173749;

U.S. patent application Ser. No. 14/138,481, entitled SURGICAL STAPLES AND METHODS FOR MAKING THE SAME, now U.S. Pat. No. 9,968,354;

U.S. patent application Ser. No. 14/138,489 entitled SURGICAL STAPLES, STAPLE CARTRIDGES AND SURGICAL END EFFECTORS, now U.S. Pat. No. 9,687,232;

U.S. Design patent application Ser. No. 29/477,488, entitled SURGICAL FASTENER, now U.S. Design Pat. No. D775,336;

U.S. patent application Ser. No. 14/138,505 entitled FASTENER CARTRIDGE COMPRISING AN EXTENDABLE FIRING MEMBER, now U.S. Pat. No. 9,585,662;

U.S. patent application Ser. No. 14/138,518 entitled FASTENER CARTRIDGE COMPRISING A FIRING MEMBER CONFIGURED TO DIRECTLY ENGAGE AND EJECT FASTENERS FROM THE FASTENER CARTRIDGE, now U.S. Pat. No. 9,763,662;

U.S. patent application Ser. No. 14/138,530 entitled FASTENER CARTRIDGE COMPRISING A FIRING MEMBER INCLUDING FASTENER TRANSFER SURFACES, now U.S. Pat. No. 9,549,735;

U.S. patent application Ser. No. 14/138,507, entitled MODULAR SURGICAL INSTRUMENTS, now U.S. Pat. No. 9,724,092;

U.S. patent application Ser. No. 14/138,497, entitled SURGICAL CUTTING AND STAPLING INSTRUMENTS WITH ARTICULATABLE END EFFECTORS, now U.S. Pat. No. 9,642,620; and U.S. patent application Ser. No. 14/138,516, entitled SURGICAL CUTTING AND STAPLING METHODS, now U.S. Patent Application Publication No. 2015/0173756.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

A staple, or fastener, disclosed herein is configured for use with a surgical stapling instrument. Discussed in greater detail below, the staple is removably stored in a staple cavity of a staple cartridge. The staple cartridge comprises a sled configured to receive a firing actuation from the surgical stapling instrument which imparts a force on the staple to eject the staple from the staple cavity. When the staple is ejected, or driven, out of the staple cavity by the sled, the staple undergoes a deformation process where the staple forms into a fired configuration from an unfired configuration. The staple forms into the fired configuration when the staple contacts corresponding forming pockets of an anvil of the surgical stapling instrument.

Various staples disclosed herein comprise a flat-formed staple which can be cut and/or stamped from a sheet of material, for example. The sheet of material can be metallic and can comprise stainless steel and/or titanium, for example. In at least one instance, outlines can be traced, etched, and/or cut into the sheet of material which are machined and/or laser cut to form the staples into a manufactured shape.

The staples comprise a pair of staple legs and a staple base portion, or crown, from which the staple legs extend. Each staple leg comprises a staple tip, or piercing portion, which is configured to pierce the tissue and contact a corresponding forming pocket of the anvil of the surgical stapling instrument. The staple legs are configured to change shape to achieve a formed configuration to fasten the tissue. The staple base portion defines a first plane and the staple legs define a second plane which is laterally offset from but at least substantially parallel to the first plane. Embodiments are envisioned where the first and second planes are not parallel.

The flat-formed staple 100 depicted in FIGS. 1-4 comprises a proximal staple leg 110, a distal staple leg 120, and a staple base portion 130. The staple 100 further comprises vertical transition portions, or bends, 118, 128 and lateral transition portions, or bends, 116, 126. The vertical transition portions 118, 128 bend, or extend, the legs 110, 120 vertically, or upward, from the staple base portion 130. The lateral transition portions 116, 126 extend the staple legs 110, 120 laterally outward, or at least substantially perpendicularly with respect to the staple base portion 130. The staple legs 110, 120 define a first plane and the staple base portion 130 defines a second plane. Together, the vertical transition portions 118, 128 and the lateral transition portions 116, 126 permit the staple legs 110, 120 to be laterally offset and parallel with respect to the staple base portion 130. Stated another way, the first plane is offset from and at least substantially parallel to the second plane. In FIGS. 1-4, the first plane is offset in the negative Y direction. Other staples may be used in conjunction with a plurality of staples 100 where the other staples comprise a first plane which is offset in the positive Y direction. The use of both types of staples permits staple rows to be nested, or interwoven, where staple legs of neighboring rows may be at least substantially aligned and/or share a common longitudinal axis. In various instances, the staple rows can be nested to provide denser staple rows.

The proximal staple leg 110 and the distal staple leg 120 comprise staple tips 112, 122 and corners 114, 124, respectively. The tips 112, 122 are configured to pierce tissue and contact a forming pocket of an anvil of a surgical stapling instrument. The tips 112, 122 contact the anvil when the staple 100 receives a driving force to eject the staple 100 from a corresponding staple cavity in the staple cartridge. The tips 112, 122 and/or legs 110, 120 of the staple 100 will then begin forming from an unfired configuration to a fired configuration. The proximal staple leg 120 further comprises a leading engagement foot 117 comprising a chamfered surface, or edge, 119. As the sled contacts the staple 100 upon the sled's distal translation, a feature of the sled can engage the leading engagement foot 117 to aid in preventing longitudinal staple roll, or rotation, for example. The engagement foot 117 can comprise a push point that is configured to be pushed on to load the staple 100 into a staple cartridge.

Since the staple 100 is a flat-formed staple, the staple legs 110, 120, tips 112, 122, and/or other portions of the staple 100 can be further developed, or worked, after being stamped from a flat, or at least substantially flat, stock. Further developing the staple 100 can provide specific properties creating and/or altering preferential bending planes, toughness, and/or elasticity, for example. Traditional wire-formed staples comprise desirable properties advantageous for surgical fastening and can be implemented with the staple 100. Methods for constructing the corners 114, 124 and/or tips 112, 122, for example, may include any suitable process including cold working, for example. A specific process may include coining by working the corners 114, 124 into a rounded, angled, oblique, and/or parabolic profile, for example. The staple tips 112, 122 can also be worked using similar methods to provide an adequate tip configured to pierce tissue and form against a corresponding forming pocket of the anvil.

The staple base portion 130 comprises an inclined drive surface 132, a final drive surface 131, and a distal wall 133.

In various embodiments, the staple 100 is supported in a staple cartridge by a pan where the final drive surface 131 is configured to rest on the pan. In various other embodiments where a staple cartridge is pan-less, the final drive surface does not rest on a pan, rather, the final drive surface comprises an initial position residing above a bottom surface of the pan-less staple cartridge. This would allow a bottom surface of the sled and the bottom surface of the pan-less staple cartridge to be at least substantially flush as the sled translates through the cartridge. The drive surface 132 of each staple base portion 130 is configured to receive the driving force $F_s$ from the sled of the surgical stapling instrument. When the sled translates distally through the staple cartridge, the sled contacts the drive surface 132 to lift the staple 100 out of the cartridge and, in addition, contact the final drive surface 131 to form the staple 100 into its fired configuration.

The distal wall 133 acts as a distal-most wall of the staple base portion 130 and is positioned proximal of the distal staple leg 120 resulting in a lack of any portion of the staple base portion 130 underneath the distal staple leg 120. Having a greater amount of mass in the base portion 130 of the staple 100 increases the ability of the staple 100 to resist rotational motion caused by the moment $M_S$ applied by the sled. Increasing the moment of inertia of the staple base portion 130 increases the ability to resist rotational motion. As a result, a greater torque, or larger moment, would be required to cause longitudinal staple roll.

The staple base portion 130 further comprises a top surface, or compression surface, 136 comprising a proximal surface 139, an intermediate surface 138, and a distal surface 137. The proximal surface 139 is angled, or slanted, upward toward the proximal leg 110. The distal surface 137 is angled, or slanted, upward toward the distal leg 120. The intermediate surface 138 is at least substantially parallel to the final drive surface 131. This valley-like configuration limits the stress concentration of tissue captured near the transition portions 118, 128, 116, 126 where the legs 110, 120 extend from the staple base portion 130. In various embodiments, these surfaces 137, 138, 139 can be curved to create a concave surface. In traditional staples, when formed, the connections where the legs meet the staple base produce locations responsible for highly localized tissue stress. This is especially true in the event that such a traditional staple buckles, or is crushed, or flattened, rather than formed into a true "B" configuration.

Figure 2:
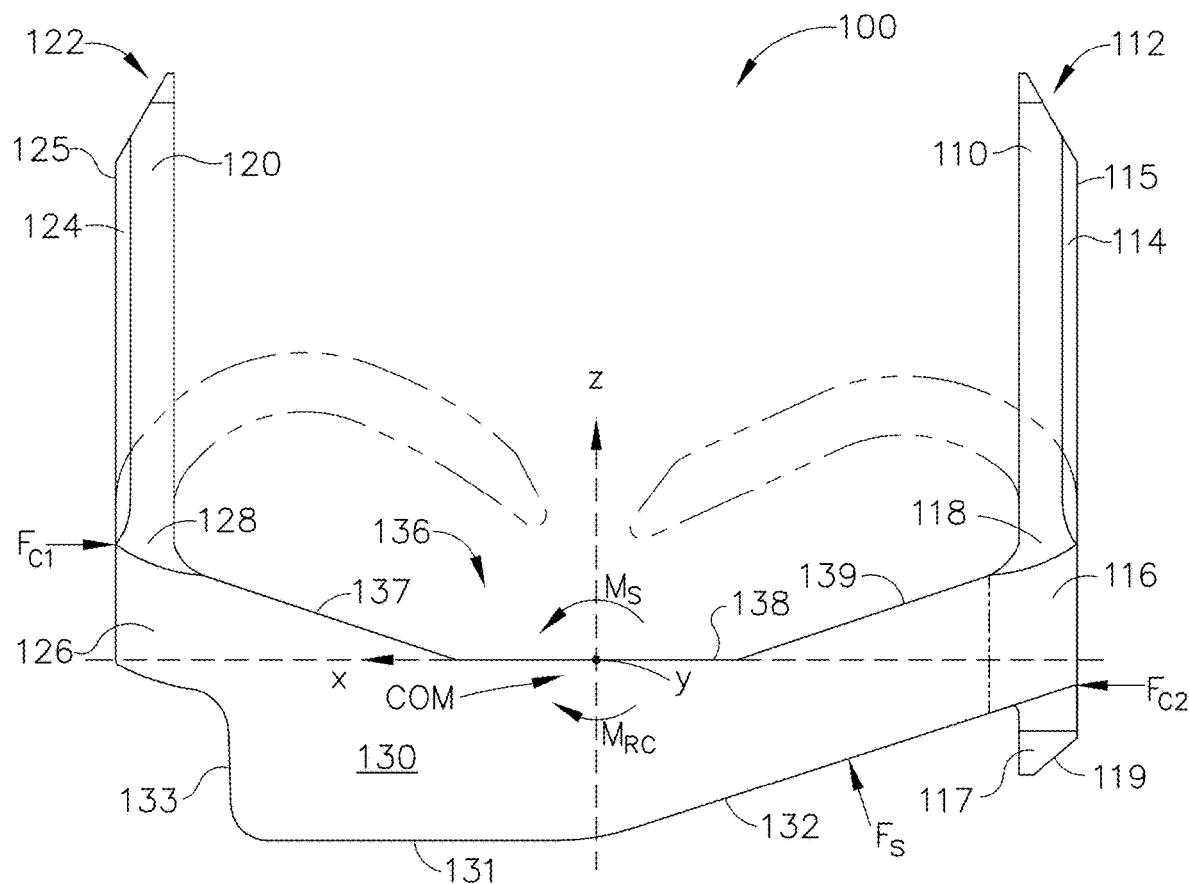
FIG. 2 is a side elevation view of the staple of FIG. 1.
Figure 3:
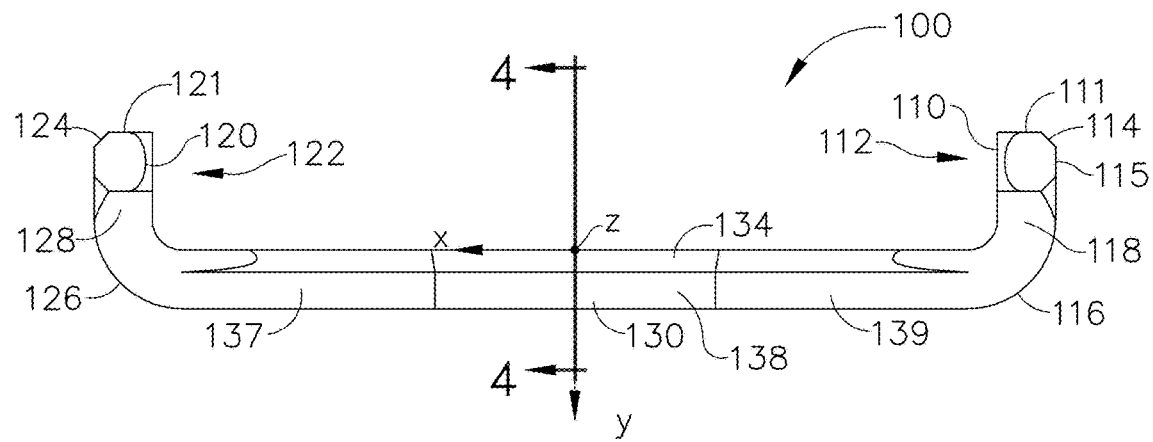
FIG. 3 is a top view of the staple of FIG. 1.
Figure 7:
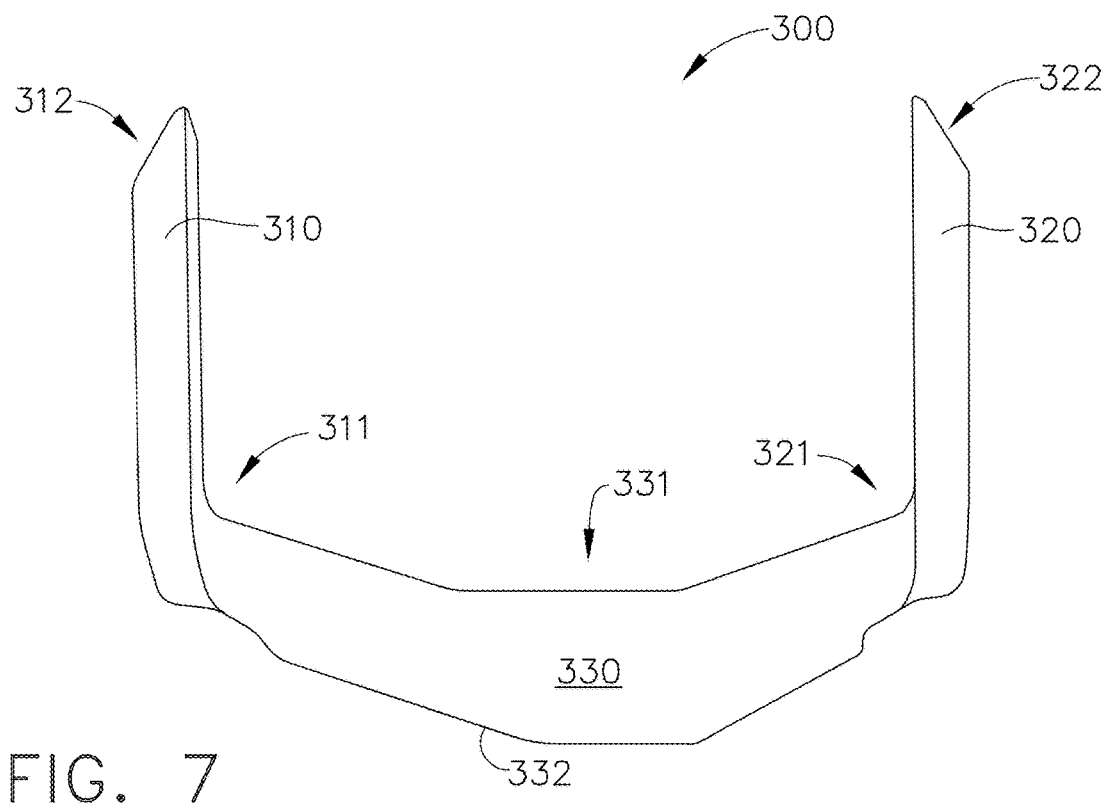
FIG. 7 is a side elevation view of a staple for use with surgical stapling instrument in accordance with at least one embodiment.
Figure 8:
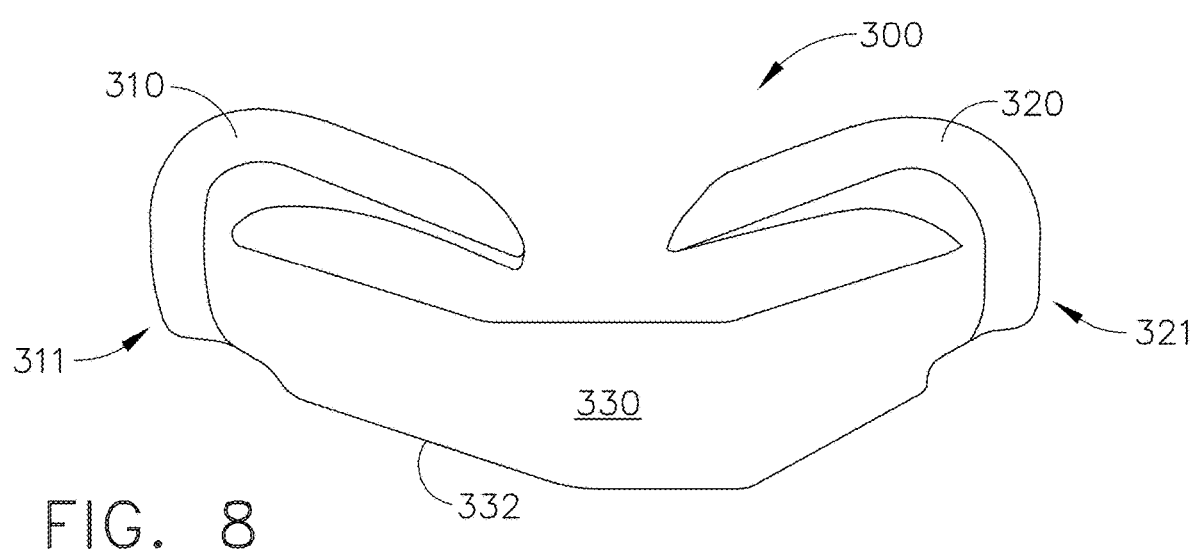
FIG. 8 is a side elevation view of the staple of FIG. 7 in a formed configuration.

In various embodiments, the dynamics of the staple 100 are predictable when ejected from a staple cartridge. As the staple 100 is ejected from its corresponding staple cavity, a driving force $F_S$ from the sled generates a moment $M_s$. One preventive measure for preventing staple roll includes increasing the moment of inertia of the staple 100, discussed above, which is configured to prevent, as illustrated in FIG. 2, longitudinal roll, or rotation of the staple. In the event that the staple 100 rolls longitudinally in the distal direction, or, in other words, rotates counterclockwise about the Y axis, outer, longitudinal staple leg surfaces 115, 125 of the staple 100 will contact the guide surfaces, or sidewalls, of the staple cartridge. This contact produces corresponding reaction forces $F_{C1}$ and $F_{C2}$. More particularly, as the staple 100 is driven out of the staple cavity and rotated about the Y axis, the wall 115 of the proximal staple leg 110 contacts a proximal sidewall of the staple cartridge producing a reaction force $F_{C2}$ which acts upon the staple leg 110 below the center of mass. The wall 125 of the distal staple leg 120 contacts a distal sidewall of the staple cartridge producing a reaction force $F_{C1}$ which acts upon the staple leg 120 above the center of mass. Both reaction forces, $F_{C1}$ and $F_{C2}$, contribute to a reactional moment $M_{RC}$ to counteract, or balance, the applied moment $M_S$ acting on the staple 100. The reaction forces discussed herein may be distributed loads acting upon a surface area of each of the staple legs 110, 120.

The moment of inertia of the staple 100 is also configured to prevent, as illustrated in FIG. 4, lateral roll, or rotation of the staple 100. The staple base portion 130 comprises a notch 134 defined in the top surface 136 on a side of the staple base portion 130 closest to the legs 110, 120. The notch 134 contributes to the predictability of the dynamics of the staple 100 before formation and upon formation when ejected from the staple cartridge. For example, referring primarily to FIG. 4, the notch 134 is configured to induce rotation of the staple 100 toward a particular cavity sidewall. In the event that the staple 100 rolls laterally, or, in other words, rotates in the direction of the applied moment $M_S$, outer, lateral staple leg walls 111, 121 of the staple 100 will contact the guide surfaces, or sidewalls, of the staple cartridge producing corresponding reaction forces $F_{C1}$ and $F_{C2}$. For example, as the staple 100 is driven out of the staple cavity and rotated in the direction of the applied moment $M_S$, the walls 111, 121 of the staple legs 110, 120 contact a corresponding sidewall of the staple cartridge producing a reaction force $F_{C1}$ which act upon the staple legs 110, 120 above the center of mass. An outer lateral wall 135 of the staple base portion 130 contacts another corresponding sidewall of the staple cartridge producing a reaction force $F_{C2}$ which acts upon the staple base portion 130 below the center of mass. Reaction forces $F_{C1}$ and $F_{C2}$ produce a reactional moment $M_{RC}$ to counteract, or balance, the applied moment $M_S$ acting on the staple 100 from the sled. The reaction forces discussed herein may be distributed loads acting upon a surface area of each of the staple legs 110, 120 and the staple base portion 130. In various embodiments, the staple 100 is encouraged to roll laterally in the direction of the applied moment $M_S$ to control which walls of the staple cavity are going to be contacted for staple guidance as the staple 100 is ejected from the staple's 100 corresponding staple cavity.

FIGS. 5 and 6 illustrate a wire-formed staple 200 comprising staple legs 210 and a staple base portion 230. The staple legs 210 are offset and bent at a substantially ninety degree angle from the staple base portion 230. The staple legs 210 reside in a first plane which is at least substantially perpendicular to a second plane defined by the staple base portion 230 and the bend portions 220 of the staple legs 210.

FIGS. 7-10 illustrate a staple 300 comprising a proximal staple leg 310, a distal staple leg 320, and a staple base portion, or crown, 330 having a drive surface 332. The staple legs 310, 320 extend from the staple base portion 330 and each staple leg 310, 320 comprises a laterally outward bend portion and an upward bend portion. The laterally outward bend portions of the staple legs bend the staple legs laterally outward with respect to the staple base portion. The upward bend portions of the staple legs bend the staple legs vertically with respect to the staple base portion. The staple 300 comprises a first zone 331 comprising a first hardness, second zones 311, 321 comprising a second hardness, and third zones 312, 322 comprising a third hardness. Embodiments are envisioned where the staple 300 comprises more or less zones than depicted. Varying certain properties, such as the hardness, of different portions of the staple 300 can provide greater control and predictability when forming the staple against corresponding forming pockets such as forming pockets 341 of anvil 340, for example. The first hardness of the first zone 331 may be greater than that of the second hardness of the second zones 311, 321. In many instances, it is desirable to have ductile staple legs 310, 320 capable of permanently changing shape without fracture or, in other words, having staple legs 310, 320 with a high plasticity, while having a staple base portion 330 that supports the staple legs 310, 320 and comprises a hardness greater than the staple legs 310, 320, for example. A greater hardness would increase the staple base portion's 330 ability to resist deformation upon the application of an external and/or internal force, such as a force from the staple legs upon being compressed against the anvil, for example.

Metal working different portions of the staples disclosed herein can comprise several advantages. One of these advantages may include being able to prevent crushing, or buckling, of the staple legs during formation and, instead, encourage the staple legs to deform in a desired configuration as a result of the contact with the corresponding forming pockets.

Figure 9:
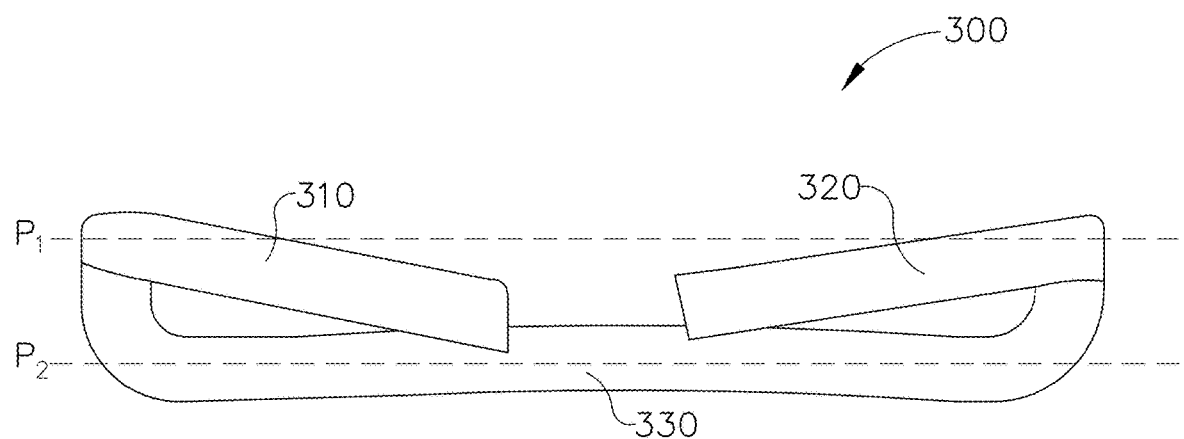
FIG. 9 is a top view of the staple of FIG. 7 in the formed configuration of FIG. 8.
Figure 10:
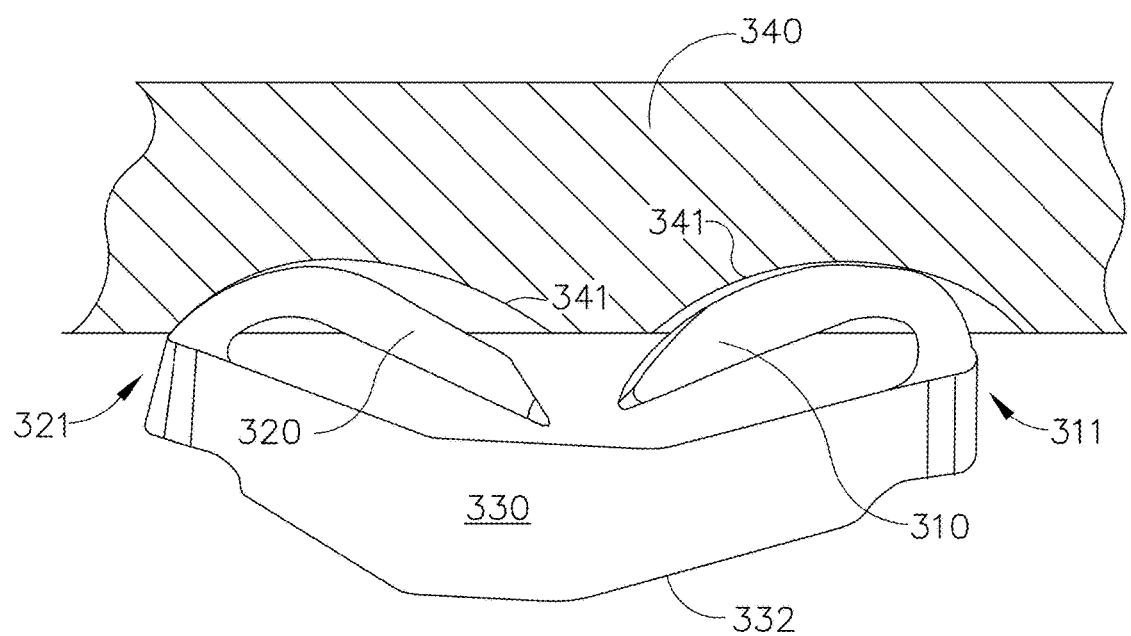
FIG. 10 is a side elevation view of the staple of FIG. 7 in a formed configuration and a partial cross-sectional view of an anvil of a surgical stapling instrument.

The staple 300 may be formed into any desired formation. In an unformed configuration, the staple legs 310, 320 define a first plane $P_1$ and the staple base portion 330 defines a second plane $P_2$. Shown in FIGS. 9 and 10 is an example of a formation of the staple 300 in which the staple legs 310, 320 are formed laterally toward the second plane $P_2$. Variations in hardness of certain zones and/or portions of the staple 300 can be responsible for providing directional encouragement when contacting the forming pockets 341. Embodiments are envisioned where the staple legs 310, 320 are formed in a direction laterally away from the second plane $P_2$.

Figure 11:
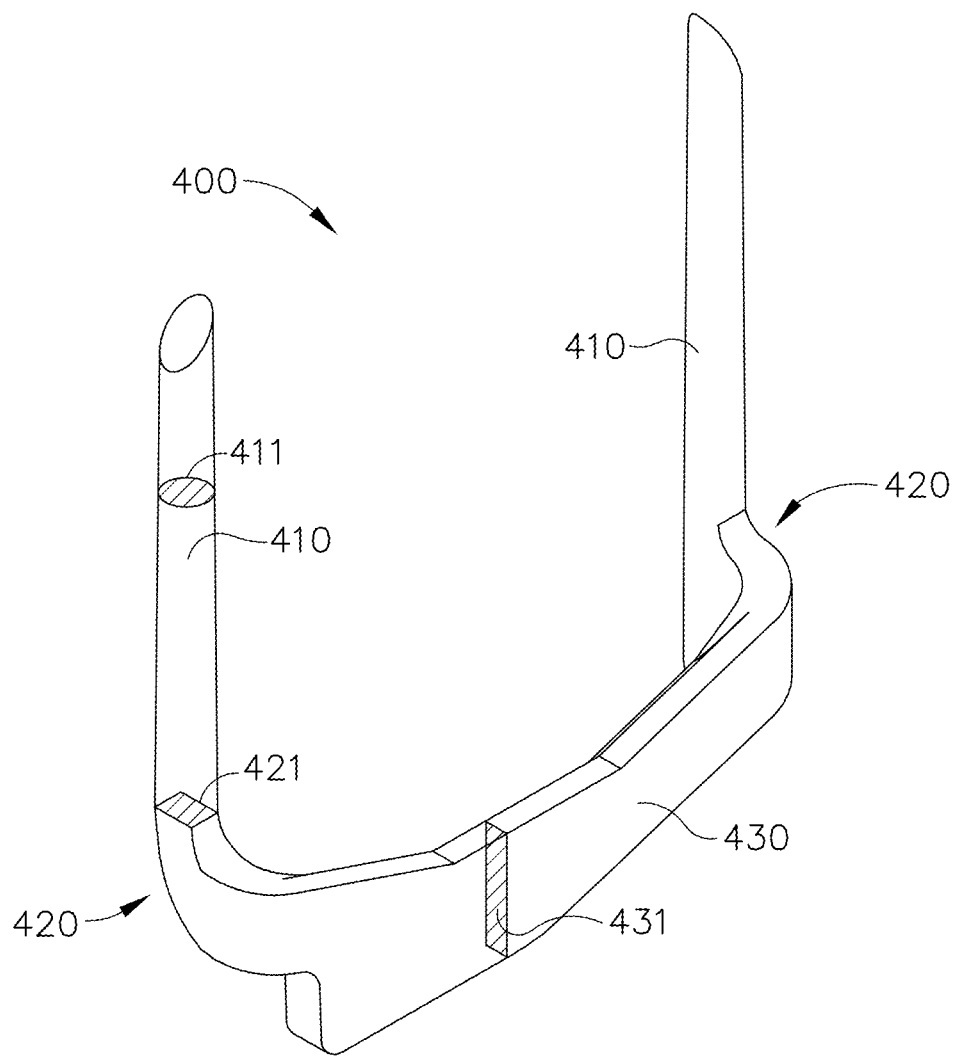
FIG. 11 is a perspective view of a staple for use with a surgical stapling instrument in accordance with at least one embodiment.
Figure 11A:
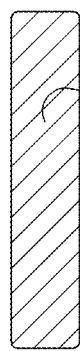
FIGS. 11A-11C are cross-sections of portions of the staple of FIG. 11.
Figure 11B:
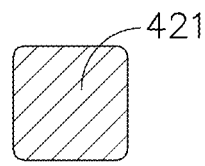
Figure 11C:
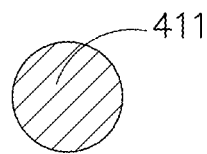

FIGS. 11-11C depict a staple 400 comprising staple legs 410 and a staple base portion 430 formed from a flat sheet of material. The staple base portion 430 comprises a rectangular cross-sectional profile 431 and the staple legs comprise a round cross-sectional profile 411. Having round staple legs 410 that extend from a staple base portion 430 having the rectangular cross-sectional profile 431 can provide a staple base portion and staple legs with no preferential bending planes. The staple 400 comprises bend portions 420 where the staple legs 410 extend from the staple base portion 430. The bend portions 420 comprise a substantially square cross-sectional profile 421. The square profile 421 and the rectangular profile 431 of the bend portions 420 and the staple base portion 430, respectively, provide a stiff connection and backbone to the round staple legs 410. The round staple legs 410 eliminate preferential bending planes that staple legs with a square, rectangular, or any shape with vertices or a non-uniform shape, cross-sections could have.

Figure 12:
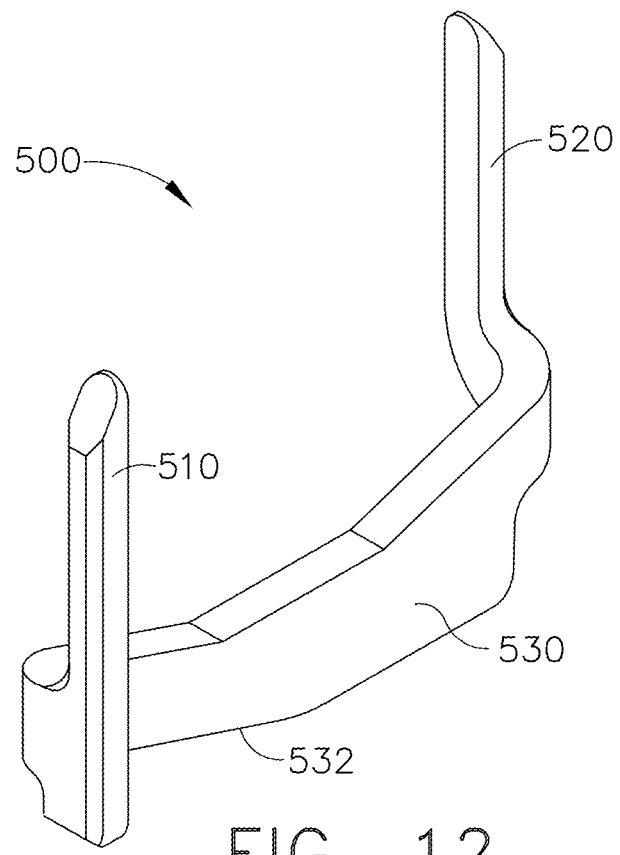
FIG. 12 is a perspective view of a staple for use with a surgical stapling instrument in accordance with at least one embodiment.

FIG. 12 depicts a staple 500 in accordance with at least one embodiment comprising a proximal staple leg 510, a distal staple leg 520, and a staple base portion 530 from which the staple legs 510, 520 extend. The proximal staple leg 510 is bent laterally outward from the staple base portion 530 in a first direction. The distal staple leg 520 is bent laterally outward from the staple base portion in a second direction. The first direction is opposite the second direction. The staple base portion 530 defines a first plane and the staple legs 510, 520 define a second plane which intersects the first plane. One advantage of having the staple legs 510, 520 bent in opposite directions can help prevent lateral roll by counteracting the applied sled moment on each side of the staple base portion 530. This results in an S-shaped configuration and requires complimentary forming pockets.

Figure 13:
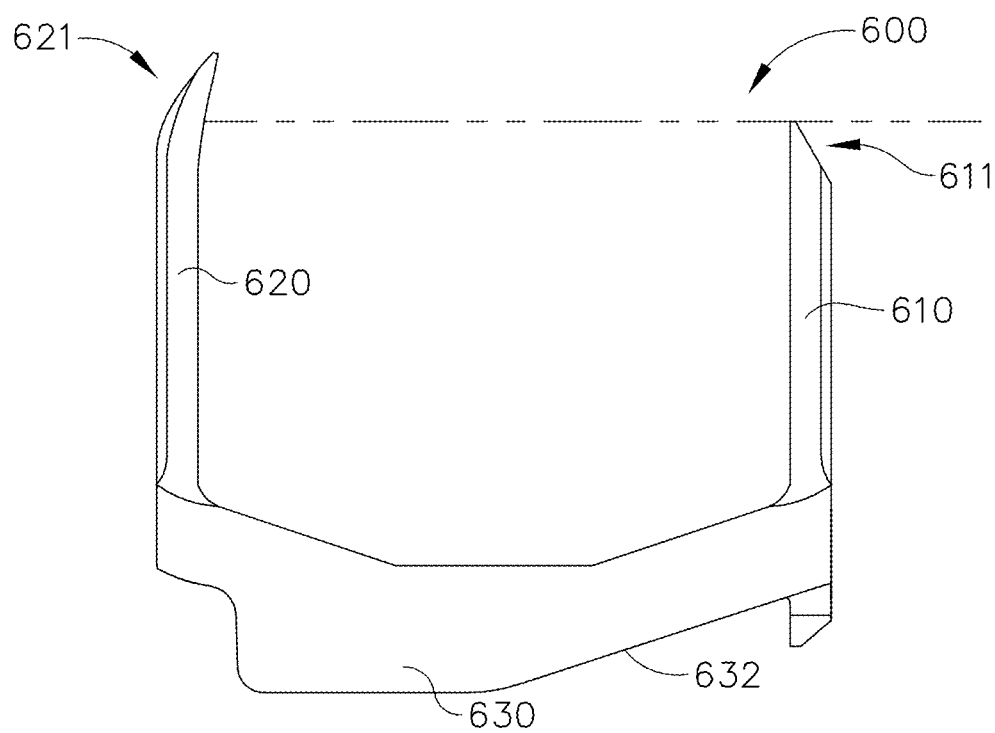
FIG. 13 is a side elevation view of a staple for use with a surgical stapling instrument in accordance with at least one embodiment.

A staple 600 is depicted in FIG. 13 comprising a proximal leg 610, a distal leg 620, and a staple base portion 630 having a drive surface 632. The distal leg 620 is longer than the proximal leg 610 resulting in an offset contact timing of the tips 611, 621 of the staple legs 610, 620 against the forming pockets of the anvil. In various embodiments, the distal leg may comprise a tip that comprises an initial pre-bent configuration to aid in the forming process when initially contacting the anvil. This pre-formed tip 621 would require less compressive force than the staple tip 611 to begin deformation against the anvil. Having the longer staple leg, in this case the distal staple leg 620, contact the anvil before the shorter, or proximal, staple leg, 610 may require the staple tip 621 of the longer leg 620 to have, to a certain degree, a pre-formed tip before the tip 611 is deformed.

Figure 14:
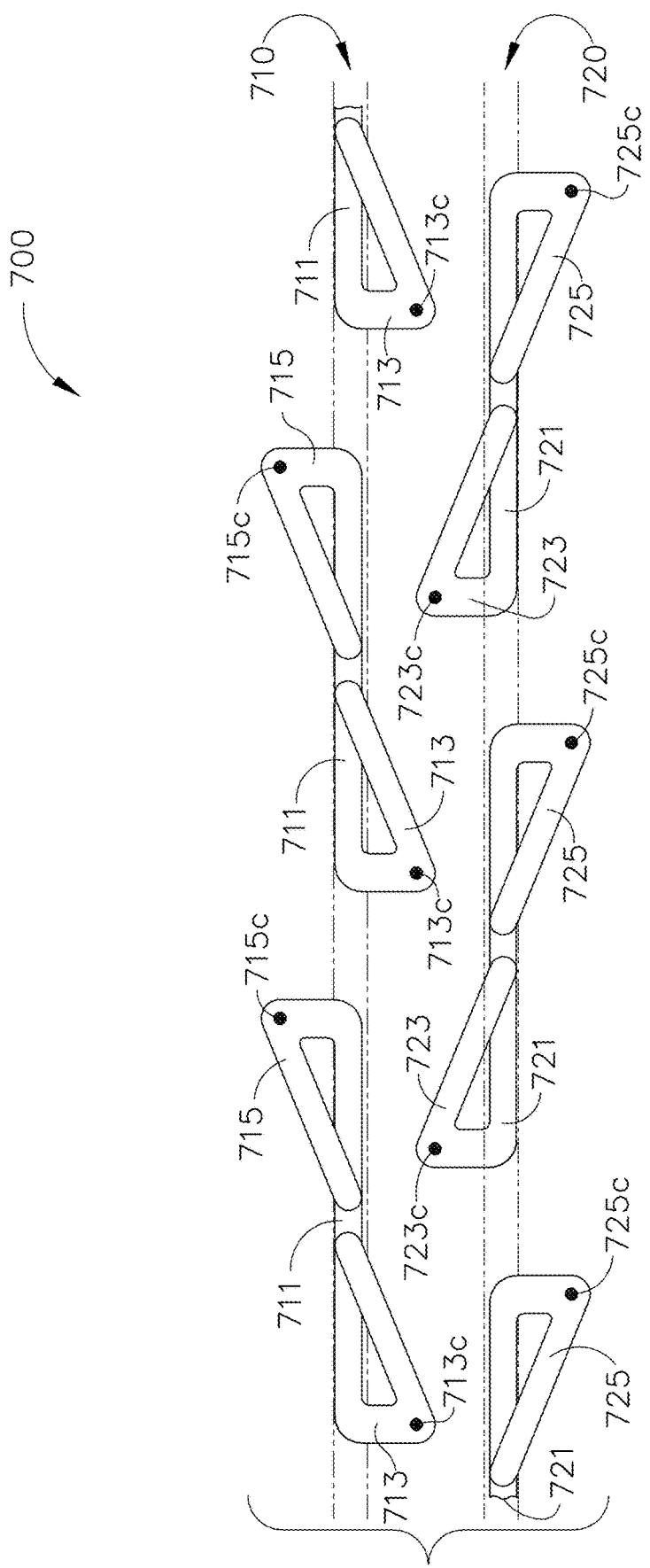
FIG. 14 is a partial top view of a formed staple configuration comprising a plurality of staples in accordance with at least one embodiment.

FIG. 14 illustrates an arrangement 700 of formed staples 711, 721. The staples 711 are arranged in a first row 710 and the staples 721 are arranged in a second row 720 which is adjacent to the first row 710. The staples 711, 712 may be similar to that of the staple 600 illustrated in FIG. 13 discussed above. The staples 711 comprise laterally opposing legs 713, 715. The staples 721 comprise laterally opposing legs 723, 725. The laterally opposing legs 713, 715 each comprise tips configured to contact forming pockets of an anvil at contact points 713c, 715c, respectively. The laterally opposing legs 723, 725 also each comprise tips configured to contact forming pockets of an anvil at contact points 723c, 725c, respectively. The laterally opposing legs 713, 715 each form inwardly toward the staple base portion from which they extend. The laterally opposing legs 723, 725 also each form inwardly toward the staple base portion from which they extend.

The staple rows 710, 720 are interwoven such that the contact points 723c, 713c are in substantial alignment. Such an arrangement allows for a more densely arranged staple row configuration in a staple cartridge and/or a more densely arranged forming pocket configuration on an anvil. Also, intersecting purchase planes may provide for a higher quality purchase and a larger area of purchase coverage in the tissue. The intersecting purchase planes may guarantee that anything captured between the staple rows and the forming pockets is guaranteed to be adequately fastened. This can help when stapling smaller vessels and/or not easily visible vessels that, in conventional staple arrangements, may navigate staple row separations resulting in less than adequate fastening.

Figure 15:
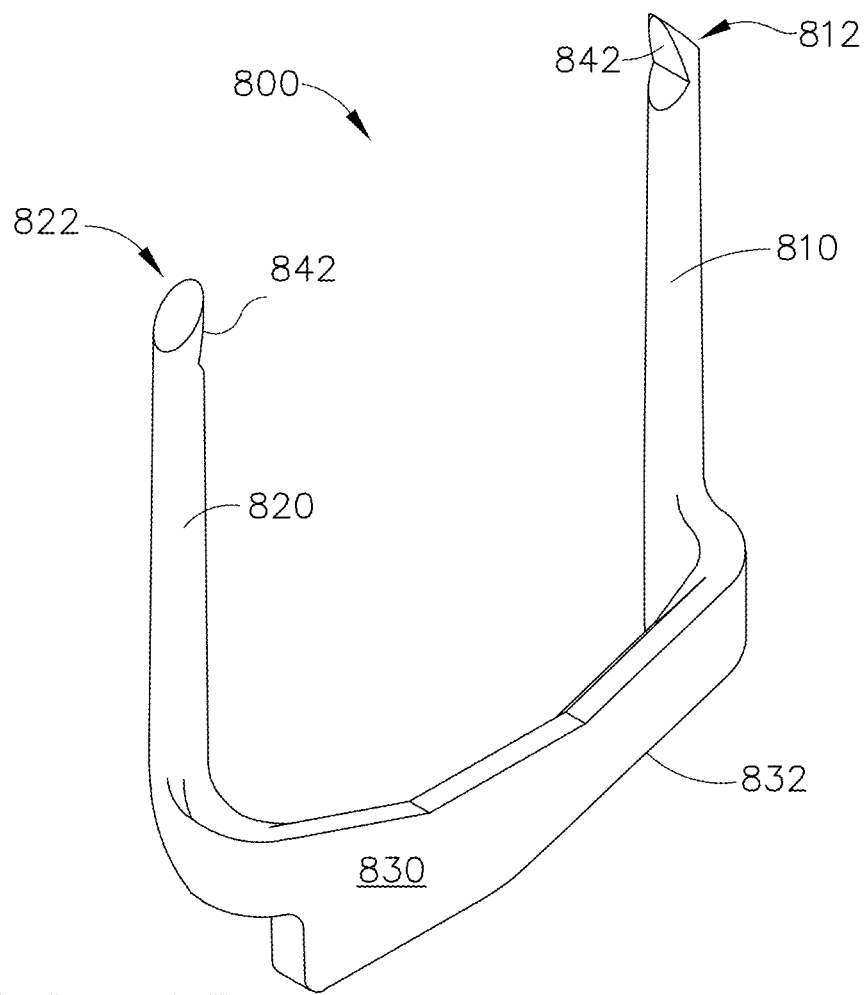
FIG. 15 is a perspective view of a staple for use with a surgical stapling instrument in accordance with at least one embodiment.
Figure 16:
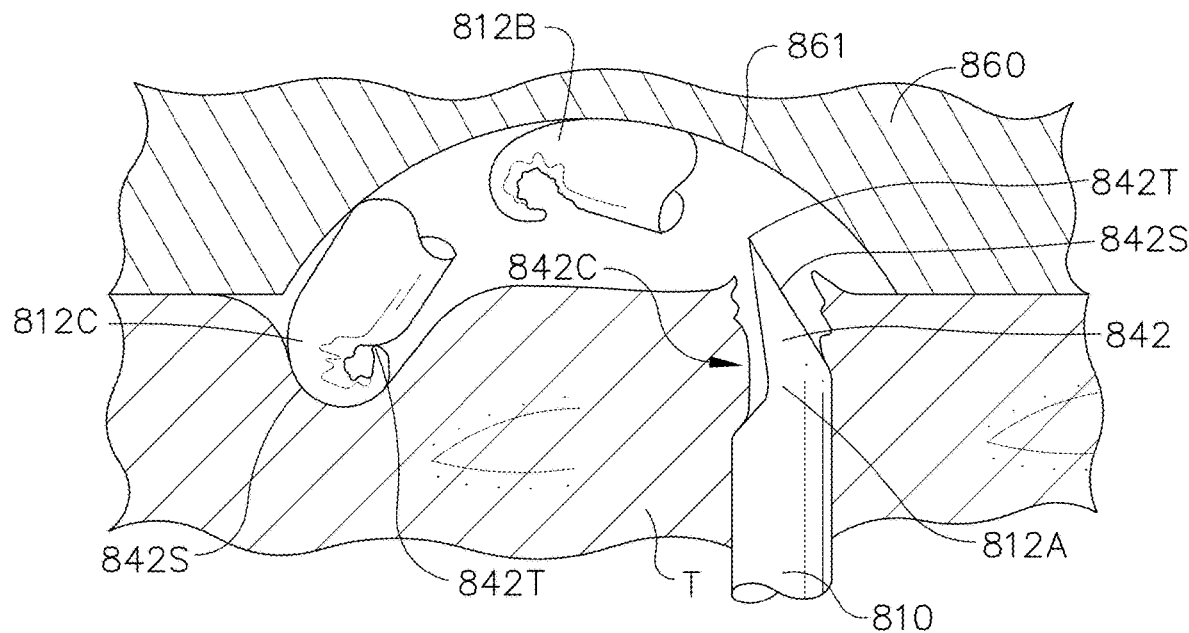
FIG. 16 is a partial cross-sectional view of an anvil illustrating a portion of the staple of FIG. 15 being formed from an unformed configuration to a formed configuration.
Figure 17:
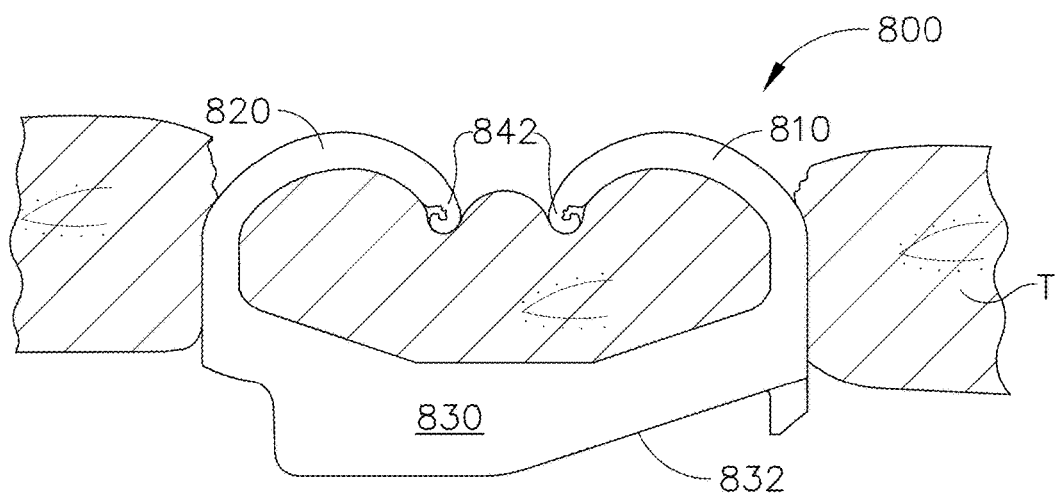
FIG. 17 is an elevation view of the staple of FIG. 15 in a formed configuration.

FIGS. 15-17 depict a staple 800 comprising staple legs 810, 820 and a staple base portion 830 having a drive surface 832. The staple legs 810, 820 comprise tips 842 configured to contact forming pockets of an anvil, such as forming pocket 861 of the anvil 860, for example. The staple tips 842 comprise a piercing tip, or portion, 842T, a curling surface 842S, and a concave cutout portion 842C. The piercing tip 842T is configured to pierce the tissue T upon ejection from the staple cartridge and, once in contact with the forming pocket 861 of the anvil 860, deform within the forming pocket 861. Deformation of the staple tip 842 is encouraged into a certain formation by utilizing the predictable deformability of the concave cutout portion 842C. The curling surface 842S of the staple tip 842 is configured to curl, or deform, from a piercing position 812A, to an intermediate formed position 812B, and to a non-piercing position 812C. Once the staple tip 842 has deformed completely, the piercing tip 842T is shielded, or isolated, from the tissue T by the curling surface 842S. This prevents further piercing of the tissue T after the tip 842 pierces the tissue upon ejection. This arrangement also prevents further injury and/or unwanted irritation that a piercing tip that is exposed after the initial piercing could possibly inflict. Preventing further piercing of the tissue T after the legs are formed also lessens the chance of the staple 800 being pulled through the tissue T. The curling surface 842S acts as a shield configured to shield the piercing tip 842T from the tissue T.

Figure 18:
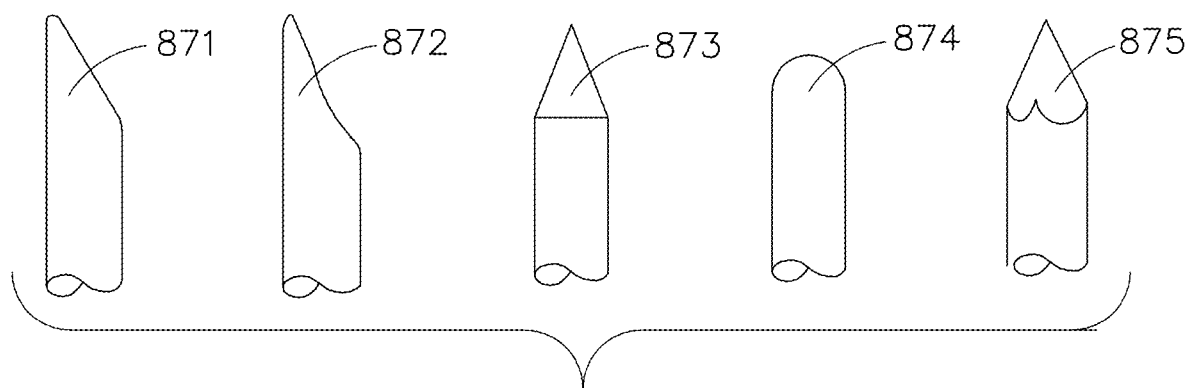
FIG. 18 includes side views of multiple staple tips in accordance with at least one embodiment.

FIG. 18 depicts multiple examples of different types of staple tips 871, 872, 873, 874, and 875 that can be employed with any suitable surgical staple such as the staples disclosed herein. Staple tip 871 comprises a triangular shape with an at least substantially flat face. Staple tip 872 comprises a face with a varying contour. Staple tip 873 comprises a rocket-like shape. Staple tip 874 comprises a nub-like profile. The nub-like profile may be substantially dull, for example. Staple tip 875 comprises a pencil-sharpened profile.

In various embodiments, the staple tips disclosed herein may comprise a material different than that of the staple to which the staple tip is connected in order to make deforming in the fashion desired easier, however, the staple tip material can still be strong enough to prevent unfolding of the staple tip after fastening tissue.

Figure 19:
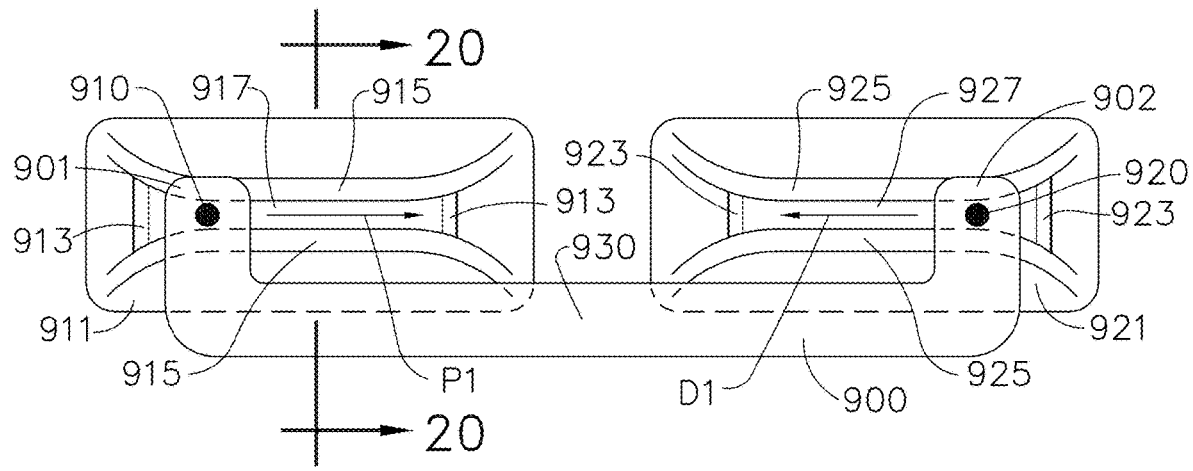
FIG. 19 is a bottom view of a staple in accordance with at least one embodiment and forming pockets of an anvil according to a first arrangement.
Figure 20:
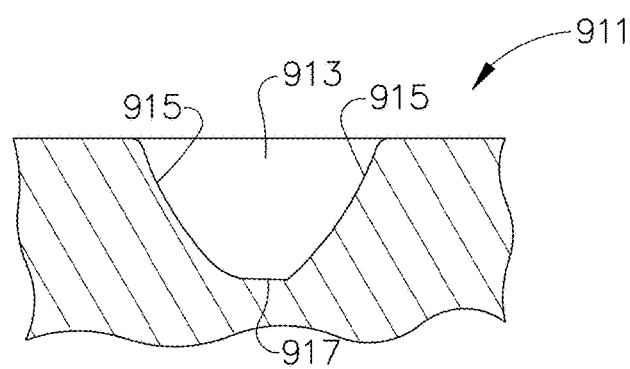
FIG. 20 is partial cross-sectional view of an anvil pocket of FIG. 19 taken along line 20-20 in FIG. 19.

Surgical staples can be encouraged to form into a desired configuration by changing the shape, size, configuration, and/or other aspects of the forming pockets configured to form the staples. FIG. 19 depicts forming pockets 911, 921 configured to form a staple 900. The staple 900 comprises staple legs 901, 902, staple tips 910, 920, and a staple base 930, wherein the staples legs 901, 902 extend from the staple base 930. The staple 900 is configured to contact and form against the corresponding forming pockets 911, 921. The forming pocket 911 comprises a forming channel surface 917 configured to receive a corresponding tip 910 and encourage the tip 910 to form in a direction P1. Shown in FIG. 20, the forming pocket 911 comprises lateral valley-like surfaces 915 and longitudinal valley-like surfaces 913 configured to funnel, or catch, the tip 910 of the staple in the event of minor misalignment upon contact. The staple 900, staple leg 901, and/or staple tip 910 may be driven off target with respect to the forming channel surface 917 upon ejection from the cartridge. The valley-like surfaces permit longitudinal and lateral roll of the staple. Although illustrated as concave surfaces, the valley surfaces may be convex or flat, for example.

The forming pocket 921 comprises a forming channel surface 927 configured to receive a corresponding tip 920 of the staple 900 and encourage the tip 920 to form in a direction D1. The direction D1 is opposite the direction P1 and, as shown in FIG. 19, illustrates an instance in which the staple legs are formed toward each other and at least substantially parallel to the staple base 930. Other embodiments are envisioned where the directions D1, P1 direct the corresponding staple legs in opposite directions but outward with respect to each other. The forming pocket 921 further comprises lateral valley-like surfaces 925 and longitudinal valley like surfaces 923 configured to funnel, or catch, the tip 920 of the staple 900 in the event of minor misalignment upon contact. The staple 900, staple leg 902, and/or staple tip 920 may be driven off target with respect to the forming channel surface 927 upon ejection from the cartridge.

In various embodiments, the longitudinal valley-like surfaces may comprise two separate valley surfaces. The two separate valley surfaces may comprise an initial valley surface nearest the intended point of contact for the corresponding staple tip. The initial valley surface may comprise a larger range of misalignment protection than the other of the separate valley surfaces. The initial valley surface may comprise a larger width and/or height than the other of the separate valley surfaces, for example.

Figure 21:
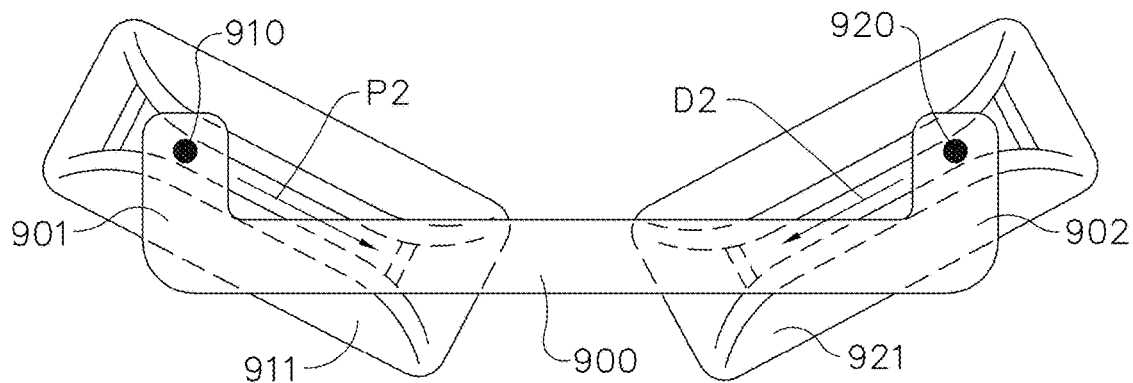
FIG. 21 is a bottom view of the staple and the forming pockets of FIG. 19 according to a second arrangement.

FIG. 21 depicts another arrangement of the staple pockets 911, 921 discussed above. However, the staple pockets 911, 921 in the illustrated arrangement are configured to direct the staple tips inward toward the staple base 130. The leg 901 and tip 910 are configured to be formed in direction P2. The leg 902 and tip 920 are configured to be formed in direction D2. The directions P2, D2 are transverse. Other embodiments are envisioned where the directions P2, D2 direct the corresponding staple legs and tips away from the staple base, or outward.

Figure 22:
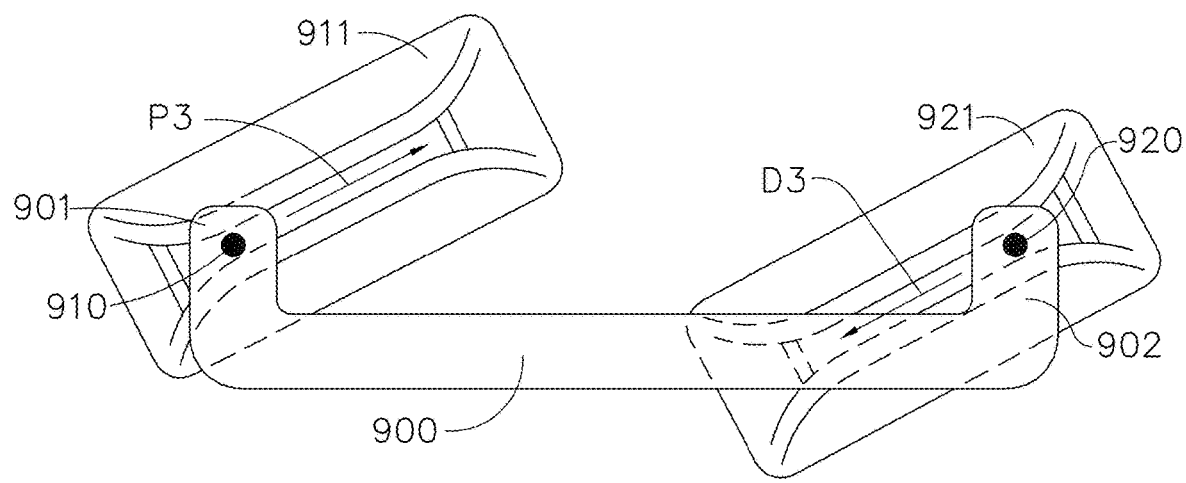
FIG. 22 is a bottom view of the staple and the forming pockets of FIG. 19 according to a third arrangement.

FIG. 22 depicts yet another arrangement of the staple pockets 911, 921 discussed above. The staple pockets 911, 921 in the illustrated arrangement are configured to form the corresponding staple legs 901, 902 and tips 910, 920 in opposite directions where one of the staple legs 902 is directed toward the staple base 930 and one of the staple legs 901 is directed away from the staple base 930. The leg 901 and tip 910 are configured to form in direction P3. The leg 902 and tip 920 are configured to form in direction D3. The directions P3, D3 are at least substantially parallel. Other embodiments are envisioned where the directions P3, D3 are not parallel.

Figure 23:
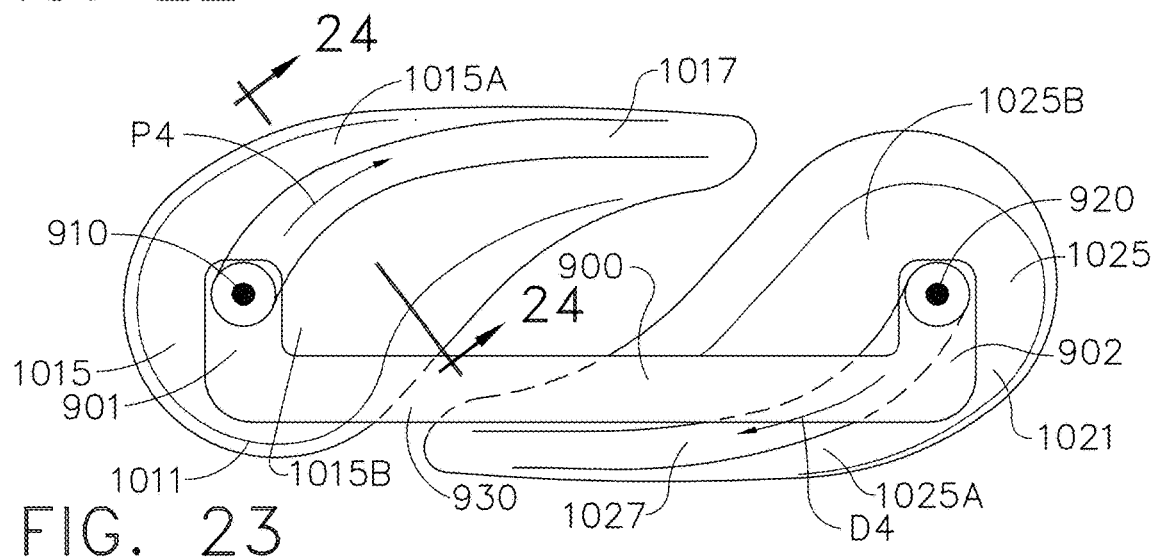
FIG. 23 is a bottom view of the staple of FIG. 19 and forming pockets in accordance with at least one embodiment.
Figure 24:
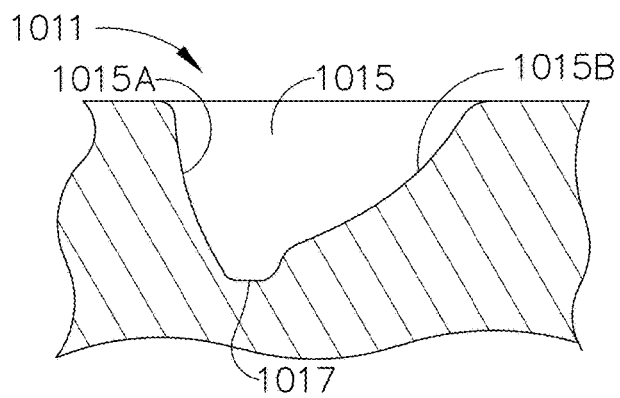
FIG. 24 is a partial cross-sectional view of an anvil pocket of FIG. 23 taken along line 24-24 in FIG. 23.

FIGS. 23 and 24 depict another embodiment of forming pockets comprising forming pockets 1011, 1021 configured to deform the staple 900. The forming pockets 1011, 1021 comprise an ear-like shape providing nested pockets. This type of arrangement can save space on the staple forming surface of an anvil to allow for more staple pockets and, as a result, more staples in a staple cartridge in a lesser amount of space. The forming pocket 1011 comprises a forming channel surface 1017 configured to receive the corresponding tip 910 and encourage the tip 910 to form in a curved direction P4. Shown in FIG. 24, the forming pocket 1011 comprises a first valley-like, curved surface 1015A and a second valley-like, curved surface 1015B configured to funnel, or catch, the tip 910 of the staple in the event of minor misalignment during contact. The staple 900, staple leg 901, and/or staple tip 910 may be driven off target with respect to the forming channel surface 917 upon ejection from its staple cavity. The valley-like surfaces permit some longitudinal and lateral roll of the staple. Although illustrated as concave surfaces, the valley surfaces may be convex or flat, for example.

The forming pocket 1021 comprises a forming channel surface 1027 configured to receive the corresponding tip 920 of the staple 900 and encourage the tip 920 to form in a direction D4. FIG. 23 illustrates an instance in which the staple legs 901, 902 are formed toward each other with one staple leg 901 formed away from the staple base 930 and one staple leg 902 formed toward the staple base 930. Other embodiments are envisioned where the directions P4, D4 direct the corresponding staple legs 901, 902 in opposite directions but outward with respect to each other. The forming pocket 1021 comprises a first valley-like, curved surface 1025A and a second valley-like, curved surface 1025B configured to funnel, or catch, the tip 920 of the staple 900 in the event of minor misalignment before and/or during contact.

Figure 25:
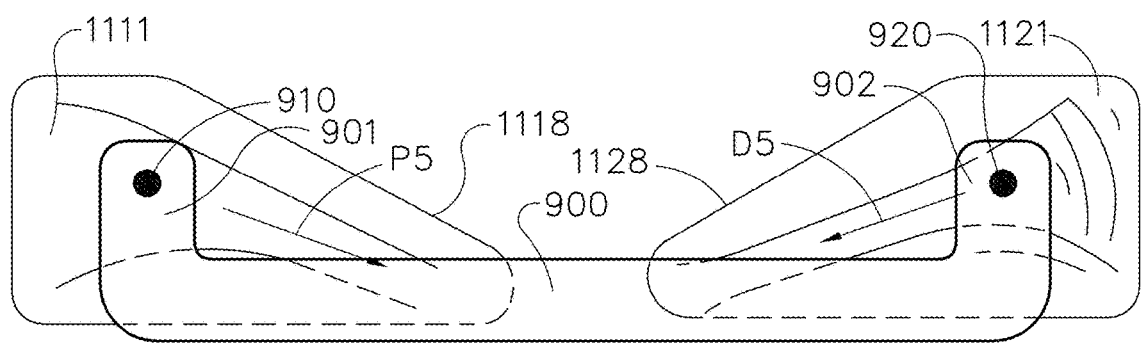
FIG. 25 is a bottom view of the staple of FIG. 19 and forming pockets in accordance with at least one embodiment.

FIG. 25 depicts yet another embodiment of forming pockets comprising anvil forming pockets 1111, 1121 configured to deform corresponding staple legs 901, 902 and tips 910, 920 toward the staple base 930. The forming pockets 1111, 1121 are trapezoidal in shape and can be nested with other similar forming pockets using less space on a forming surface of an anvil. The forming pockets 1111, 1121 are configured to form the staple legs 901, 902 and tips 910, 920 in directions P5, D5, respectively.

Figure 26:
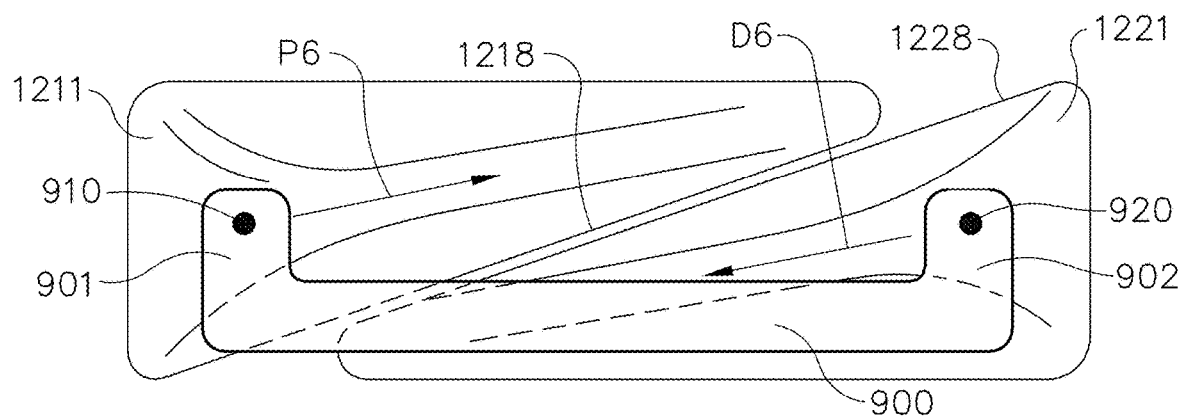
FIG. 26 is a bottom view of the staple of FIG. 19 and forming pockets in accordance with at least one embodiment.

FIG. 26 depicts yet another embodiment of forming pockets comprising anvil forming pockets 1211, 1221 configured to deform corresponding staple legs 901, 902 and tips 910, 920 in directions P6, D6, respectively. The forming pockets 1111, 1121 are triangular in shape and can be nested with each other comprising an even more compact forming pocket arrangement on an anvil of a surgical stapling instrument.

Referring now to FIGS. 27-27B, a staple leg 1300 is depicted. The staple leg 1300 comprises a substantially round staple tip with a substantially square staple leg and a staple leg body portion 1301. The staple leg 1300 comprises hardened corners formed using a coining process, for example, where the corners 1303A, 1303B, 1303C, and 1303D were rounded in order to create preferential bending planes. Stated another way, the staple leg 1300 comprises a cross-sectional profile configured to encourage the staple leg 1300 to bend in a certain direction due to the corner hardening upon contact with an anvil. The corners 1303A, 1303B, 1303C, and 1303D may vary in hardness from one corner to the next, or, may comprise two corners with a first hardness and the other two corners with a second hardness. The corners 1303A, 1303B, 1303C, and 1303D may be coined to provide different radial profiles on the same staple leg. For example, the corner 1303A comprises a radial profile with a radius RA greater than the radius RB of the radial profile of corner 1303B shown in FIG. 27B.

Portions of the staples disclosed herein may be hardened at various times of the manufacturing process with any suitable means. For example, hardening process may include bronzing, chemical vapor deposition, physical vapor deposition, laser surface treatment, thermal oxidation, ion nitriding, and/or solid state diffusion, for example. Other portions of the staples may be prevented from being hardened by these processes. Other portions of the staples may be locally annealed, such as the staple tips, for example. Increasing hardness in certain areas can increase the force required to unform the staples after the staples have assumed a fired configuration.

Figure 28:
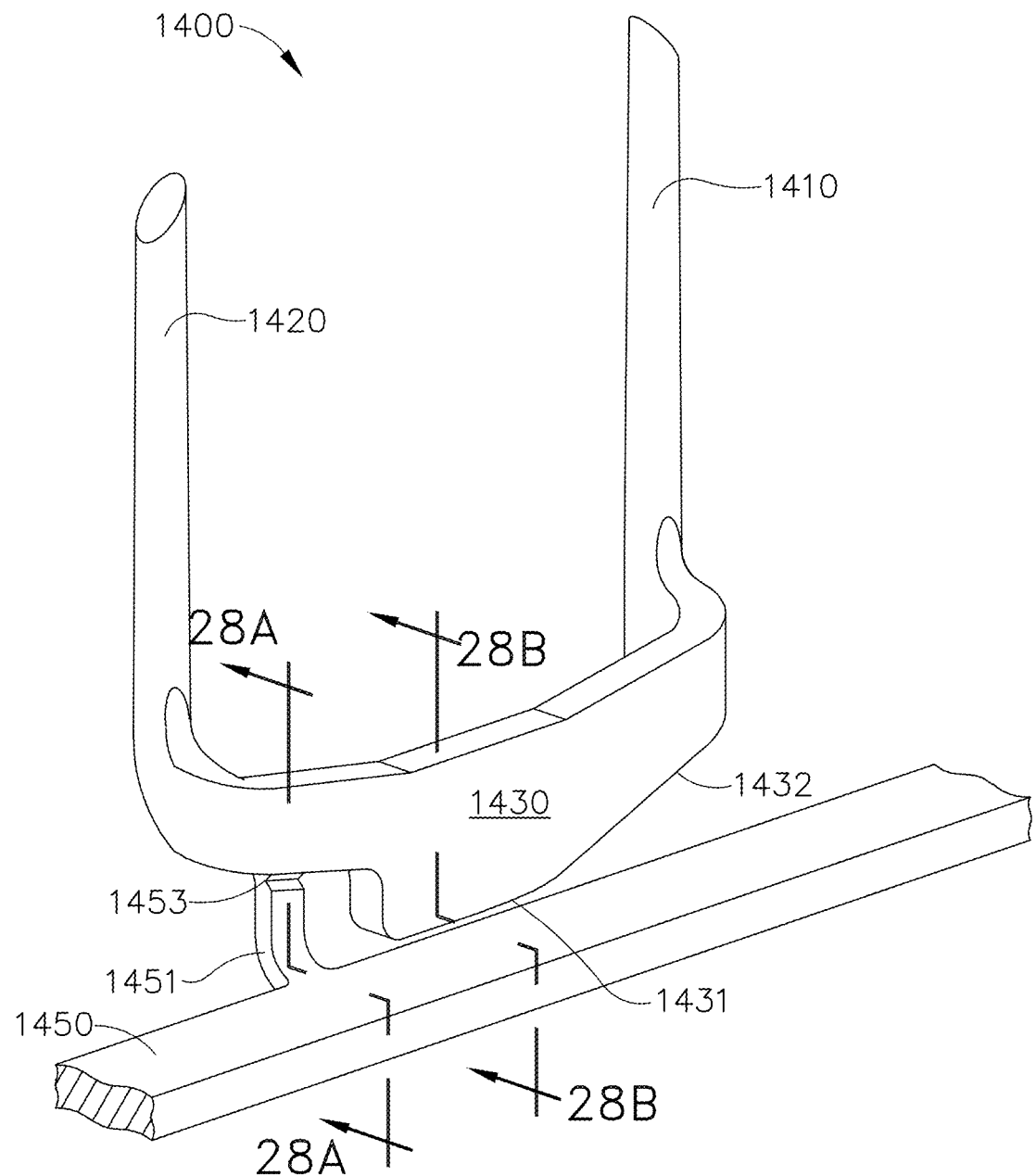
FIG. 28 is a perspective view of a portion of a staple strip manufactured with progressive die stamping.
Figure 28A:
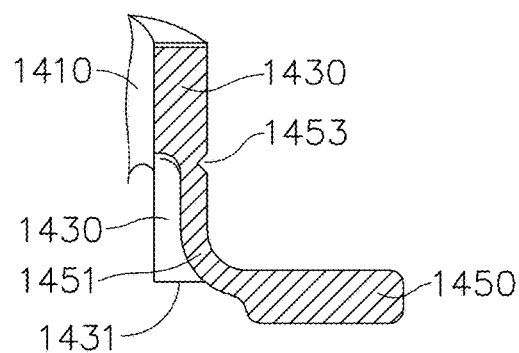
FIG. 28A is a partial cross-sectional view of the portion of the staple strip of FIG. 28 taken along line 28A-28A in FIG. 28.
Figure 28B:
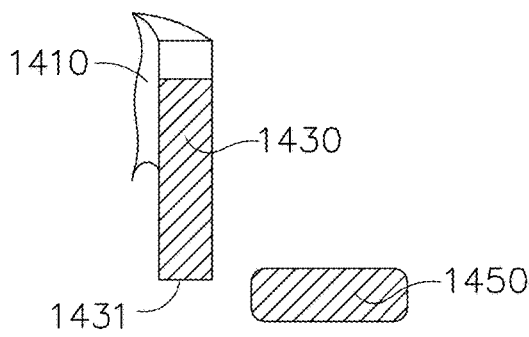
FIG. 28B is a partial cross-sectional view of the portion of the staple strip of FIG. 28 taken along line 28B-28B in FIG. 28.
Figure 28C:
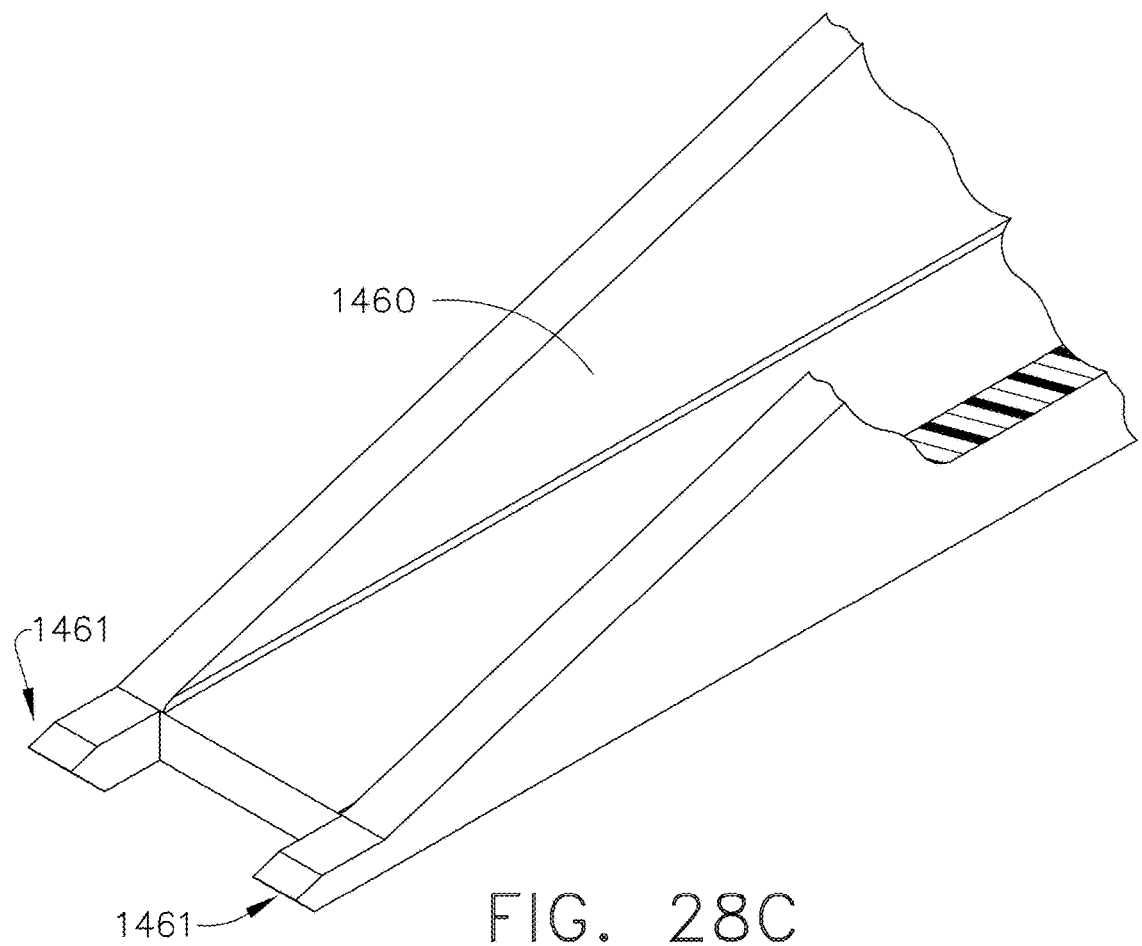
FIG. 28C is a partial perspective view of a sled configured to engage the staple strip of FIG. 28.

FIGS. 28-28C depict a staple 1400 and a sled 1460 in accordance with at least one embodiment. The staple 1400 comprises staple legs 1410, 1420, a staple base portion 1430 from which the staple legs 1410, 1420 extend, a drive surface 1432, and a bottom surface 1431. The staple legs 1410, 1420 extend from the staple base portion 1430 in a plane which is a parallel and offset with respect to a plane defined by the staple base portion 1430. The staple 1400 is made with progressive die stamping utilizing a base strip 1450 and a connector portion 1451. Although only a single staple 1400 is shown, a plurality of staples 1400 are attached to the base strip 1450. The connector portion 1451 connects the staple 1400, specifically the staple base portion 1430, to the base strip 1450. The connector portion 1451 comprises a discontinuity, or notch, 1453 configured to permit the staples 1400 to detach from the strip 1450. In at least one instance, the sled 1460 comprises release portions, or striking portions, 1461. The release portions 1461 of the sled 1460 are configured to engage the discontinuities 1453, or connector portions 1451, to separate, break, and/or shear, the staples 1400 from the base strip 1450 and permit the staples to be ejected from their staple cavities by the sled 1460.

Embodiments are envisioned where the base strip 1450 comprises alignment features such as holes, for example, which engage corresponding alignment features on a staple cartridge. Such alignment features may comprise protrusions, for example, that align with the alignment features of the base strip 1450. In various instances, a person loading the staples into the cartridge could align the staples with the staple cavities and/or align the alignment features before pushing the staples into the staple cavities. Certain embodiments are envisioned in which the staple cartridge comprises engagement features configured to engage the discontinuities 1453 when the strip assemblies are loaded into the staple cartridge. The engagement features allow the staples 1400 to be separated from the strip 1450 when the staples 1400 are loaded into a staple cartridge instead of when the staples 1400 are fired. Manufacturing staples using progressive die stamping can permit staples to have different crown sizes, shapes, and/or configurations as well as staple leg sizes, shapes, and/or configurations. Another advantage of using progressive die stamping technology may include the ability to alter the spacing of the rows of staples in which the staples are aligned.

Figure 29:
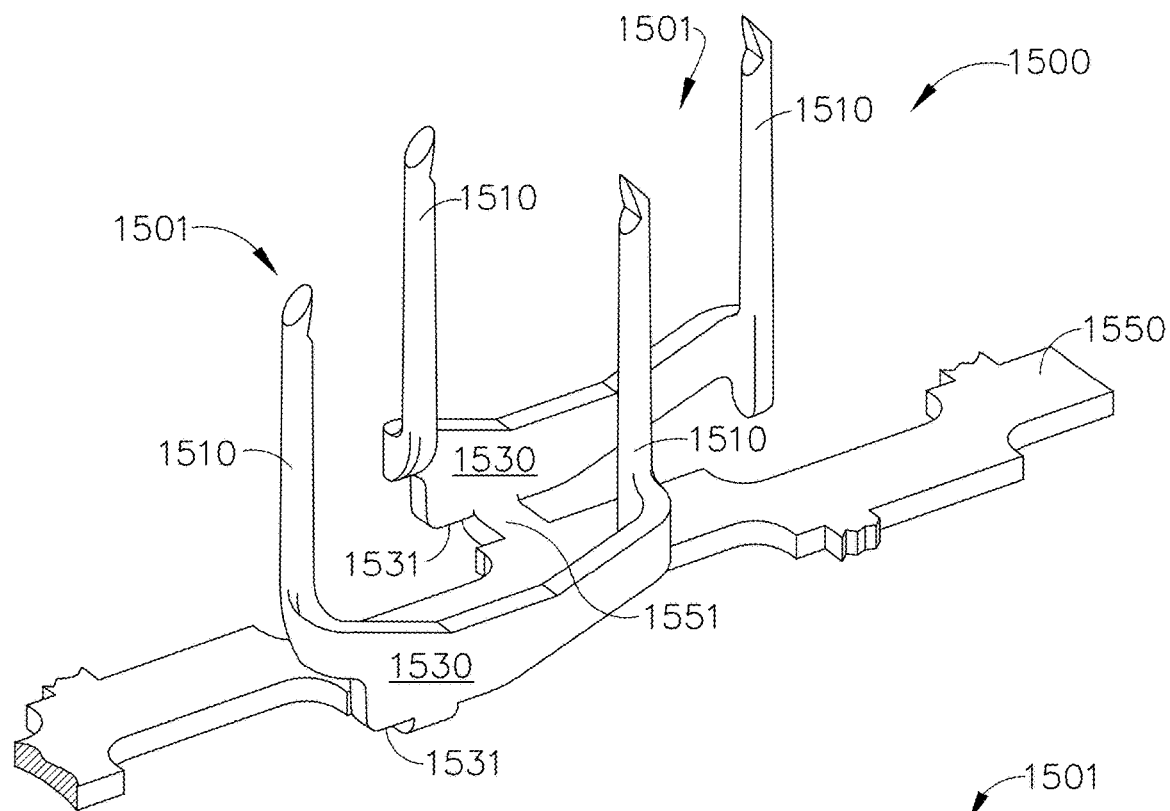
FIG. 29 is a perspective view of a portion of a staple strip manufactured with progressive die stamping in accordance with at least one embodiment.
Figure 30:
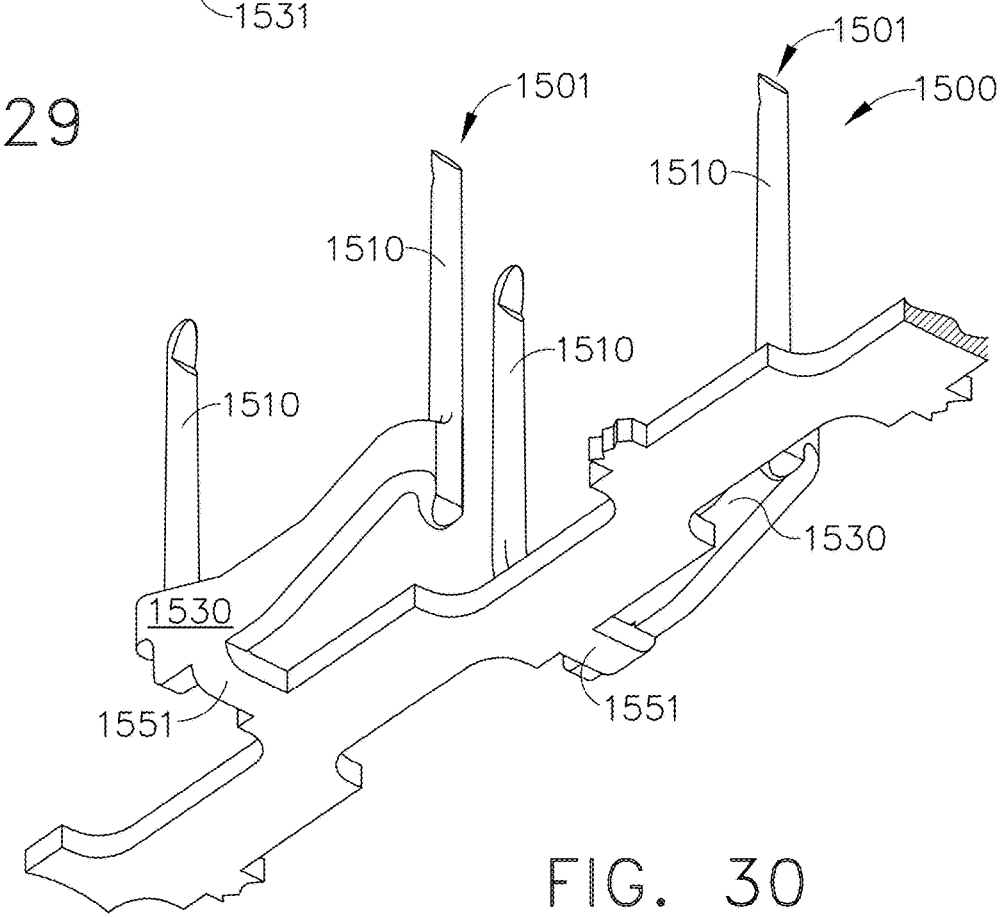
FIG. 30 is a bottom perspective view of the staple strip of FIG. 29.

FIGS. 29 and 30 depict another embodiment of a strip 1500 of staples 1501 made with progressive die stamping. The strip 1500 of staples 1501 comprises a base strip 1550, a connector portion 1551, and staples 1501. Each staple 1501 comprises, one, a staple base portion 1530 comprising a bottom surface 1531 and, two, staple legs 1510 extending from the staple base portion 1530. The connector portion 1551 attaches the bottom surface 1531 of the staple base portion 1530 to the base strip 1550. The staple legs are bent up from the staple base portion 1530 such that the legs 1510 reside in a plane which is offset and at least substantially parallel to a plane defined by the staple base portion 1530. In the illustrated embodiment, the staple legs 1510 are bent in a direction opposite to that of the connector portion 1551. Bending the legs 1510 and the connector portions 1551 in this manner can permit a more dense staple row arrangement. The connector portions 1551 can comprise a discontinuity enabling the staples 1501 to be released from the base strip 1550 upon loading the staples 1501 into a staple cartridge and/or firing the staples 1501 from the staple cartridge as discussed in the previous embodiment.

Figure 31:
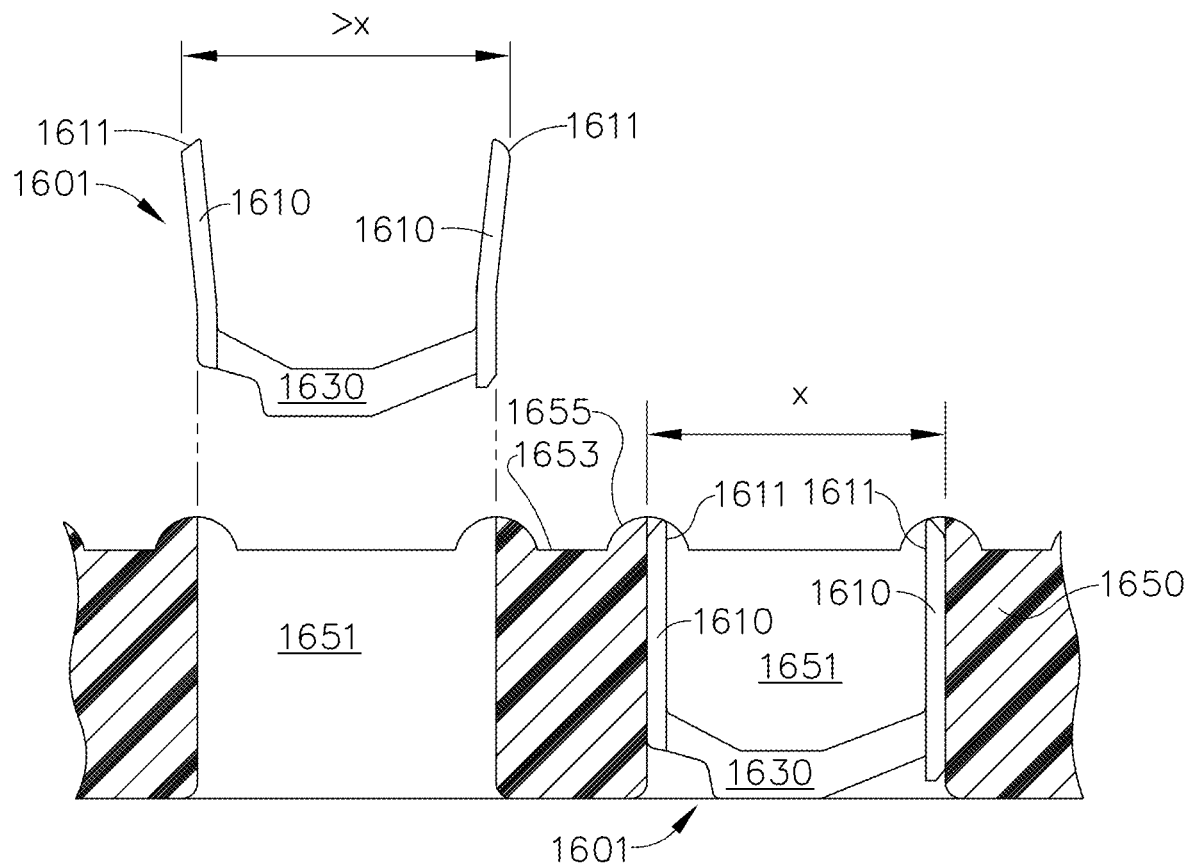
FIG. 31 is a partial cross-sectional view of a staple cartridge and staples in accordance with at least one embodiment.

FIG. 31 depicts a plurality of staples 1601 and a cross-sectional view of a portion of a staple cartridge 1650 in accordance with at least one embodiment. The staples 1601 are removably stored within corresponding staple cavities 1651 of the staple cartridge 1650. The staple cartridge 1650 comprises a deck surface 1653 and staple leg supports 1655. The staples 1601 comprise, one, staple legs 1610 which each comprise a staple tip 1611 and, two, a staple base portion 1630 from which the staple legs 1610 extend. Each staple 1601 comprises a pre-load configuration, a loaded configuration, and a fired configuration where the staple 1601 is ejected from the staple cartridge 1650 and formed against corresponding forming pockets of an anvil. The staple legs 1610 are bent outwardly with respect to the staple base portions 1630 in the pre-load configuration. The staple legs 1610 are biased against sidewalls of the corresponding staple cavity 1651 in the loaded configuration and define a first distance X between the tips 1611 of the staple legs 1610. In the pre-load configuration, the distance between the staple tips 1611 of the staple legs 1610 is greater than X. This biasing force helps support the staples 1601 in the staple cartridge 1650.

Figure 32:
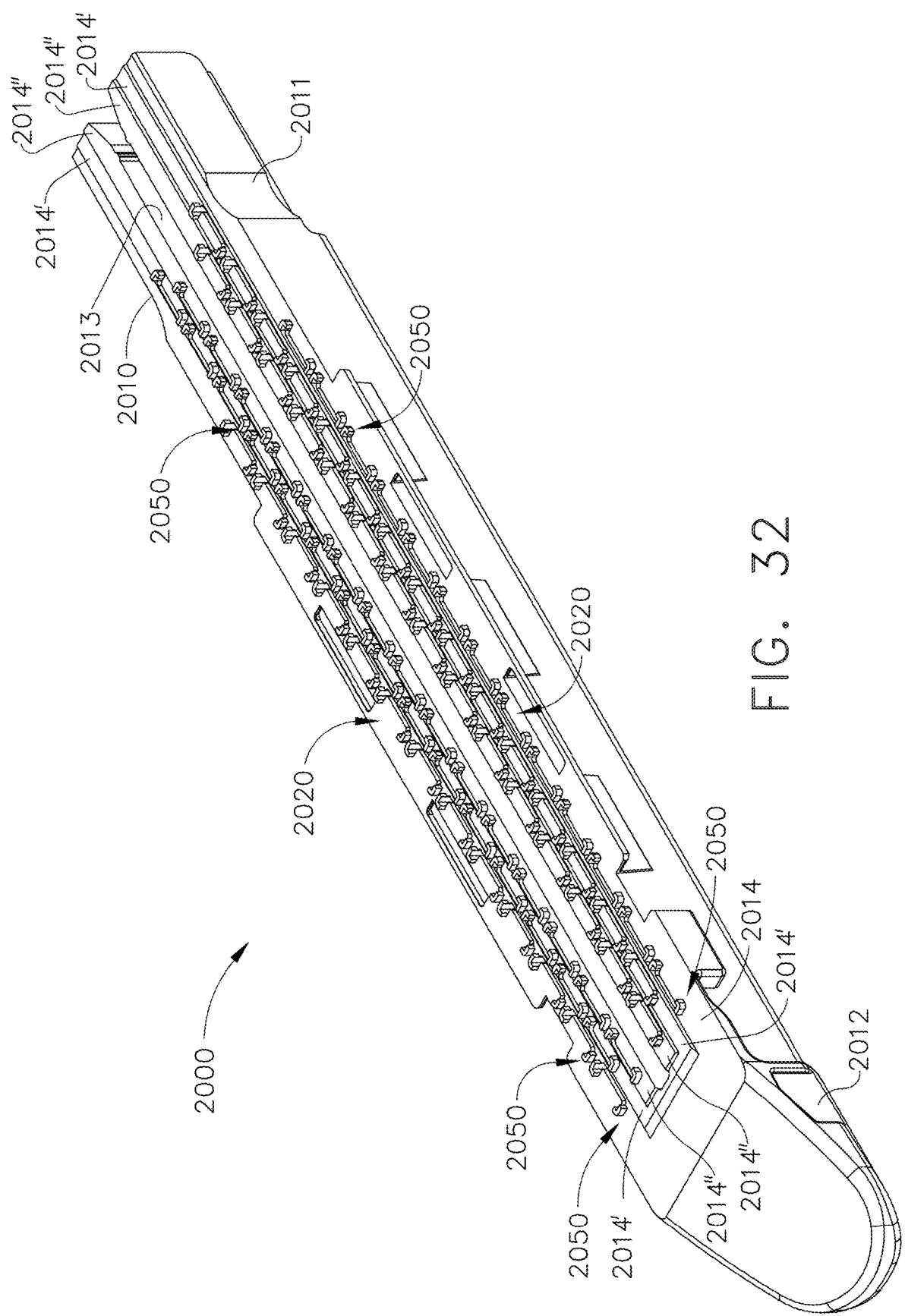
FIG. 32 is a perspective view of a staple cartridge assembly in accordance with at least one embodiment.

A staple cartridge 2000 is illustrated in FIGS. 32-34. The staple cartridge assembly 2000 comprises a cartridge body 2010. The cartridge body 2010 is positionable in and removable from a jaw of a surgical stapling instrument. As a result, the staple cartridge 2000 is replaceable; however, other embodiments are envisioned in which the staple cartridge 2000 is not replaceable. The cartridge body 2010 comprises a proximal end 2011, a distal end 2012, and a deck 2014 extending between the proximal end 2011 and the distal end 2012. The deck 2014 is configured to support the tissue of a patient when the tissue is compressed against the deck 2014.

Figure 40:
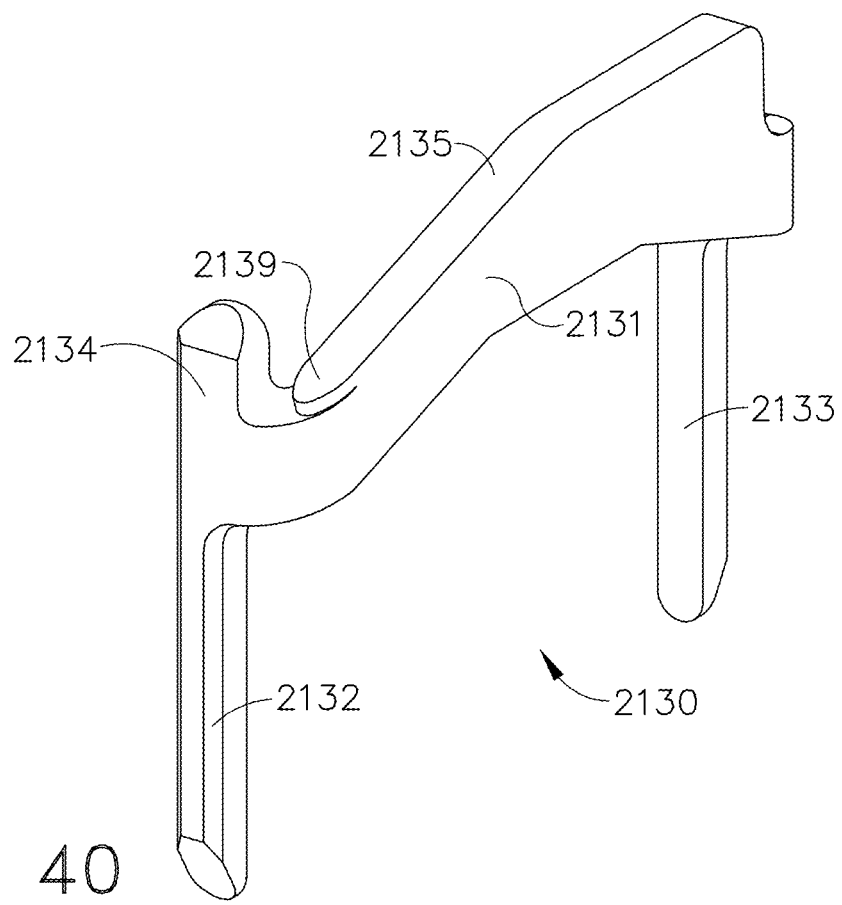
FIG. 40 is a bottom perspective view of the staple of FIG. 39.

The cartridge body 2010 further comprises a plurality of staple cavities 2020 defined therein. The staple cavities 2020 are arranged in six longitudinal rows extending between the proximal end 2011 and the distal end 2012; however, any suitable arrangement of staple cavities 2020 can be utilized. A staple, such as staple 2130 (FIG. 40), for example, is removably stored in each staple cavity 2020. As discussed in greater detail below, the staples are ejected from the staple cavities 2020 by a firing member when the firing member is moved from the proximal end 2011 of the cartridge body 2010 toward the distal end 2012.

Further to the above, the staples are moved from an unfired position to a fired position by the firing member. The firing member lifts the staples toward an anvil, such as anvil 2190 (FIG. 37), for example, to deform the staples between an unfired, undeformed configuration and a fired, deformed configuration. The cartridge body 2010 further comprises a longitudinal slot 2013 defined therein. The slot 2013 is configured to receive the staple firing member and/or a tissue cutting member therein when the staples are ejected from the staple cavities 2020.

In various embodiments, further to the above, the staples do not protrude above the deck 2014 until they are moved toward the anvil by the firing member. Such embodiments may frequently utilize small staples. In other embodiments, the legs of the staples protrude above the deck 2014 when the staples are in their unfired positions. In at least one such embodiment, the cartridge body 2010 further comprises projections 2050 extending from the deck 2014. The projections 2050 extend the staple cavities 2020 above the deck 2014 and guide the staples toward the anvil when the staples are being ejected from the staple cartridge 2000. In such embodiments, the staples may not extend above the projections 2050 until they are moved toward the anvil by the firing member.

Referring primarily to FIG. 34, the projections 2050 do not extend around the entirety of the staple cavities 2020. A first projection 2050 is positioned adjacent a first end of each cavity 2020 and a second projection 2050 is positioned adjacent a second end of each cavity 2020. Each first projection 2050 extends around a first staple leg guide 2022 of a staple cavity 2020 and each second projection 2050 extends around a second staple leg guide 2023 of the staple cavity 2020. Each first projection 2050 provides a proximal bracket which can control and guide the proximal leg of a staple and each second projection 2050 provides a distal bracket which can control and guide the distal leg of the staple. The first projection 2050 of each staple cavity 2020 is not symmetrical with respect to the first end of the staple cavity 2020 and does not extend around the entirety of the first end of the cavity 2020. Similarly, the second projection 2050 of each staple cavity 2020 is not symmetrical with respect to the second end of the staple cavity 2020 and does not extend around the entirety of the second end of the cavity 2020. The first projection 2050 and the second projection 2050 comprise mirror images of one another and are symmetrically arranged with respect to the center of each staple cavity 2020; however, any suitable arrangement of projections could be utilized.

As illustrated in FIGS. 32-34, the cartridge body 2010 comprises steps 2014' and steps 2014" which extend upwardly from the deck 2014. More specifically, the steps 2014' extend upwardly from the deck 2014 and the steps 2014" extend upwardly from the steps 2014'. As a result, the steps 2014" may apply a larger compressive pressure to the tissue than the steps 2014' and, similarly, the steps 2014' may apply a larger compressive pressure to the tissue than the deck 2014. The steps 2014' and 2014" comprise staggered longitudinal plateaus; however, the steps 2014' and 2014" may comprise any suitable configuration. Moreover, further to the above, the projections 2050 extending from the steps 2014" extend above the projections 2050 extending from the steps 2014' and, similarly, the projections 2050 extending from the steps 2014' extend above the projections 2050 extending from the deck 2014. Stated another way, the projections 2050 extending from the deck 2014, the steps 2014', and the steps 2014" are staggered.

A staple cartridge 2100 is illustrated in FIGS. 35-38. The staple cartridge assembly 2100 comprises a cartridge body 2110 and is similar to the staple cartridge assembly 2000 and/or the other staple cartridges disclosed herein in many respects. The cartridge body 2110 comprises a deck 2114, a plurality of staple cavities 2120a, and a plurality of staple cavities 2120b. The staple cavities 2120a are similar to the staple cavities 2120b in many respects. For instance, the staple cavities 2120a and 2120b both comprise a central slot 2121 having a proximal end and a distal end, a proximal staple leg guide 2122 extending laterally from the proximal end of the central slot 2121, and a distal staple leg guide 2123 extending laterally from the distal end of the central slot 2121. That said, the staple cavities 2120a and the staple cavities 2120b are oriented in different directions. More particularly, the staple leg guides 2122, 2123 of the staple cavities 2120a extend toward the staple cavities 2120b and, similarly, the staple leg guides 2122, 2123 of the staple cavities 2120b extend toward the staple cavities 2120a; however, any suitable arrangement can be utilized.

A staple 2130a is positioned in each staple cavity 2120a and a staple 2130b is positioned in each staple cavity 2120b. The staples 2130a and the staples 2130b are similar in many respects. For instance, each staple 2130a comprises a base, or crown, 2131, a proximal leg 2132 extending from a proximal end of the base 2131, and a distal leg 2133 extending from a distal end of the base 2131. That said, the staples 2130a, 2130b are adapted in a manner to fit within the staple cavities 2120a, 2120b, respectively. For example, when the staples 2130a are positioned in the staple cavities 2120a and the staples 2130b are positioned in the staple cavities 2120b, the legs 2132, 2133 of the staples 2130a extend toward the staples 2130b and the legs 2132, 2133 of the staples 2130b extend toward the staples 2130a; however, other arrangements are possible.

Figure 35:
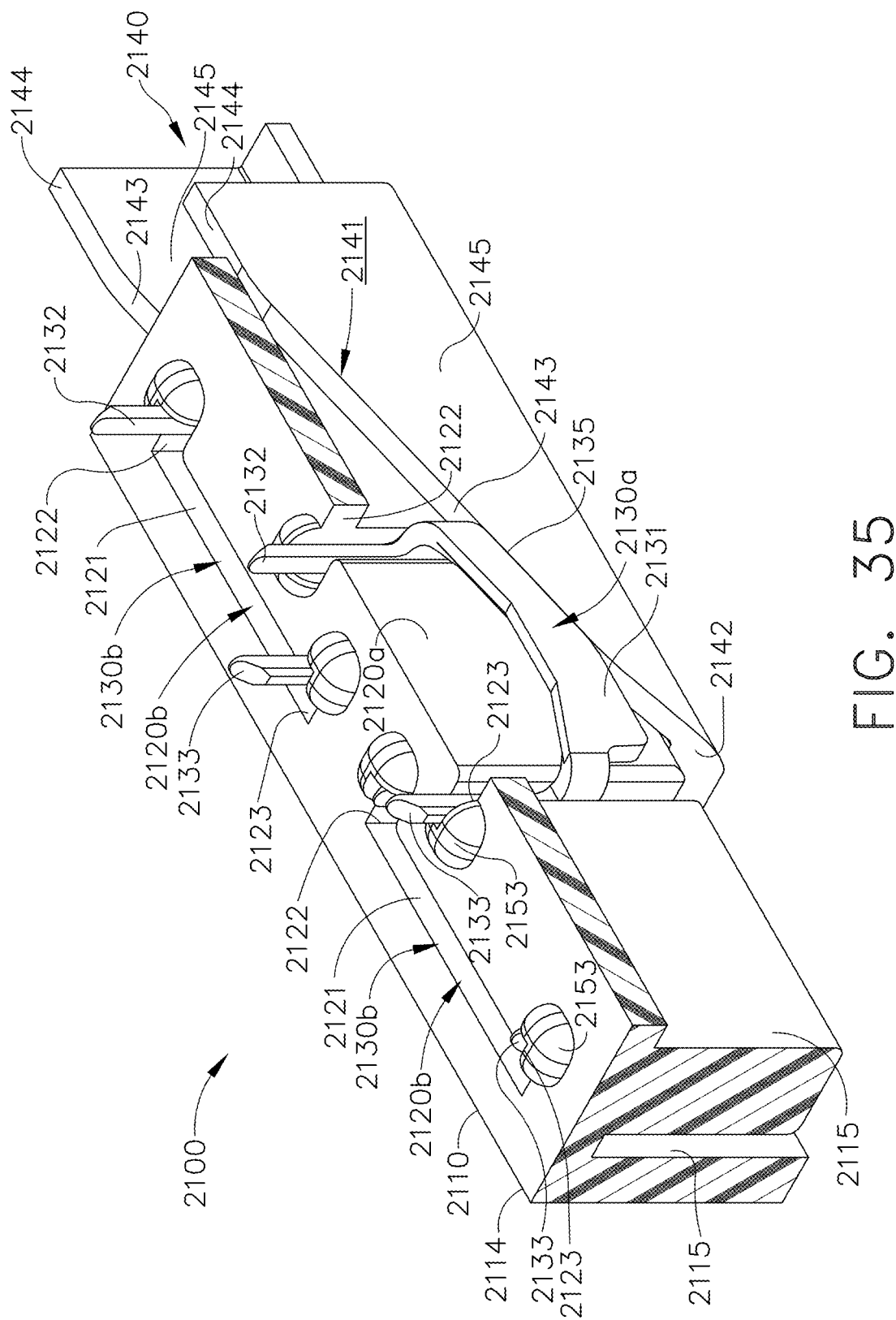
FIG. 35 is a partial cross-sectional perspective view of a staple cartridge assembly in accordance with at least one embodiment illustrating staples being ejected from the staple cartridge assembly by a firing member.
Figure 36:
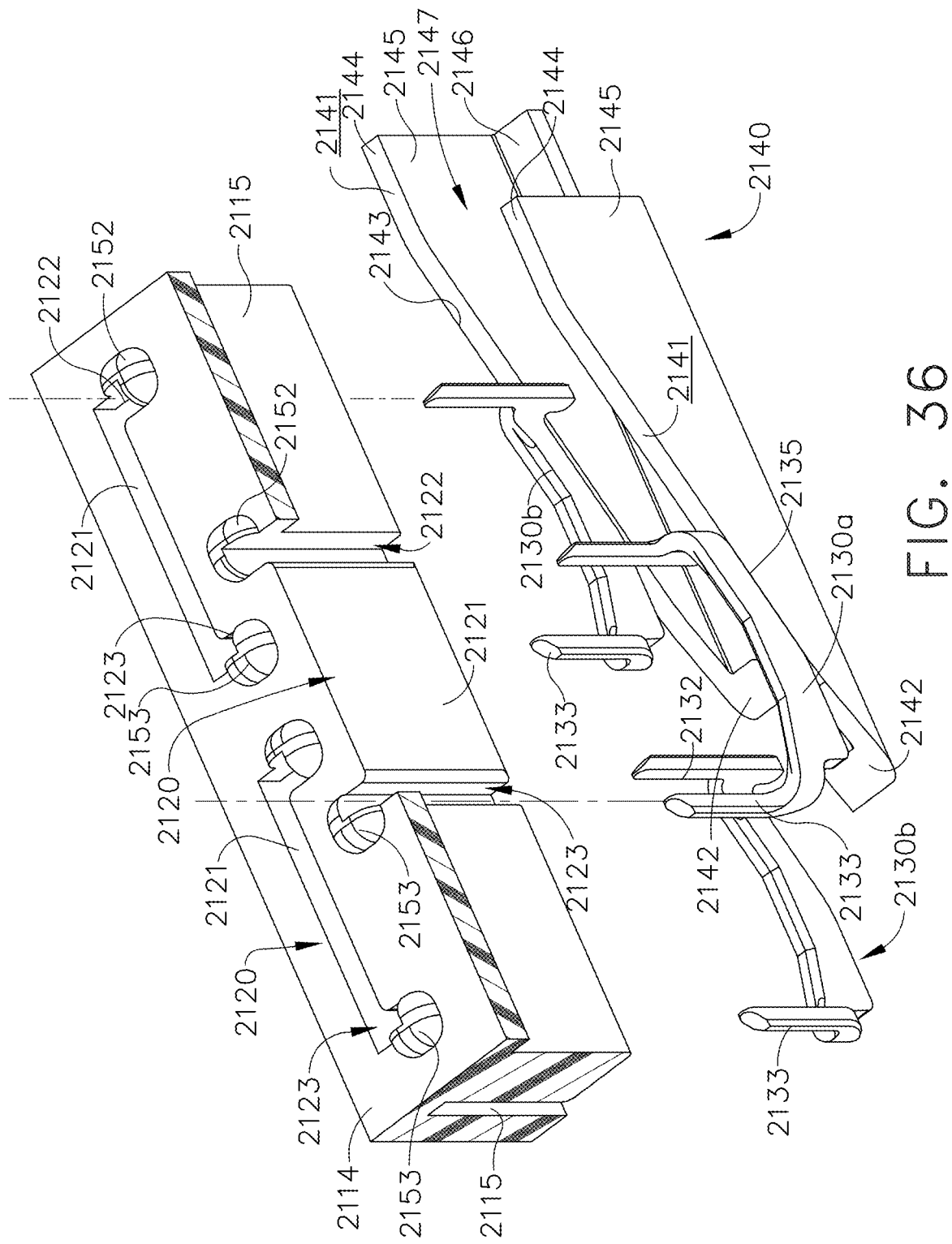
FIG. 36 is a partial exploded view of the staple cartridge assembly of FIG. 35.

Further to the above, the proximal legs 2132 of the staples 2130a, 2130b are positioned within the staple leg guides 2122 when the staples 2130a, 2130b are stored in the staple cavities 2120a, 2120b, respectively. Similarly, the distal legs 2133 of the staples 2130a, 2130b are positioned within the staple leg guides 2123 when the staples 2130a, 2130b are stored in the staple cavities 2120a, 2120b, respectively. Moreover, the bases 2131 of the staples 2130a, 2130b are positioned in the central slots 2121 of the staple cavities 2120 when he staples 2130a, 2130b are stored in the staple cavities 2120a, 2120b, respectively. Referring primarily to FIG. 35, the tips of the staple legs 2132, 2133 extend above the deck 2114 of the cartridge body 2110 when the staples 2130a, 2130b are in their unfired positions. That said, the tips of the staple legs 2132 are at least partially surrounded by proximal projections 2152 extending from the deck 2114 and the tips of the staple legs 2133 are at least partially surrounded by distal projections 2153 extending from the deck 2114. The proximal projections 2152 extend around the proximal staple leg guides 2122, but they do not extend around the proximal ends of the central slots 2121. Similarly, the distal projections 2153 extend around the distal staple leg guides 2123, but they do not extend around the distal ends of the central slots 2121.

Figure 38:
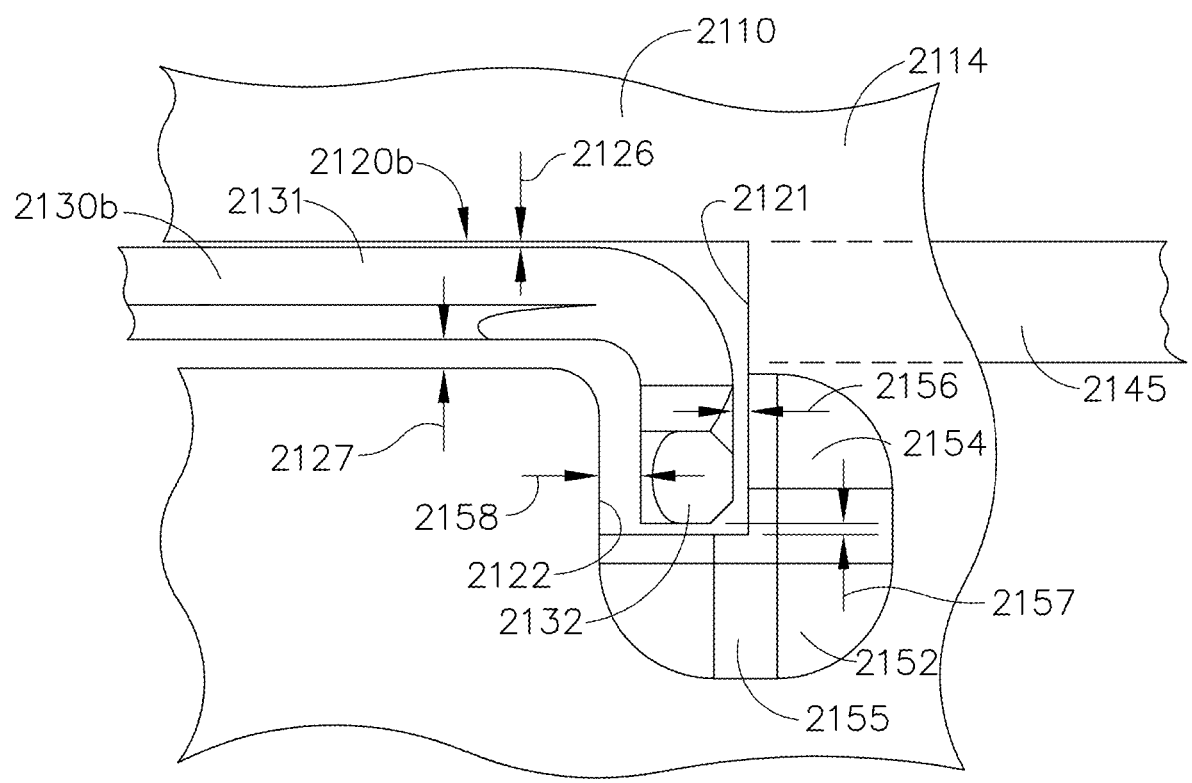
FIG. 38 is a partial plan view of a staple positioned in a staple cavity of the staple cartridge assembly of FIG. 35.

Turning now to FIG. 38, each proximal projection 2152 comprises a first portion 2154 which extends around a proximal side of the proximal guide slot 2122 and a second portion 2155 which extends around a lateral side of the proximal guide slot 2122. The proximal projection 2152 does not extend around a distal side of the proximal guide slot 2122; however, it is envisioned that the proximal projection 2152 can extend around the distal side of the proximal guide slot in alternative embodiments. Similarly, each distal projection 2153 comprises a first portion which extends around a distal side of the distal guide slot 2123 and a second portion which extends around a lateral side of the distal guide slot 2123. The distal projection 2153 does not extend around a proximal side of the distal guide slot 2123; however, it is envisioned that the distal projection 2153 can extend around the proximal side of the distal guide slot in alternative embodiments. In any event, the arrangement depicted in FIG. 38 protects the staple legs 2132, 2133 when the staples 2130a, 2130b are in their unfired positions and, in addition, guide the staples 2130a, 2130b as the staples are being fired. Such an arrangement also appropriately controls the flow of tissue relative to the deck 2114 of the cartridge body 2110.

Referring again to FIG. 38, the staple cavities 2120a and the staples 2130a are sized and configured such that clearance gaps are provided between the staples 2130a and the staple cavities 2120a. For example, a clearance gap 2156 is present between the proximal leg 2132 of a staple 2130b and the proximal sidewall of the proximal guide slot 2122 and, similarly, a clearance gap 2158 is present between the proximal leg 2132 of the staple 2130b and the distal sidewall of the proximal guide slot 2122. In addition, a clearance gap 2157 is present between the lateral side of the proximal leg 2132 and the lateral sidewall of the proximal guide slot 2122. Similar gaps can be found between the distal leg 2133 and the distal guide slot 2123. Lateral clearance gaps 2126, 2127 can also be provided between the base 2131 of the staple 2130b and the lateral sides of the central slot 2121. Such clearance gaps may be transient and the staple may contact one or more of the sidewalls nonetheless.

Figure 43:
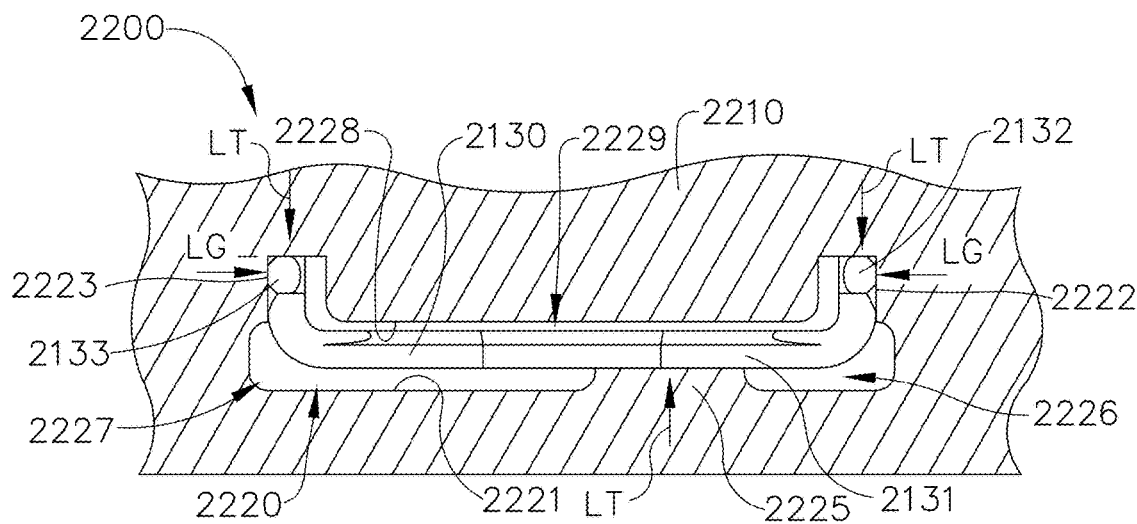
FIG. 43 is a cross-sectional plan view of a staple cavity configured to guide a staple in accordance with at least one embodiment.
Figure 44:
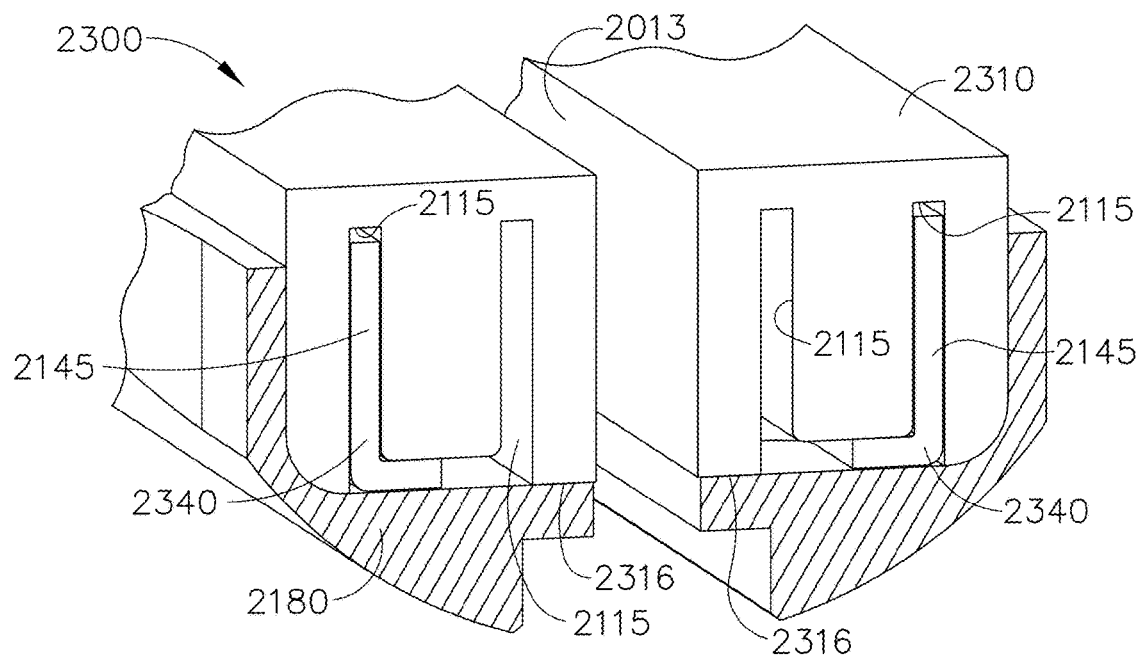
FIG. 44 is a cross-sectional perspective view of a staple cartridge assembly positioned in a jaw of a surgical stapling instrument in accordance with at least one embodiment illustrating a firing member positioned in a cartridge body of the staple cartridge assembly.

A staple cartridge 2200 is illustrated in FIG. 43. The staple cartridge 2200 is similar to the staple cartridges 2000, 2100 and the other staple cartridges disclosed herein in many respects. The staple cartridge 2200 comprises a cartridge body 2210 including staple cavities 2220 defined therein. Each of the staple cavities 2220 has a staple, such as staple 2130, for example, removably stored therein. Each staple cavity 2220 comprises a first guide slot 2222 configured to guide the leg 2132 of the staple 2130, a second guide slot 2223 configured to guide the leg 2133 of the staple 2130, and a central slot 2221. The guide slots 2222 and 2223 extend laterally from the central slot 2221 and the central slot 2221 includes an intermediate guide 2225 configured to guide the base 2131 of the staple 2130. The first guide slot 2222 is sized and configured such that the staple leg 2132 is closely received in a corner of the first guide slot 2222. Similarly, the second guide slot 2223 is sized and configured such that the staple leg 2133 is closely received in a corner of the second guide slot 2223. The intermediate guide 2225 is sized and configured to limit the lateral movement of the staple 2130 within the staple cavity 2220. Moreover, the intermediate guide 2225 is sized and configured to hold the staple legs 2132 and 2133 in the staple leg guide slots 2222 and 2223, respectively.

As discussed above, the intermediate guide 2225 is sized and configured to hold the staple legs 2132 and 2133 against the sidewalls of the guide slots 2222 and 2223, respectively. Such an arrangement creates lateral reaction forces, indicated as force vectors LT in FIG. 43, between the lateral sidewalls of the cavity 2220 and the staple 2130. Such lateral reaction forces generate friction forces between the sidewalls of the cavity 2220 and the staple 2130 when the staple 2130 is ejected from the cavity 2220. It should be understood that friction forces are a function of the surface area in which they are applied and, as such, the intermediate guide 2225 does not extend along the entire length of the central slot 2221. That said, the intermediate guide 2225 has a longitudinal length which is sufficient to control the orientation of the staple 2130 within the cavity 2220. Moreover, the intermediate guide 2225 has a sufficient vertical length sufficient to control the orientation of the staple 2130 during the firing stroke of the staple 2130. In at least one instance, the guide 2225 extends along the entire vertical depth of the cavity 2220.

The intermediate guide 2225 is flat and is configured to interface with a flat surface defined on the lateral side of the base 2131 of the staple 2130; however, any suitable arrangement could be utilized. In certain alternative embodiments, the intermediate guide 2225 comprises a resilient biasing member configured to apply a lateral biasing force to the base 2131 of the staple 2130, for example. In at least one instance, the resilient biasing member could comprise a cantilever spring, for example.

The staple cavity 2220 does not include a lateral guide positioned opposite the lateral intermediate guide 2225. In fact, a clearance gap 2229 is present between a lateral sidewall 2228 and the staple 2130.

Further to the above, referring again to FIG. 43, the staple 2130 is not positioned in the ends of the central slot 2221. More particularly, the central slot 2221 of the cavity 2220 comprises a proximal end 2226 and a distal end 2227 and the staple 2130 does not extend into either the proximal end 2226 or the distal end 2227. Rather, clearance gaps are present between the ends 2226, 2227 and the staple 2130. Such clearance gaps extend between the ends 2226, 2227 and the intermediate guide 2225. As a result, the ends 2226, 2227 of the staple cavity 2220 do not control the longitudinal position of the staple 2130. Instead, the staple leg guides 2222, 2223 control the longitudinal position of the staple 2130. In fact, the legs 2132 and 2133 of the staple 2130 can be biased inwardly by the staple leg guides 2222 and 2223, respectively. Such an arrangement creates longitudinal reaction forces, indicated as force vectors LG in FIG. 43.

As a result of the above, the staple cavity 2220 comprises three control points, or positions, in which the staple cavity 2220 controls the orientation of the staple 2130. These control points comprise discrete control positions with clearance gaps defined therebetween. Stated another way, the guides 2222, 2223, and 2225 triangulate the control of the staple 2130. Alternative embodiments are envisioned which comprise more than three control points. In any event, the control points provided by the staple leg guides 2222 and 2223 are defined in a first control plane. An intermediate control point provided by the intermediate guide 2225 is defined in a second control plane. The first control plane and the second control plane are parallel; however, alternative embodiments are envisioned in which the first control plane and the second control plane are not parallel. Moreover, the first control plane is aligned with, or adjacent to, the staple legs 2132 and 2133 of the staple 2130 and the second control plane is aligned with, or adjacent to, the base 2131 of the staple 2130.

Figure 65:
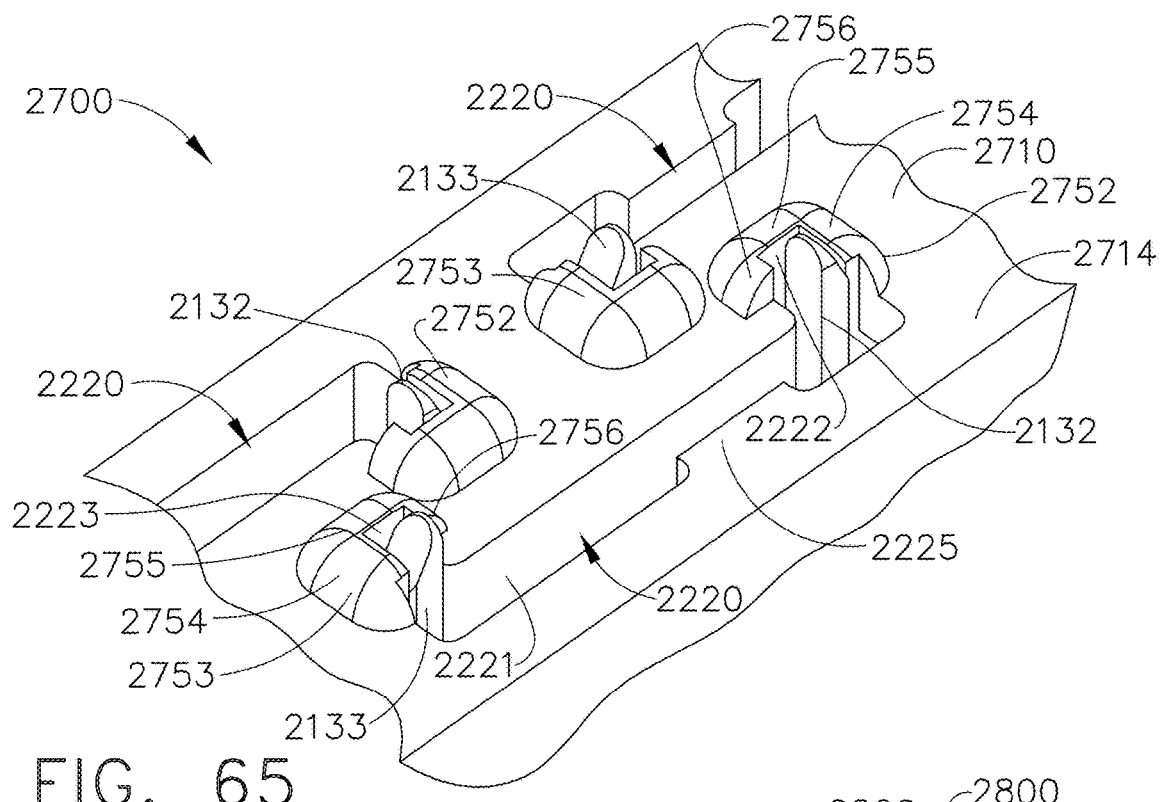
FIG. 65 is a partial perspective view of projections extending from a deck surface of a staple cartridge assembly in accordance with at least one alternative embodiment.

A staple cartridge 2700 is illustrated in FIG. 65. The staple cartridge 2700 comprises a cartridge body 2710 which includes a deck 2714 and a plurality of staple cavities 2220 defined in the deck 2714. Similar to the cartridge body 2110, the cartridge body 2710 includes projections 2752 and 2753 which extend above the deck 2714. The projections 2752 at least partially surround the staple leg guides 2222 of the staple cavities 2220 and the projections 2753 at least partially surround the staple leg guides 2223 of the staple cavities 2220. Similar to projections 2152, 2153, the projections 2752, 2753 each include an outside portion 2754 and a lateral portion 2755. The outside portions 2754 are positioned longitudinally with respect to the staple leg guides 2222 and 2223 while the lateral portions 2755 are positioned laterally with respect to the staple leg guides 2222 and 2223. Unlike the projections 2152, 2153, the projections 2752, 2753 each include an inner portion 2756 which are positioned longitudinally with respect to the staple leg guides 2222 and 2223. The inner portions 2756 are connected to the lateral portions 2755 and the lateral portions 2755 are connected to the outside portions 2754. Similar to the above, the projections 2752, 2753 extend the staple cavities 2220 above the deck 2714.

Figure 66:
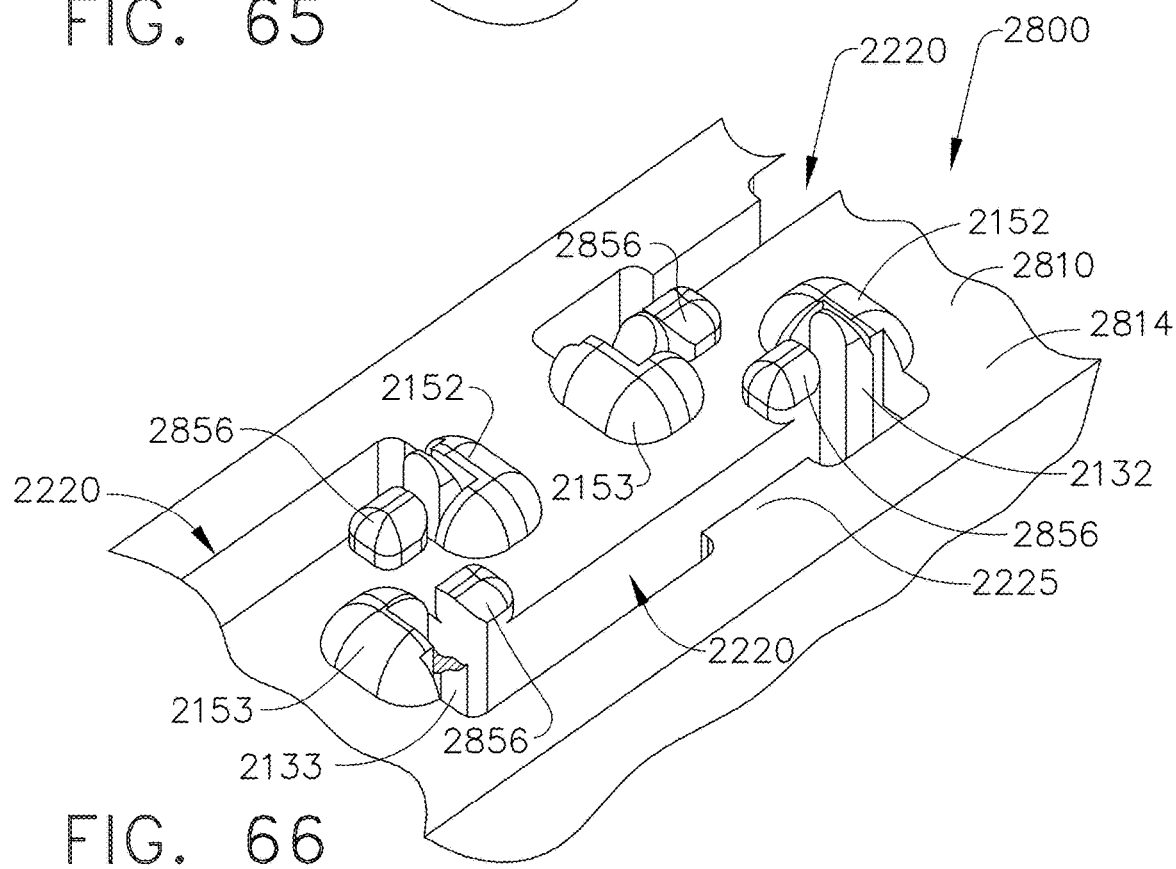
FIG. 66 is a partial perspective view of projections extending from a deck surface of a staple cartridge assembly in accordance with at least one alternative embodiment.

A staple cartridge 2800 is illustrated in FIG. 66. The staple cartridge 2800 comprises a cartridge body 2810 which includes a deck 2814 and a plurality of staple cavities 2220 defined in the deck 2814. Similar to the cartridge body 2110, the cartridge body 2810 includes projections 2152, 2153 which extend above the deck 2114. As outlined above, the projections 2152 at least partially surround the staple leg guides 2222 of the staple cavities 2220 and the projections 2753 at least partially surround the staple leg guides 2223 of the staple cavities 2220. Moreover, the cartridge body 2810 includes inner projections 2856 which are positioned longitudinally with respect to the staple leg guides 2222 and 2223. The inner projections 2856 are not connected to the projections 2152, 2153.

Figure 37:
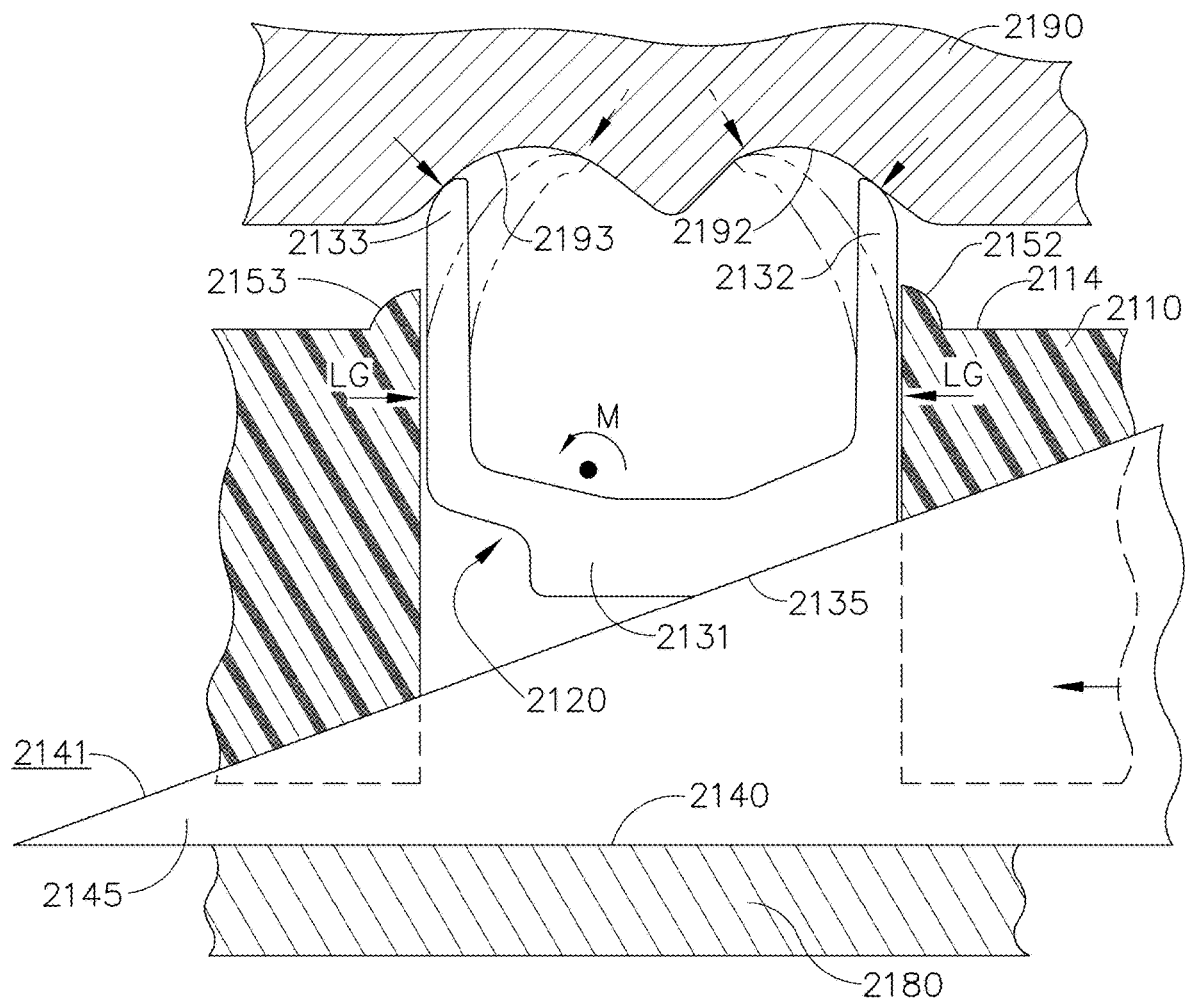
FIG. 37 is a partial cross-sectional view of the staple cartridge assembly of FIG. 35 illustrating a staple being deformed against an anvil by the firing member.

Referring again to FIG. 35, the staples 2130 are driven between unfired positions and fired positions by a firing member, such as sled 2140, for example. The sled 2140 comprises wedges 2145 which are configured to directly engage the staples 2130 and lift the staples 2130 toward an anvil, such as anvil 2190, for example, as illustrated in FIG. 37. The sled 2140 comprises a wedge 2145 for each longitudinal row of staples 2130; however, the sled 2140 may have any suitable number of wedges 2145. Each wedge 2145 comprises an angled drive surface 2141 which slides under the staples 2130 as the sled 2140 is advanced from the proximal end of the staple cartridge 2100 toward the distal end of the staple cartridge 2100. The base 2131 of each staple 2130 comprises an angled drive surface 2135 which is directly contacted by a drive surface 2141. Stated another way, each staple 2130 comprises its own integrally-formed driver having a drive surface 2135. The staples 2130 are comprised of metal and, as a result, the integrally-formed driver is also comprised of metal. That said, the staples disclosed herein can be comprised of any suitable material.

Further to the above, each drive surface 2141 comprises an initial, or distal, portion 2142, a second, or intermediate, portion 2143, and a third, or apex, portion 2144. The initial portion 2142 extends at a first angle and provides an initial contact point for the sled 2140 against a staple 2130 as the sled 2140 is moved distally. As the initial portion 2142 slides under the staple 2130, the staple 2130 is lifted upwardly within the staple cavity 2120. As the sled 2140 continues to move distally, the intermediate portion 2143 comes into contact with the staple 2130. The intermediate portion 2143 extends at a second angle which is different than the first angle. The first angle can be steeper than the second angle when it is desirable for there to be a quick initial upward displacement of the staple 2130 whereas the first angle can be shallower than the second angle when it is desirable to a provide a gradual initial upward displacement of the staple 2130. In either event, the staple 2130 contacts the anvil 2190 while the staple 2130 is being lifted upwardly by the intermediate portion 2143, as illustrated in FIG. 37; however, alternative embodiments are envisioned in which the staple 2130 contacts the anvil 2190 when the staple 2130 is being lifted upwardly by the initial portion 2142. In either event, the proximal leg 2132 of the staple 2130 contacts a proximal forming pocket 2192 defined in the anvil 2190 and the distal leg 2133 contacts a distal forming pocket 2193 defined in the anvil 2190. The forming pockets 2192 and 2193 are configured to bend the legs 2132 and 2133 inwardly to deform the staple 2130 and capture the tissue of a patient within the staple 2130. The apex 2144 of the drive surface 2141 slides under the staple 2130 to finish the forming process. The apex 2144 can comprise a peak of the drive surface 2141, a flat surface, and/or a surface which extends at a third angle which is different than the first angle and/or the second angle.

In various instances, each drive surface 2141 can comprise a portion which trails, or is positioned proximal to, the apex 2144 of the drive surface 2141. Such a trailing portion can be lower than the apex 2144, for example. Moreover, such a trailing portion can provide for a gradual decrease in forming pressure in the staples 2130, for example.

Figure 39:
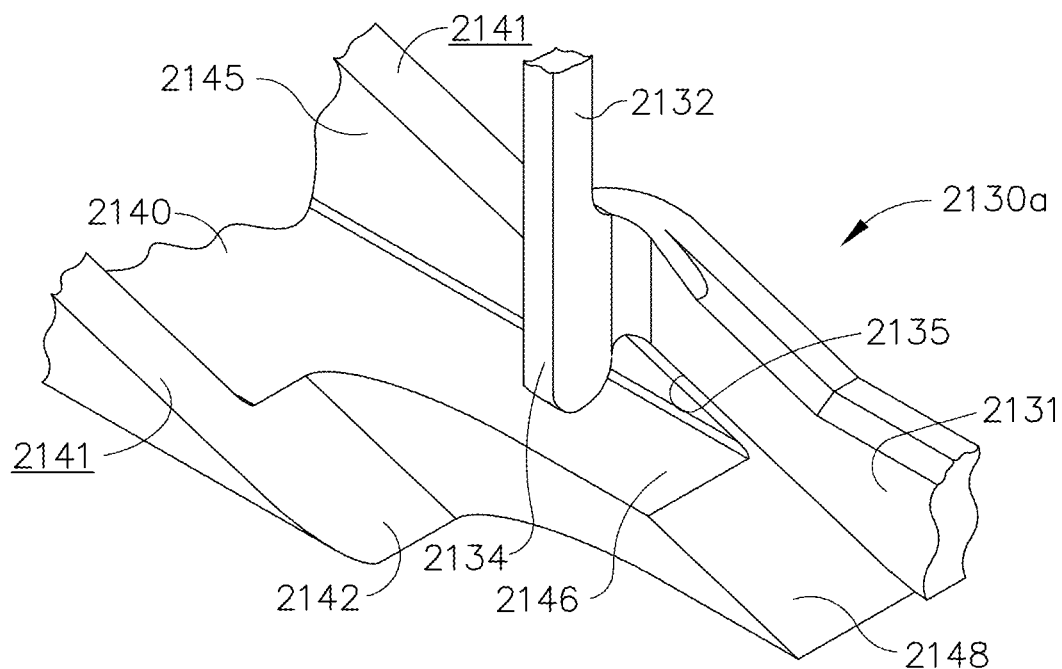
FIG. 39 is a partial perspective view of a staple being lifted by the firing member of the staple cartridge of FIG. 35.
Figure 41:
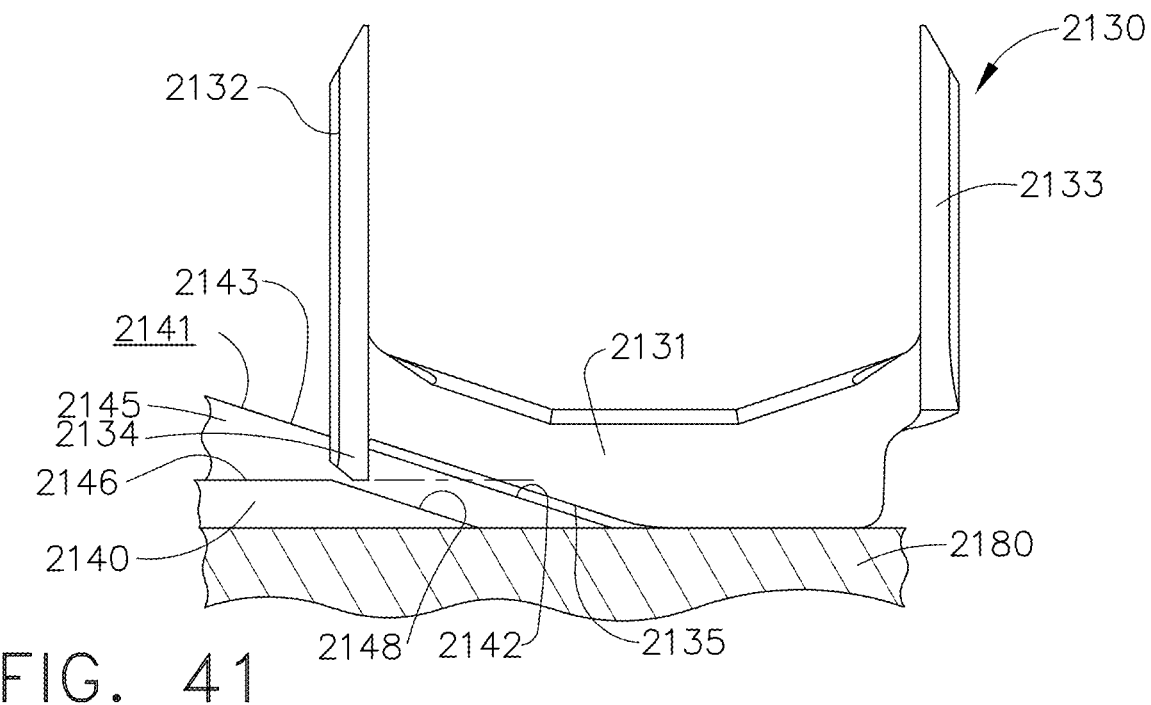
FIG. 41 is a diagram illustrating the staple of FIG. 39 in a level position.
Figure 42:
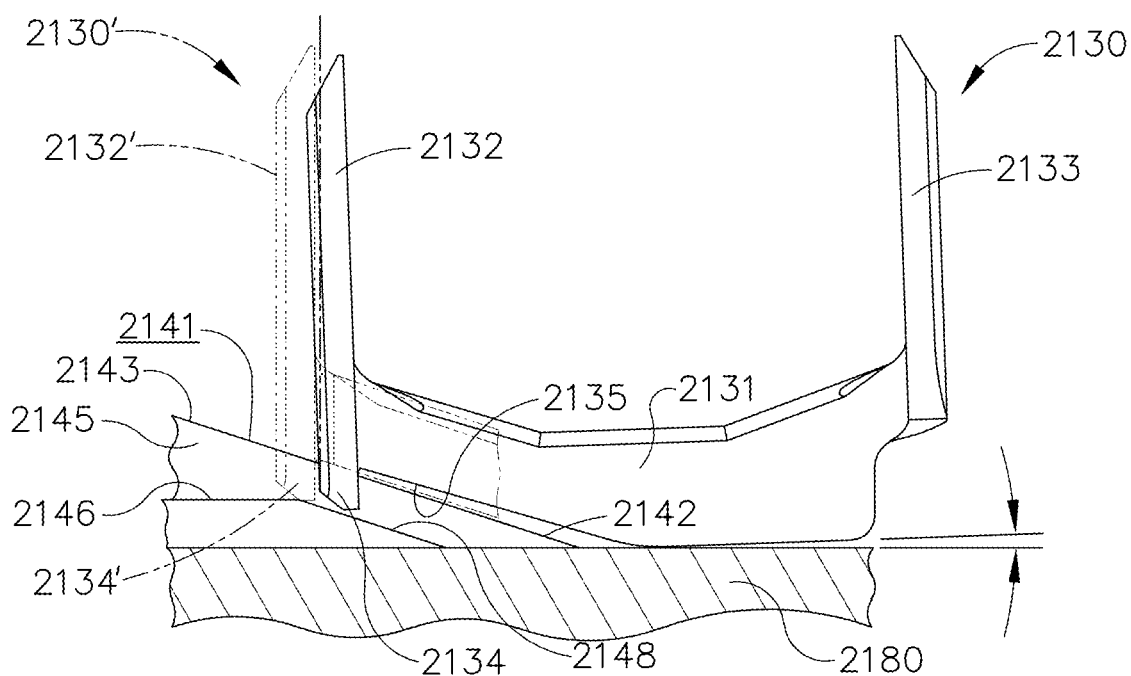
FIG. 42 is a diagram illustrating the staple of FIG. 39 in a crooked position.

Turning now to FIG. 39, the staple 2130 further includes a foot 2134 which extends downwardly from the proximal leg 2132. When the staple 2130 is in its proper orientation in its staple cavity 2120, as illustrated in FIG. 41, the foot 2134 is not contacted by the sled 2140. In such instances, an alignment plateau 2146 of the sled 2140 passes under the foot 2134. When the staple 2130 is not in its proper orientation in its staple cavity 2120, as illustrated in FIG. 42, the sled 2140 can contact the staple 2130 and re-orient the staple 2130. For the purpose of comparison, an improperly oriented staple 2130 and a properly oriented staple 2130' are both illustrated in FIG. 42. The sled 2140 comprises an angled alignment ramp 2148 which is configured to contact the foot 2134 and rotate the staple 2130 into is proper orientation. After the alignment ramp 2148 has properly oriented the staple 2130, the alignment plateau 2146 can slide underneath the foot 2134. As can be appreciated from FIG. 39, the alignment ramp 2148, the alignment plateau 2146, and the foot 2134 are arranged in an alignment plane which is aligned with the forming plane of the legs 2132 and 2133 of the staple 2130. The alignment plane is adjacent to a lifting plane which includes the forming surface 2141 of the sled 2140 and the base 2131 of the staple 2130.

A staple cartridge assembly 2300 is illustrated in FIGS. 44-48. The staple cartridge assembly 2300 is similar to the staple cartridge 2000, 2100, 2200, and the other staple cartridges disclosed herein in many respects. The staple cartridge 2300 comprises a cartridge body 2310 and sleds 2340 which are configured to eject staples removably stored in the cartridge body 2310. Similar to sled 2140, sleds 2340 comprise staple forming ramps 2145. The ramps 2145 are slidably positioned in longitudinal slots 2115 defined in the cartridge body 2110 which are aligned with the lifting portions, or planes, of the staples. Notably, as discussed in greater detail below, the slots 2115 have an open end defined in the bottom 2316 of the cartridge body 2310.

Figure 48:
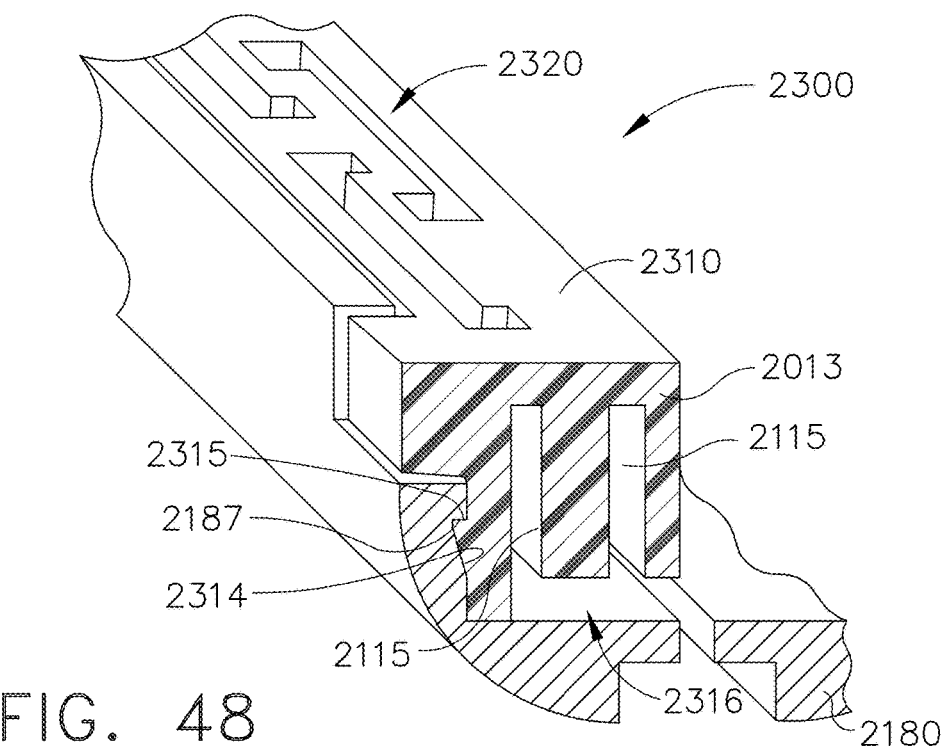
FIG. 48 is a partial cross-sectional perspective view of the staple cartridge assembly of FIG. 44 illustrating a retention feature configured to releasably hold the staple cartridge assembly in the jaw of the surgical stapling instrument.

Further to the above, the staple cartridge assembly 2300 does not include a cover extending around the bottom 2316 of the cartridge body 2310. Referring primarily to FIG. 48, the cartridge body 2310 is directly positioned against the jaw 2180 of the stapling instrument. In embodiments where a staple cartridge is not readily removable from the jaw of a stapling instrument and not readily replaceable with another staple cartridge, the absence of a bottom cover is not necessarily problematic as the jaw 2180 can prevent the staples from falling out of the bottom of the staple cavities 2120 and/or the sleds 2340 from falling out of the bottom of the longitudinal slots 2115. The staple cartridge assembly 2300 is, however, replaceable and, even though it does not include a bottom cover, the staple cartridge assembly 2300 includes features which keep the staples and the sleds 2340 from falling out of the bottom 2316 of the cartridge body 2310, which are described in greater detail further below. Such features could be adapted to any of the staple cartridges disclosed herein.

Figure 45:
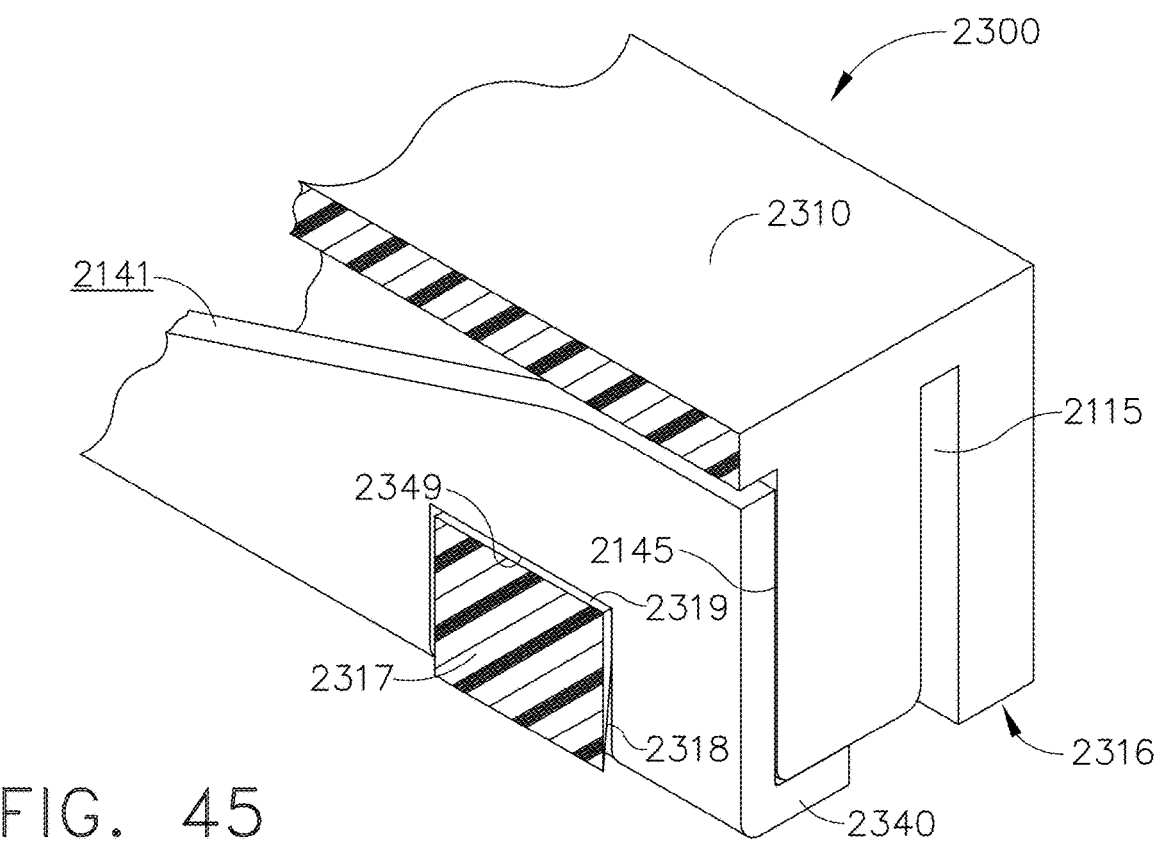
FIG. 45 is a partial cross-sectional perspective view of the staple cartridge assembly of FIG. 44 illustrating a retention feature configured to hold the firing member in the cartridge body when the staple cartridge assembly is not positioned in the jaw of the surgical stapling instrument.
Figure 46:
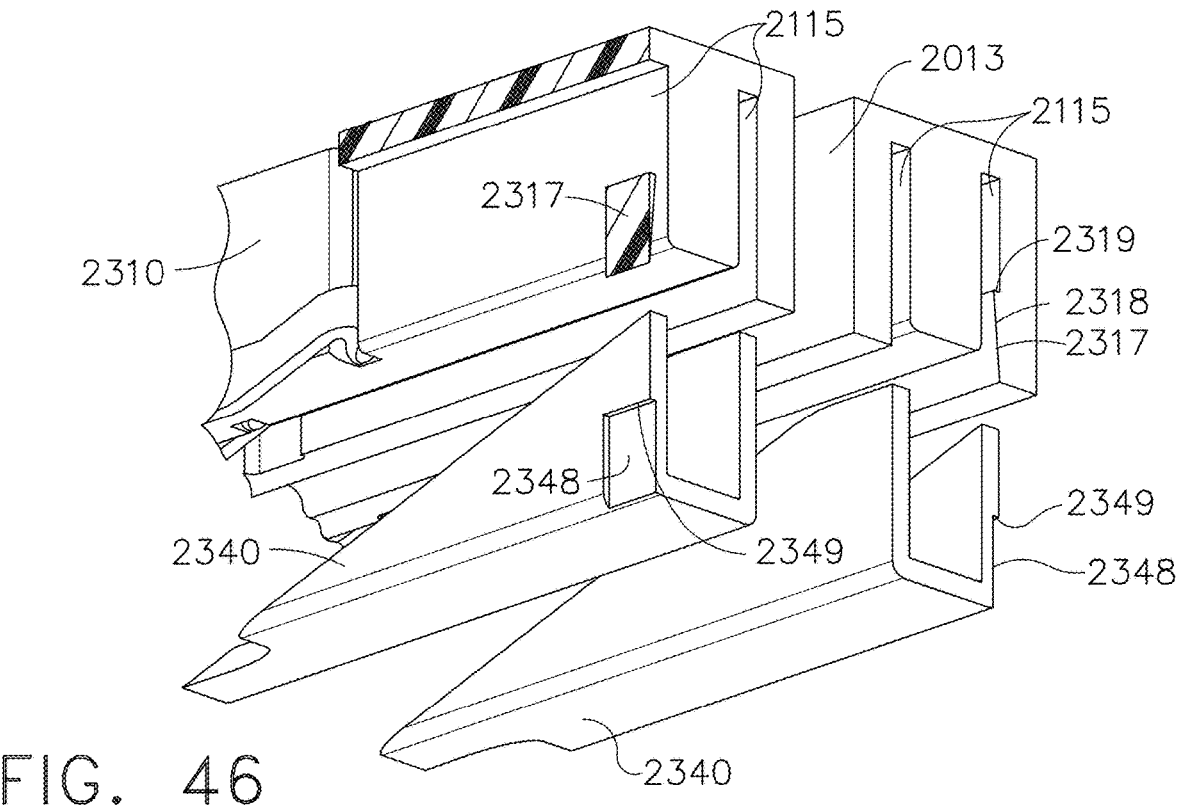
FIG. 46 is a partial cross-sectional exploded view of the staple cartridge assembly of FIG. 44.
Figure 47:
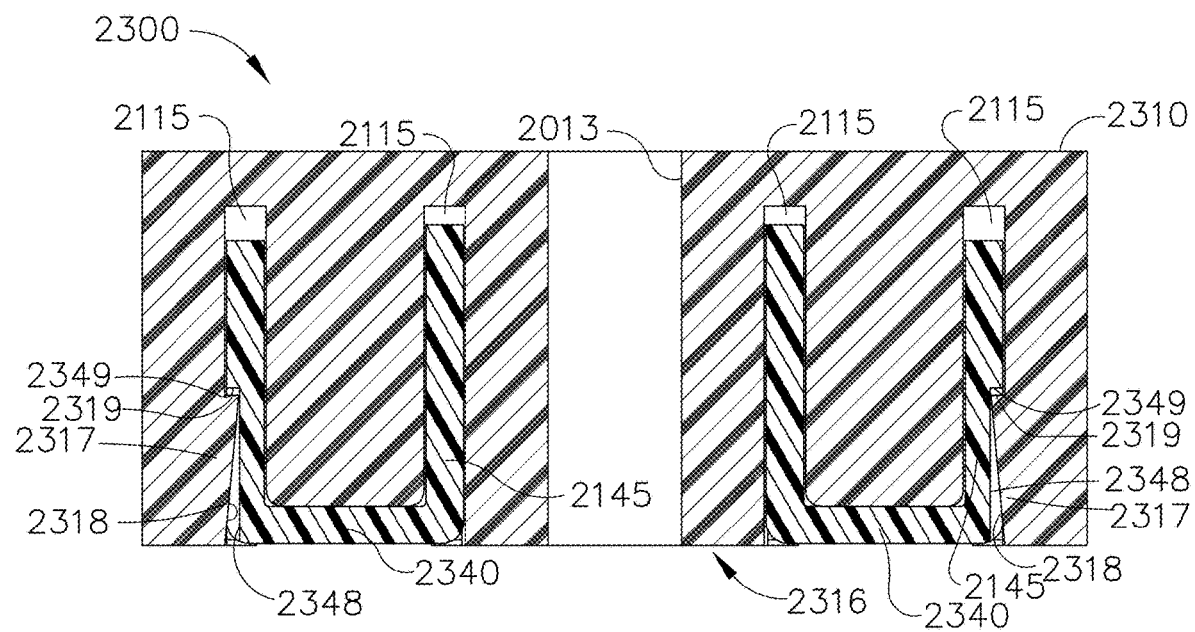
FIG. 47 is a partial cross-sectional end view of the staple cartridge assembly of FIG. 44.

Referring primarily to FIGS. 45-47, the cartridge body 2310 includes retention features configured to hold the sleds 2340 therein. For example, the cartridge body 2310 includes proximal retention features 2317 which are configured to hold the sleds 2340 in the longitudinal slots 2115 when the sleds 2340 are in their proximal, or unfired, positions. The sleds 2340 are in their unfired positions when the staple cartridge assembly 2300 is inserted, or loaded, into the jaw 2180 and, as a result, the proximal retention features 2317 retain the sleds 2340 in the cartridge body 2310 when the cartridge assembly 2300 is being handled by a clinician. Each retention feature 2317 includes an angled surface 2318 and a shoulder 2319. Each sled 2340 includes a corresponding recess 2348 configured to receive an angled surface 2318 and, in addition, a corresponding shoulder 2349 which can be aligned with and/or contact a shoulder 2319 of the retention feature 2317. When the sleds 2340 are inserted into the slots 2115, referring to FIG. 46, the ramps 2145 and/or the sidewalls of the cartridge 2310 can flex to permit the sleds 2340 to slide relative to the angled surfaces and then resiliently snap back to their original positions once the shoulders 2349 of the sleds 2340 have become aligned with the shoulders 2319 of the cartridge body 2310, as illustrated in FIG. 45. The retention features 2317 are also configured to prevent the sleds 2340 from sliding proximally out of the longitudinal slots 2115.

As a result of the above, the proximal retention features 2317 prevent the sleds 2340 from falling out of the cartridge body 2310 when a clinician is handling the staple cartridge assembly 2300. When the sleds 2340 are advanced distally to fire the staples, the sleds 2340 are no longer aligned with the proximal retention features 2317. At such point, however, the staple cartridge assembly 2300 is already in the jaw 2180 and sled retention features are no longer needed. That said, the cartridge body 2310 can include additional retention features which can hold the sleds 2340 in the cartridge body 2310 regardless of the position of the sleds 2340. Such retention features could be configured to hold the sleds 2340 in the cartridge body 2310 when the sleds 2340 are in their distal, or fully fired, positions, for example.

Figure 49:
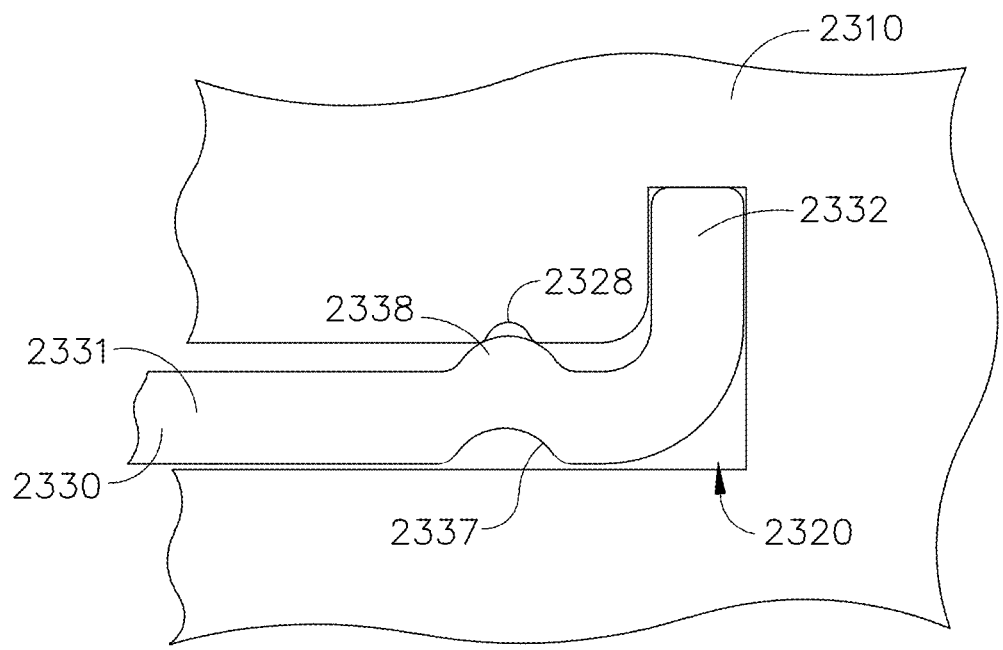
FIG. 49 is a partial plan view of a staple positioned in a staple cavity of a staple cartridge assembly in accordance with at least one embodiment.
Figure 50:
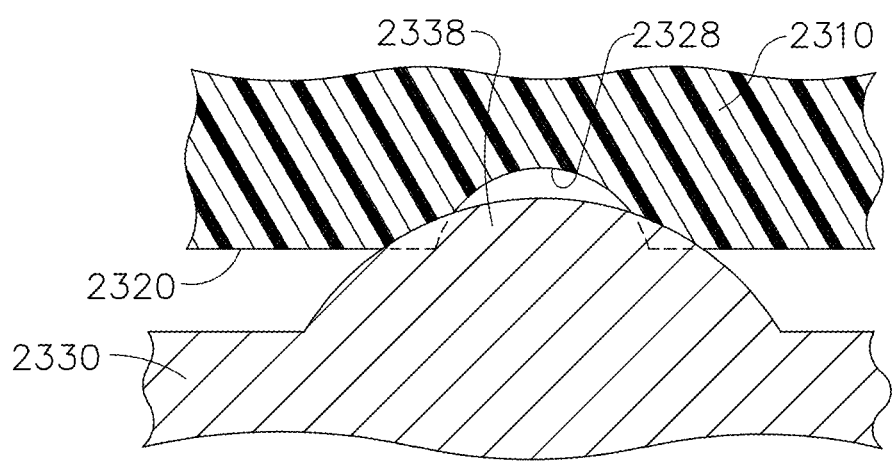
FIG. 50 is a detail view of a retention feature configured to releasably hold the staple in the staple cartridge assembly of FIG. 49.

Further to the above, the staples of the staple cartridges disclosed herein can include one or more features configured to hold the staples in the staple cavities of the staple cartridge. Turning now to FIGS. 49 and 50, a staple 2330 includes a base 2331 and one or more staple legs 2332 extending from the base 2331. The staple 2330 is removably stored in a staple cavity 2320 in the cartridge body 2310, for example. The base 2331 comprises a protrusion 2338 extending therefrom which is engaged with a sidewall of the staple cavity 2320. The interaction between the protrusion 2338 and the staple cavity sidewall keeps the staple 2330 from falling out of the bottom 2316 of the cartridge body 2310. The interaction between the protrusion 2338 and the staple cavity sidewall comprises an interference fit; however, such an interference fit does not prevent the sleds 2340 from ejecting the staples 2330 from the staple cavities 2320. The protrusion 2338 can be formed in the base 2331 during a stamping process, for example. The stamping process can form the protrusion 2338 by creating a dent 2337 in the opposite side of the base 2331. The staple cavity 2320 includes a vertical groove 2328 which is aligned with the protrusion 2338. The groove 2328 increases the contact area between the sidewall of the staple cavity 2320 and the protrusion 2338. In addition, the groove 2328 can control the orientation of the staple 2330 within the staple cavity 2320. Alternative embodiments are envisioned which do not comprise the groove 2328.

Figure 51:
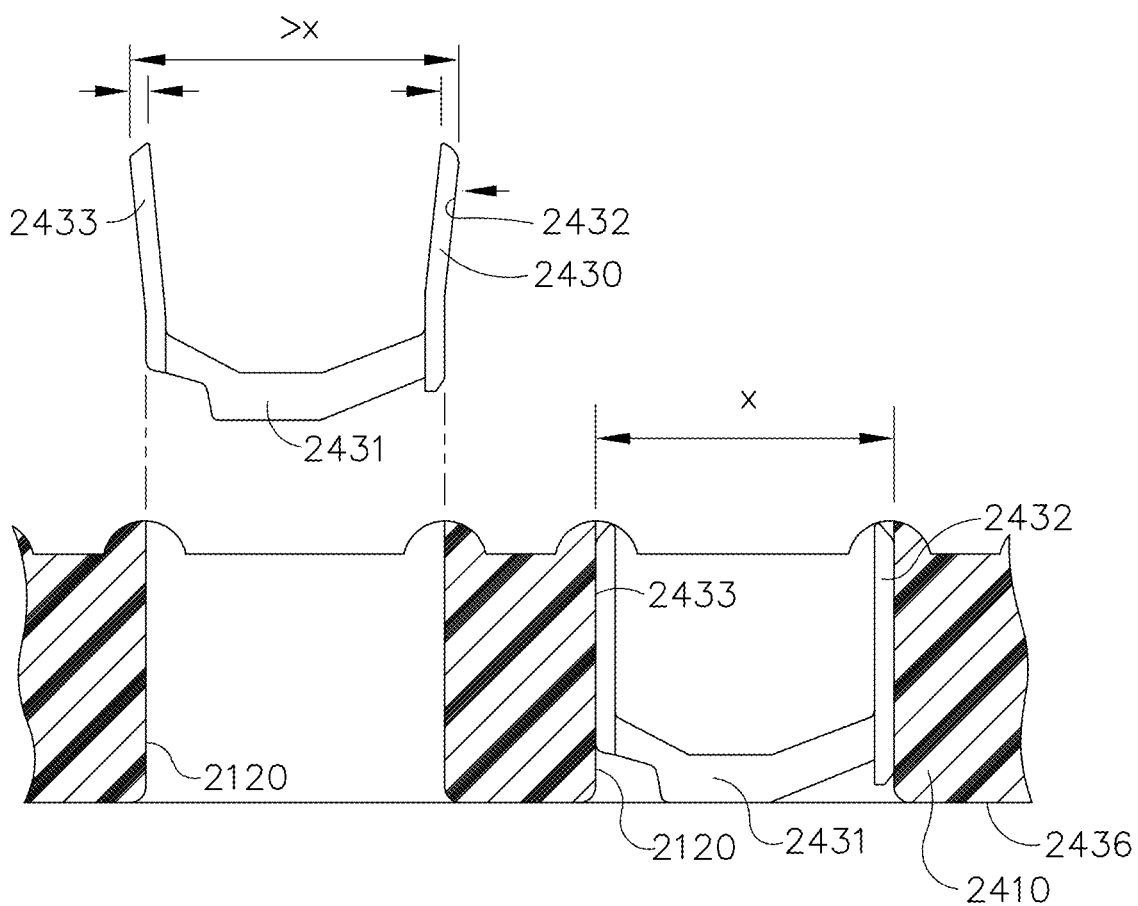
FIG. 51 is a partial cross-sectional elevational view of a staple cartridge assembly in accordance with at least one embodiment.
Figure 52:
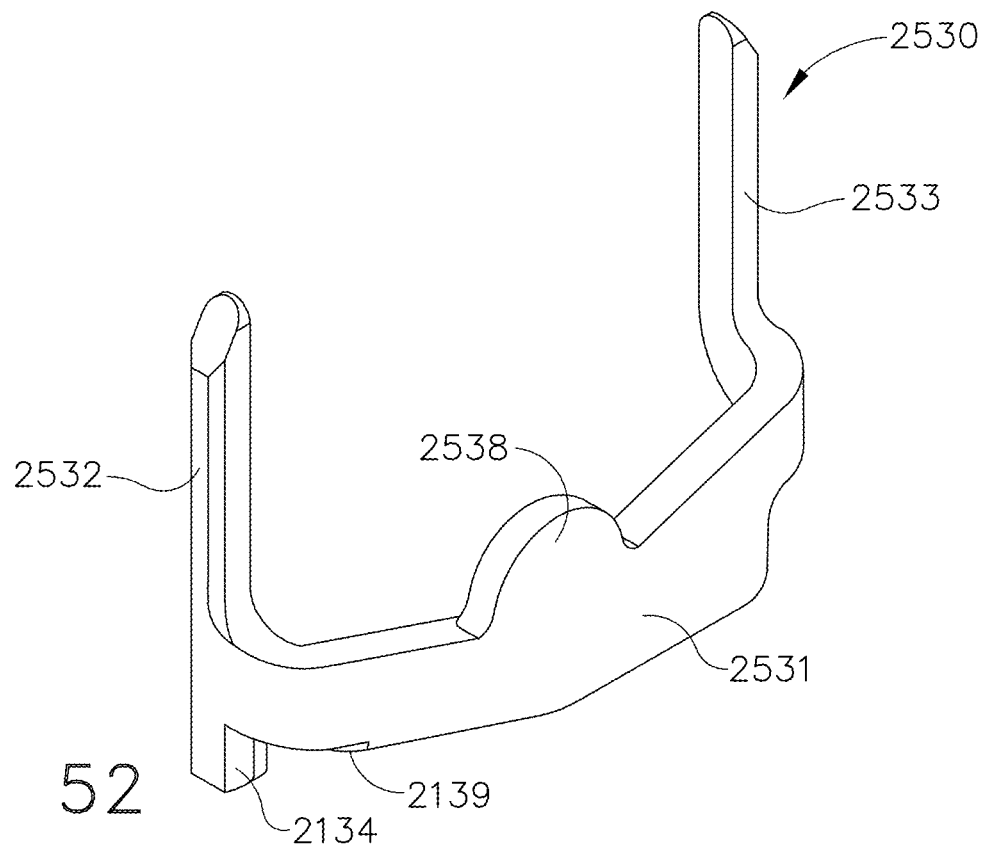
FIG. 52 is a perspective view of a staple in accordance with at least one embodiment.
Figure 53:
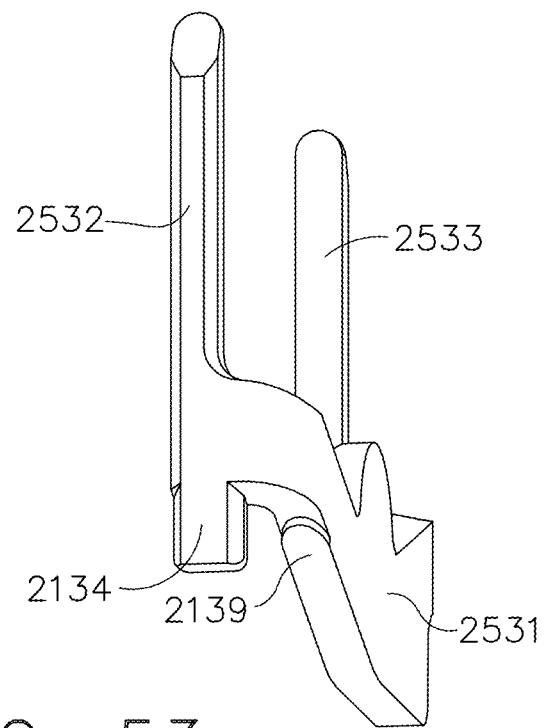
FIG. 53 is a bottom perspective view of the staple of FIG. 52.
Figures 54, 55:
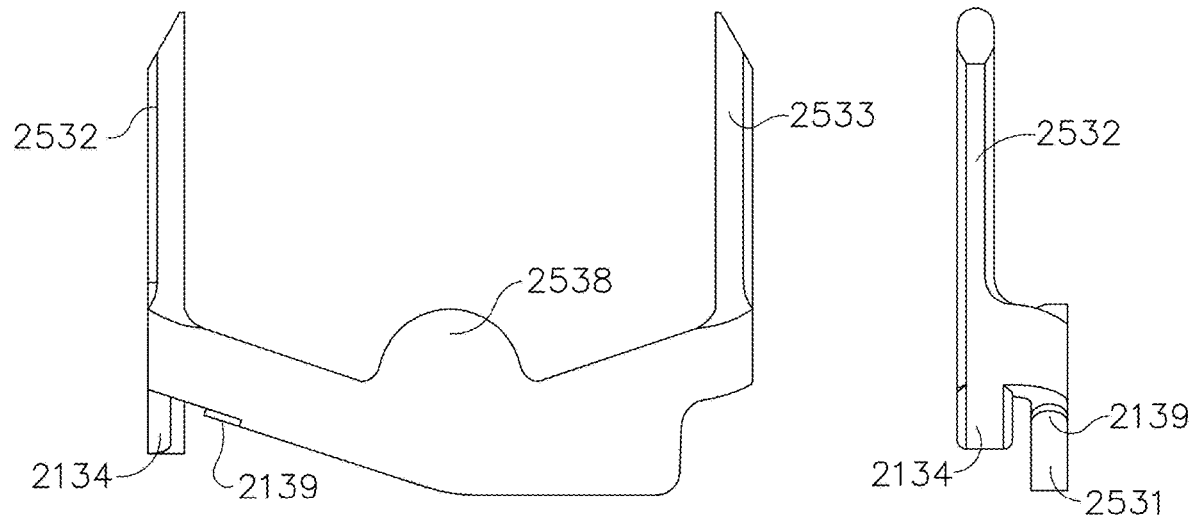
FIG. 54 is a front elevational view of the staple of FIG. 52.
FIG. 55 is a side elevational view of the staple of FIG. 52.
Figure 56:
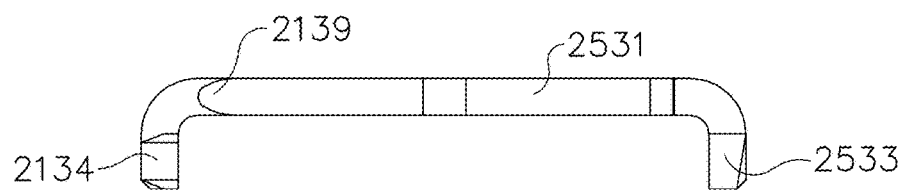
FIG. 56 is a bottom view of the staple of FIG. 52.
Figure 62:
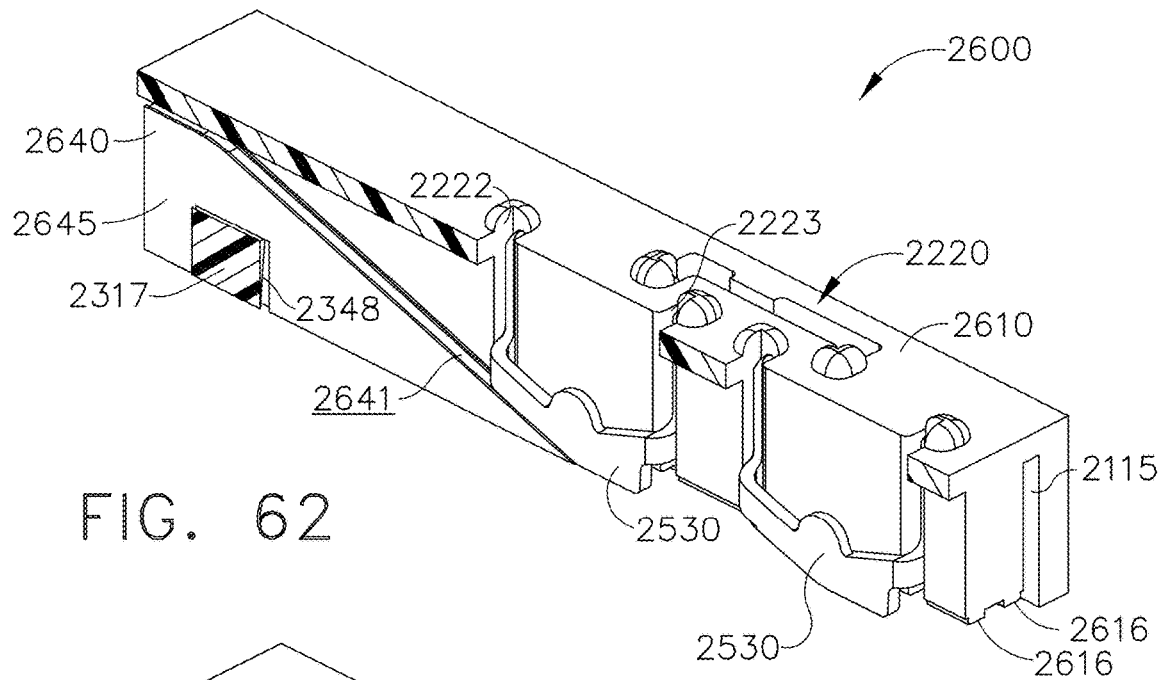
FIG. 62 is a partial cross-sectional perspective view of the staple cartridge assembly of FIG. 58.
Figure 63:
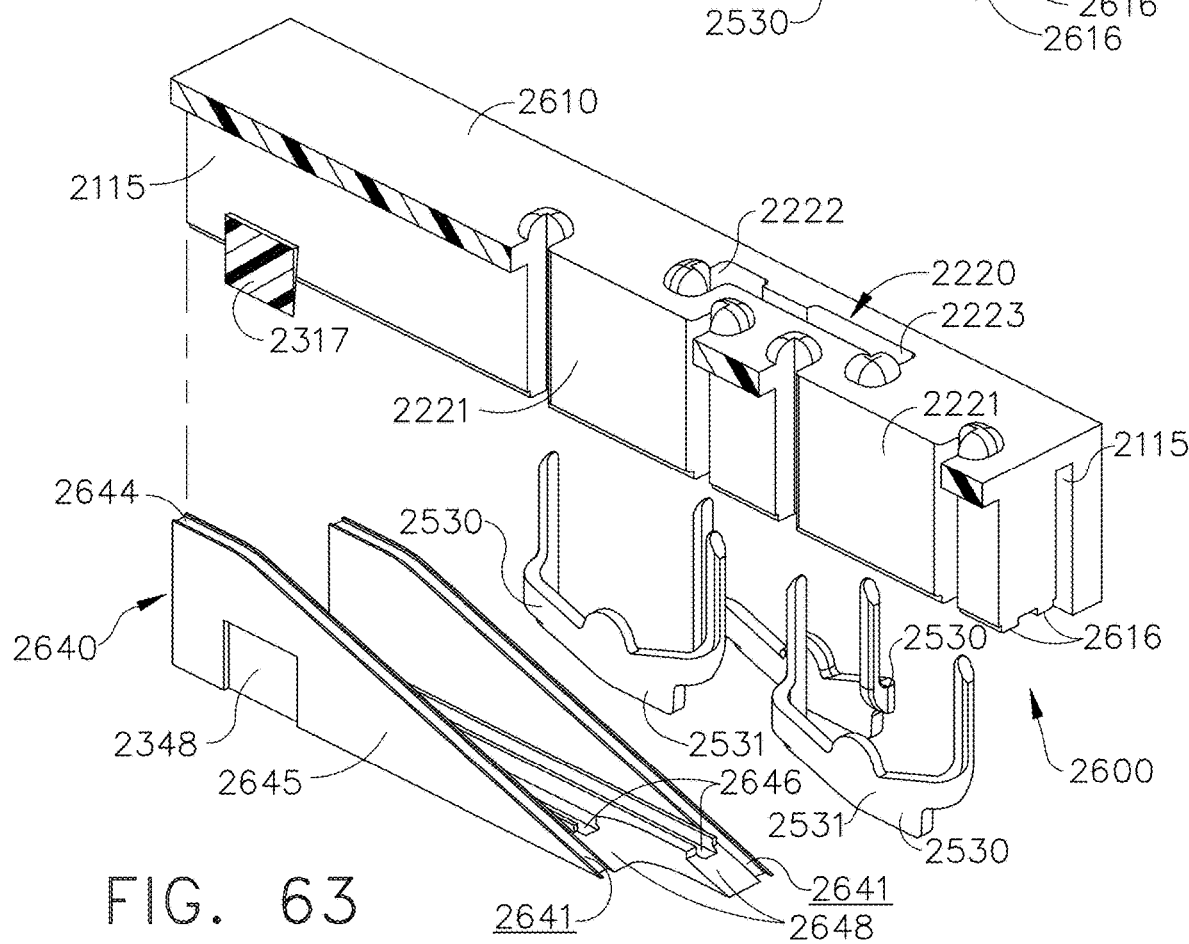
FIG. 63 is a partial exploded view of the staple cartridge assembly of FIG. 58.

In addition to or in lieu of the above, the staples stored in the staple cartridges disclosed herein can include staple legs which are resiliently engaged with the sidewalls of their staple cavities. Turning now to FIG. 51, a staple 2430 can include a base 2431 and staple legs 2432 and 2433 extending from the base 2431. The staples 2430 are similar to the staples 2130, 2330, and/or the other staples disclosed herein in many respects. A staple cartridge body 2410, for example, can include a plurality of staple cavities 2120 defined therein and a staple 2430 positioned in each staple cavity 2120. FIG. 51 depicts a staple 2430 positioned inside a cavity 2120 and a staple 2430 positioned outside a staple cavity 2120 of the cartridge body 2430. When the staples 2430 are not positioned in the staple cavities 2120, the staple legs 2432, 2433 do not extend in parallel directions; rather, they extend outwardly away from each other. When the staples 2430 are positioned in the staple cavities 2120, they are flexed inwardly by the sidewalls of the staple cavities 2120. Stated another way, the staple legs 2432, 2433 are resiliently biased against the sidewalls of the staple cavities and, owing to this biased engagement, the staples 2430 are inhibited from falling out of the bottom 2436 of the cartridge body 2410. As illustrated in FIG. 51, the distance between the staple legs 2432, 2433 when the staples 2130 are positioned in the staple cavities 2120 is X while the distance between the staple legs 2432, 2433 when the staples 2130 are not positioned in the staple cavities is larger than X.

In various embodiments, a cartridge body can include one or more shoulders which are configured to keep the staples stored therein from falling out of the bottom of the cartridge body. The shoulders can at least partially extend underneath the staples.

In certain embodiments, the cartridge body of a staple cartridge assembly can be comprised of plastic and can be formed during an injection molding process, for example. The injection mold can include two halves which are movable toward and away from each other. The interface between the injection mold halves is often called a parting line and it is frequent that flashing, or seepage of the plastic between the mold halves, can occur at the parting line. In at least one embodiment, the parting line of an injection mold can be defined at the interfaces between the deck of the staple cartridge and the staple cavities defined in the deck. As a result of the above, plastic flashing can occur around the perimeter of the staple cavities. Such flashing can releasably hold the staples in the staple cartridge.

Referring again to FIG. 48, the cartridge body 2310 is configured to directly engage the jaw 2180. The jaw 2180 comprises one or more retention shoulders 2315 defined therein. The cartridge body 2310 comprises corresponding retention shoulders 2187 which co-operate with the retention shoulders 2315 to releasably retain the cartridge body 2310 in the jaw 2180. The cartridge body 2310 and/or the jaw 2180 further comprise ramp surfaces 2314 which are configured to facilitate the insertion of the cartridge body 2310 into the jaw 2180. As a result of the above, the cartridge body 2310 can have a snap-fit relationship with the jaw 2180. The snap-fit relationship can be overcome by prying the cartridge body 2310 out of the jaw 2180 such that the staple cartridge assembly 2300 can be replaced.

A staple 2530 is illustrated in FIGS. 52-56. The staple 2530 is similar to the staples 2130, 2330, 2340, and/or the other staples disclosed herein in many respects. The staple 2530 comprises a base 2531 and legs 2532 and 2533 extending from the base 2531. The staple 2530 also includes a projection 2538 extending upwardly from the base 2531. The projection 2538 is aligned with the staple driving plane which includes the base 2531 and is not aligned with tissue capture plane including the staple legs 2532 and 2533. The projections 2538 can compress the tissue outside of the staple capture plane.

A staple cartridge assembly 2600 is illustrated in FIGS. 57-64. The staple cartridge 2600 comprises a cartridge body 2610 including a plurality of staple cavities 2220 defined therein. The staple cartridge 2600 further comprises a staple 2530 positioned in each staple cavity 2220 and sleds 2640 configured to eject the staples 2530 from the staple cavities 2220. The sleds 2640 are similar to the sleds 2140 in many respects. Each sled 2640 comprises a plurality of ramps 2645 wherein each ramp 2645 comprises a drive surface 2641 configured to slide under the staples 2530 and lift the staples 2530 within the staple cavities 2220. Each drive surface 2641 includes an inclined surface 2643 bounded by lateral sidewalls 2649 which define a guide channel that aligns the staples 2530 with respect to the drive surfaces 2641 and/or the staple cavities 2220. The guide channel is configured to receive the bases 2531 of the staples 2530 between the sidewalls 2649 and orient the staples 2530 laterally as the sled 2640 is advanced distally. Such lateral re-alignment is apparent upon comparing FIGS. 58 and 59. Referring again to FIGS. 52-56, each staple 2530 comprises a guide feature 2139 defined on the bases 2531 thereof. The guide feature 2139 of each staple 2530 comprises a curved end, for example, which is configured to interact with the lateral sidewalls 2649 of the guide channels and adjust the lateral position of the staples 2530. In various other embodiments, the guide features 2139 can comprise any suitable configuration.

In addition to or in lieu of the above, referring primarily to FIG. 60, the sleds 2640 comprise guide channels 2646 which are configured to receive the downwardly depending feet 2134 of the staples 2530 and orient the staples 2530 with respect to the drive surfaces 2641 and/or the staple cavities 2220. Each guide channel 2646 comprises a ramp portion 2648 and lateral sidewalls. The guide channels 2646 are configured to receive the bases 2531 of the staples 2530 between the sidewalls of the channels 2646 and orient the staples 2530 laterally as the sled 2640 is advanced distally. Referring primarily to FIG. 61, each foot 2134 comprises lead-in, or beveled, surfaces 2137 which are configured to interact with the sidewalls of the channels 2646 to guide the staples 2530 into the channels 2646. That said, the feet 2134 can comprise any suitable geometry which facilitates the entry of the staples 2530 into the channels 2646. The reader should appreciate that, as the staples 2530 are driven upwardly within the staple cavities 2220 by the drive surfaces 2641, the feet 2134 of the staples 2530 lift out of the channels 2646. By the time that the staples 2530 are being formed by the apexes 2644 of the drive surfaces 2641, the feet 2134 are no longer positioned in the channels 2646.

Figure 64:
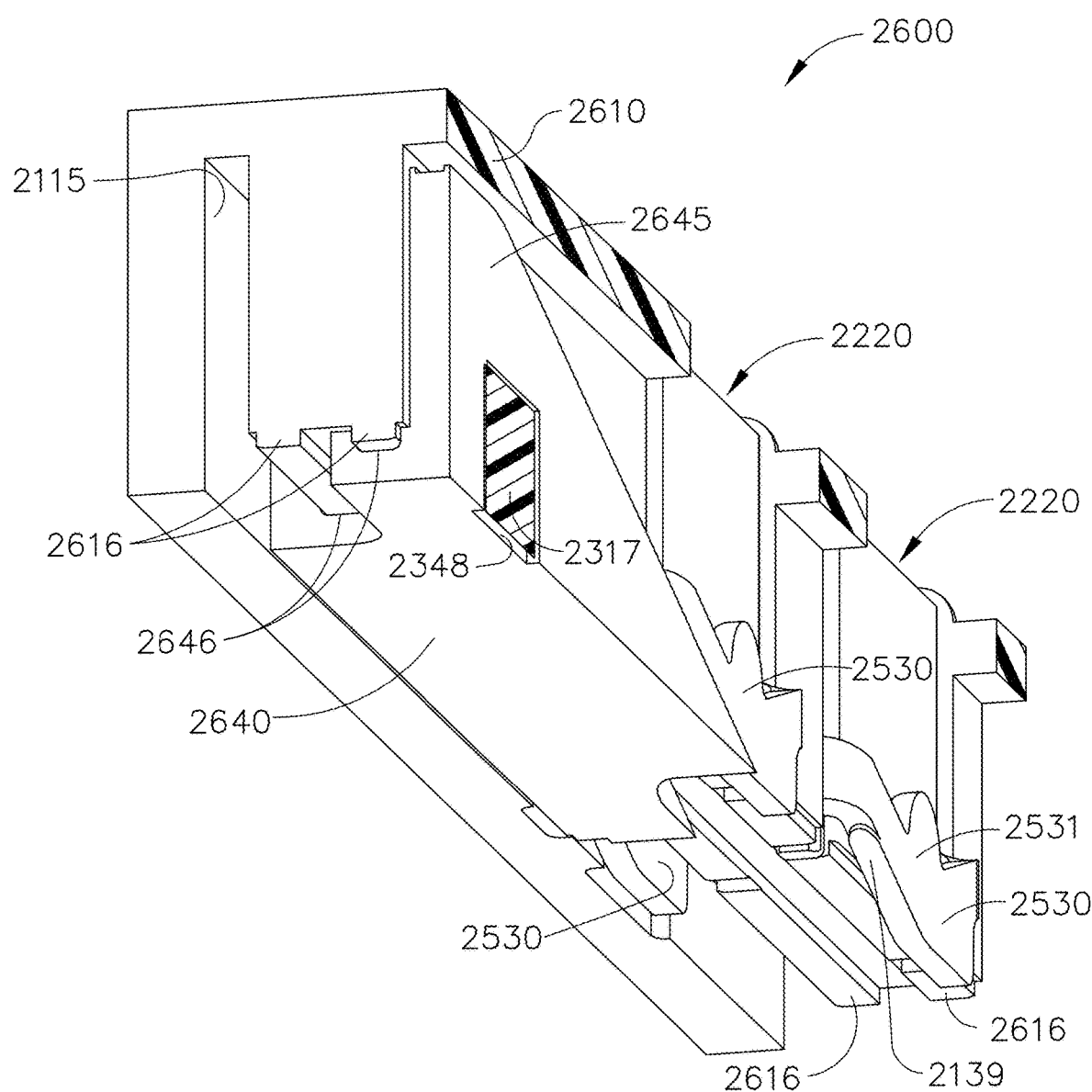
FIG. 64 is a partial bottom cross-sectional perspective view of the staple cartridge assembly of FIG. 58.

Referring primarily to FIGS. 58, 59, and 64, the channels 2646 can also align the sleds 2640 with respect to the cartridge body 2610. More particularly, the cartridge body 2610 further comprises longitudinal rails 2616 extending downwardly into the channels 2646. The rails 2616 are closely received in the channels 2646 to limit or prevent lateral movement between the sleds 2640 and the cartridge body 2610 while permit the longitudinal movement of the sleds 2640 needed to fire the staples 2530 as outlined above. The foot 2134 of each staple 2530 is configured to properly orient the staple 2530 within its staple cavity 2220 in the event that the staple 2530 is misoriented within the staple cavity 2220.

Figures 69, 70:
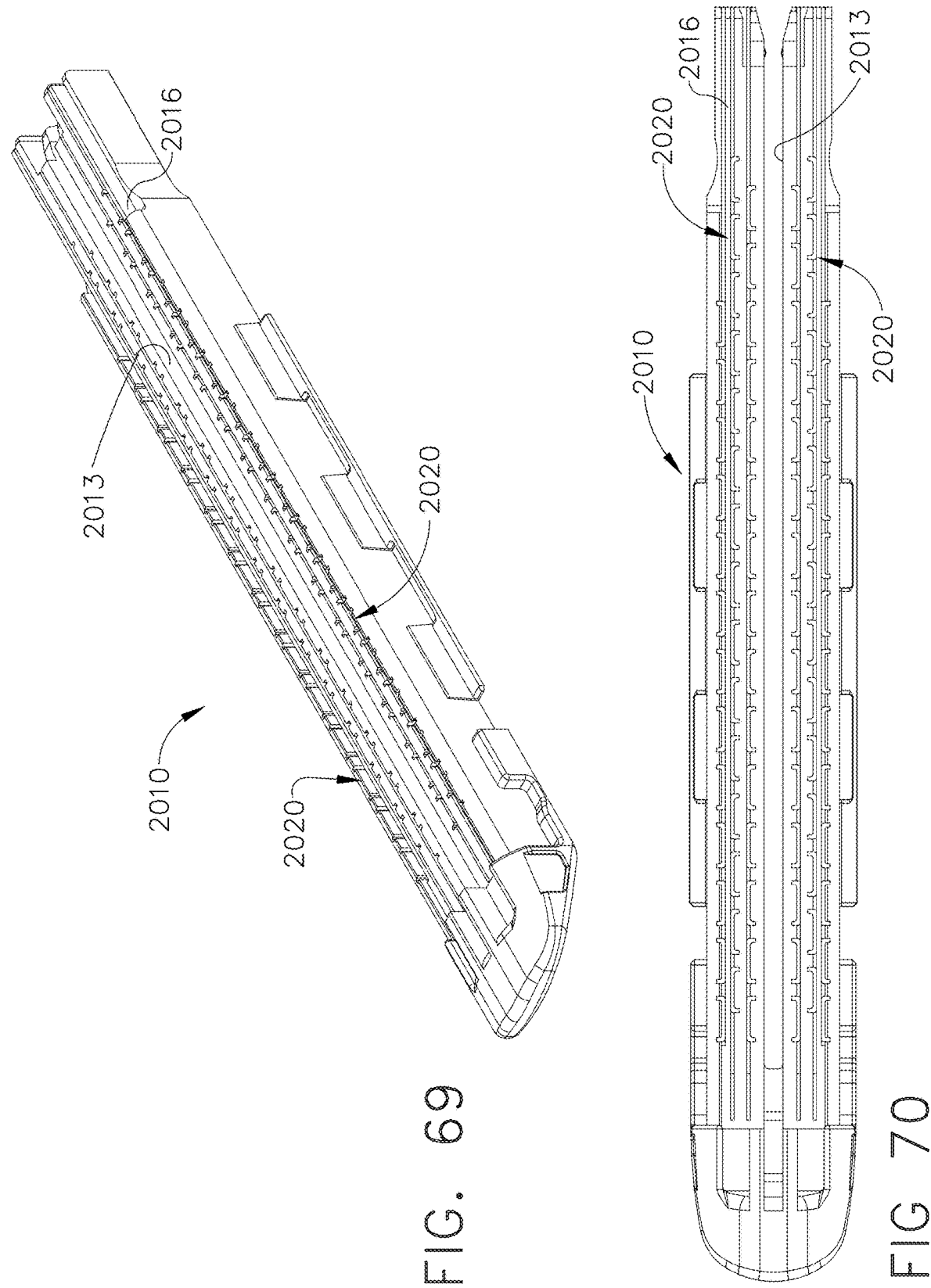
FIG. 69 is a bottom perspective view of the cartridge body of the staple cartridge assembly of FIG. 32.
FIG. 70 is a bottom view of the cartridge body of FIG. 32.

The arrangements disclosed herein allow for a staple cartridge to be more compact than previous staple cartridges. Among other things, the staple cartridges disclosed herein that do not utilize staple drivers between the firing member and the staples, i.e., driverless staple cartridges, allow the staple cartridges to have a shorter overall height. Similarly, the staple cartridges that do not include a bottom cover also allow the staple cartridges to have a shorter overall height. Driverless staple cartridges can also allow smaller staple cavities to be utilized. Turning now to FIGS. 67 and 68, a cartridge body 2910 includes staple cavities 2920 and a longitudinal slot 2013 defined therein. FIGS. 67 and 68 show the bottom 2916 of the cartridge body 2910 and the bottom openings of the staple cavities 2920. The reader should appreciate that the staple cavities 2920 are sized and configured to receive staple drivers for driving the staples out of the cartridge body 2910. Turning now to FIGS. 69 and 70 which depicts the bottom 2016 of the cartridge body 2010, the staple cavities 2020 of the cartridge body 2010 are smaller than the staple cavities 2920. As the reader will recall, drivers are not positioned in the staple cavities 2020 and, as a result, the size of the staple cavities 2020 can be reduced. FIG. 71 compares the bottom 2916 of the cartridge body 2910 to the bottom 3016 of an alternative embodiment of a cartridge body 3010. As can be seen in FIG. 71, the cartridge body 3010 includes longitudinal rows of staple cavities 3020 which are much narrower than the longitudinal rows of staple cavities 2920. In various instances, such narrower staple cavities can permit the center lines of the longitudinal rows of staple cavities to be closer to one another. Turning now to FIG. 72, a staple cartridge body 3110 includes longitudinal rows of staple cavities 3120a, 3120b, and 3120c defined in a deck 3114 of the cartridge body 3110 which are positioned closer together than would be permitted in embodiments which use staple drivers to lift the staples within the cartridge body.

Figure 73:
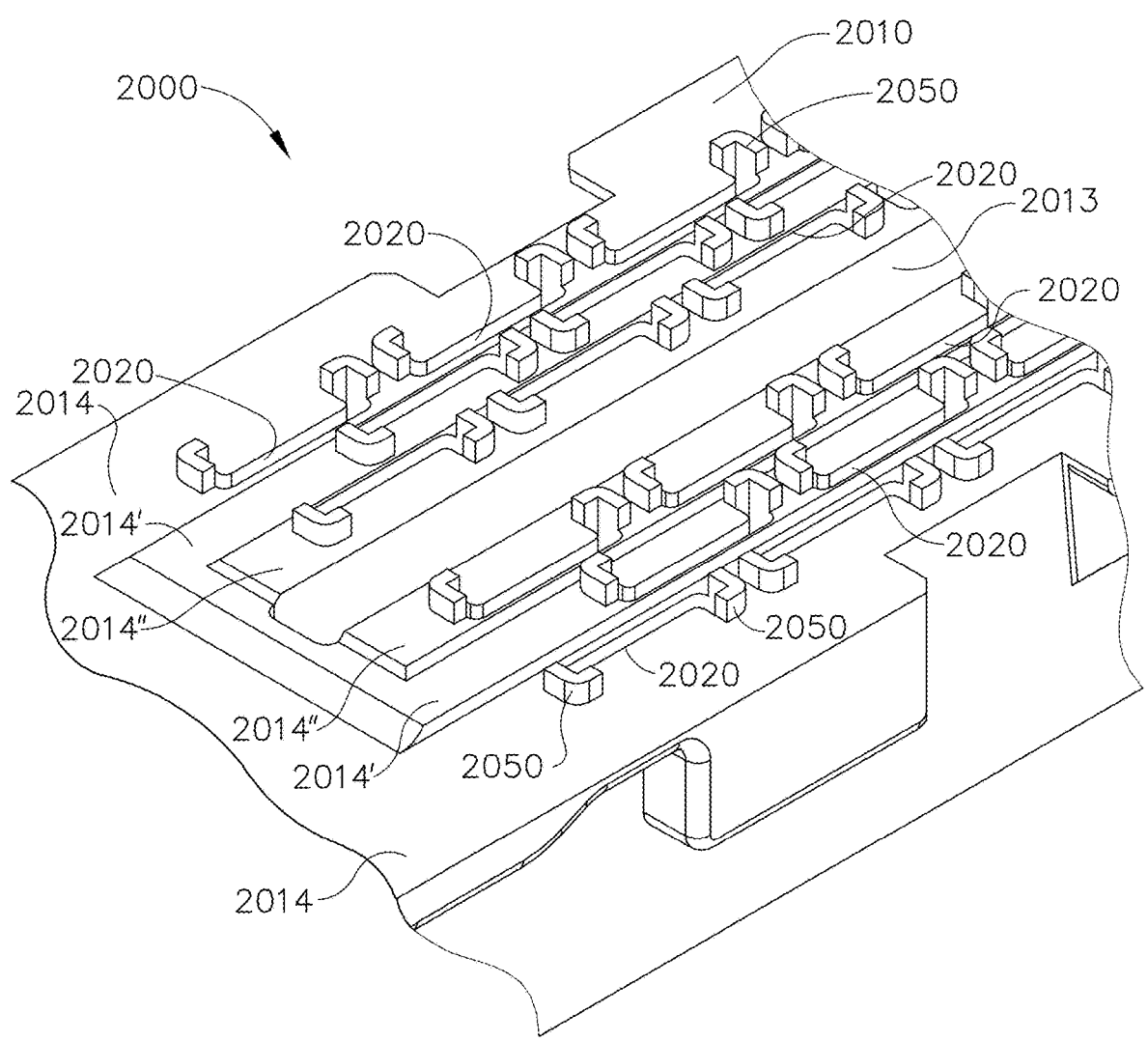
FIG. 73 is a partial perspective view of the staple cartridge of FIG. 32.
Figure 77:
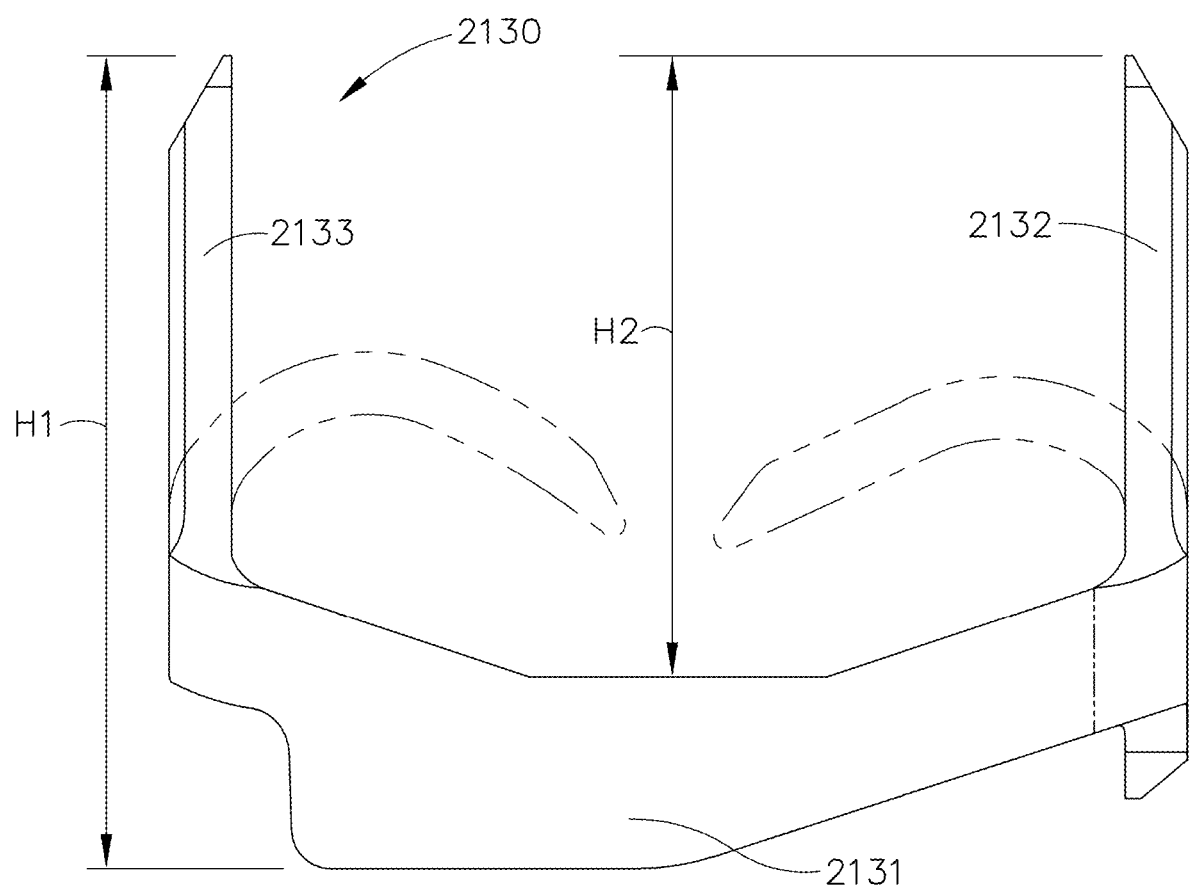
FIG. 77 illustrates a staple of the staple cartridge of FIG. 32 being deformed.

The various embodiments of the staple cartridge assemblies disclosed herein can have any suitable number of staples and/or any suitable size of staples. In certain instances, all of the staples stored in the staple cartridge assembly 2000 (FIG. 73) have the same, or at least substantially the same, size. Referring to FIG. 77, each staple 2130 in the staple cartridge 2000 comprises an unformed, or unfired, overall height H1 defined between the bottom of the base 2131 and the tips of the staple legs 2132, 2133. Similarly, each staple 2130 comprises a tissue capture area defined between the top of the base 2131 and the tips of the staple legs 2132, 2133 which has the same height H2 when the staples 2130 are in their unformed height.

In contrast to the above, a first group of staples stored in the staple cartridge 2000 can have a first unformed height H1 and a second group of staples can have a second unformed height H1 which is different than the first unformed height H1. Also in contrast to the above, a first group of staples stored in the staple cartridge 2000 can have a first tissue capture height H2 and a second group of staples can have a second tissue capture height H2 which is different than the first tissue capture height H2.

The first group of staples can be positioned in a first longitudinal row of staple cavities 2120 while the second group of staples can be positioned in a second longitudinal row of staple cavities 2120. In at least one instance, the first row of staple cavities 2120 can be adjacent the knife slot 2013 in the step 2014" of the cartridge body 2010 while the second row of staple cavities 2120 can be adjacent the first row of staple cavities 2120 in the step 2014' of the cartridge body 2010. In at least one such instance, the first unformed height H1 is shorter than the second unformed height H1, for example.

Further to the above, a third group of staples stored in the staple cartridge 2000 can have a third unformed height H1 which is different than the first unformed height H1 and/or the second unformed height H1. The third group of staples can be positioned in a third longitudinal row of staple cavities 2120. In at least one instance, the third row of staple cavities 2120 can be adjacent the second row of staple cavities 2120 in the deck 2014 of the cartridge body 2010. In at least one such instance, the second unformed height H1 is shorter than the third unformed height H1, for example. In addition to or in lieu of the above, the third group of staples can have a third tissue capture height H2 which is larger than the second tissue capture height H2.

In various embodiments, the first group of staples, the second group of staples, and/or the third group of staples can be deformed to the same overall formed height. Alternatively, the first group of staples can be deformed to a first formed height, the second group of staples can be deformed to a second formed height, and/or the third group of staples can be deformed to a third formed height. In such instances, the first group of staples can apply a larger pressure to the tissue than the second group of staples and, similarly, the second group of staples can apply a larger pressure to the tissue than the third group of staples.

Figure 74:
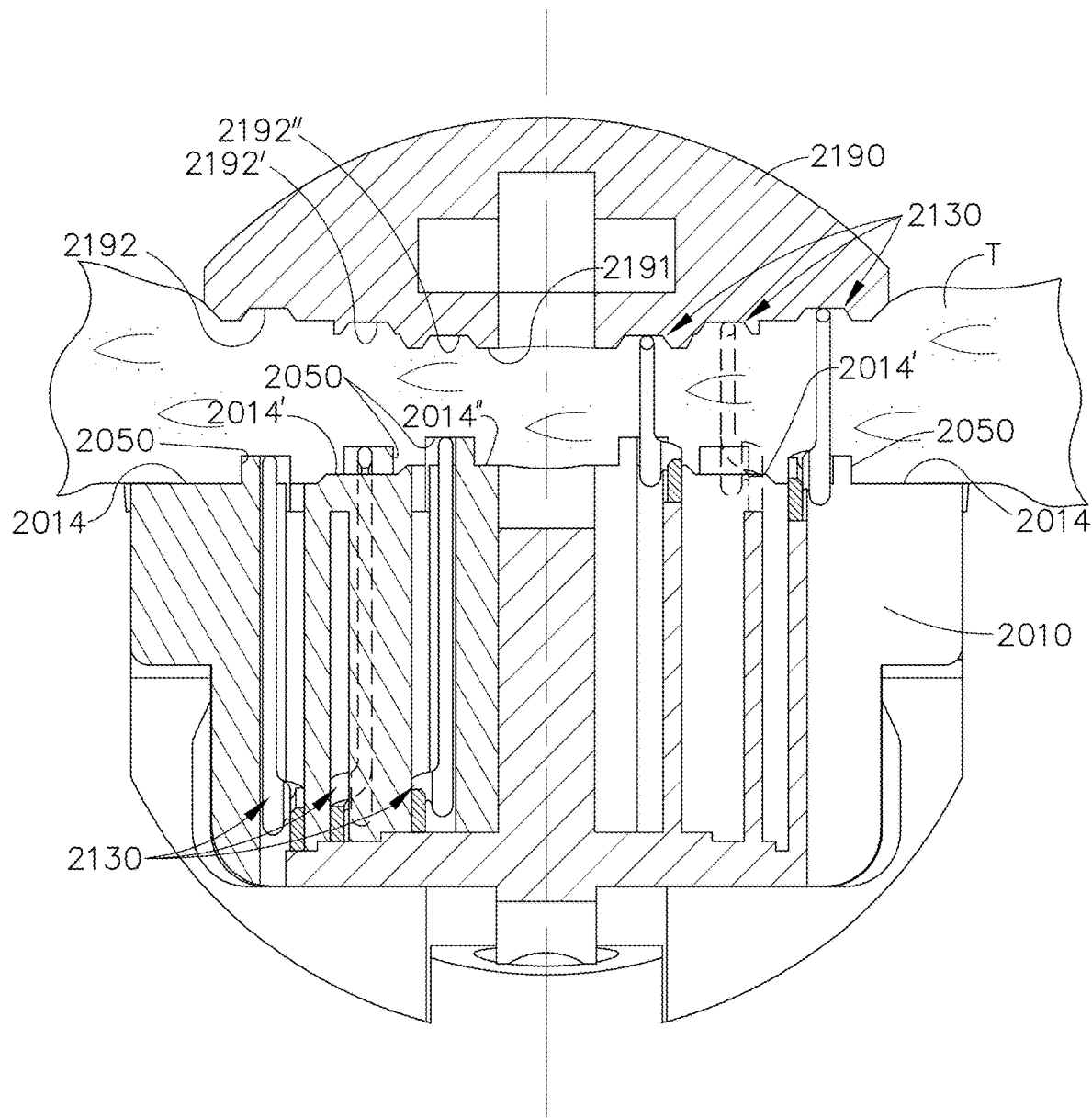
FIG. 74 is a cross-sectional view of the staple cartridge of FIG. 32 and the anvil of FIG. 37 illustrating certain staples in an unfired position and certain staples in a fired position.
Figure 75:
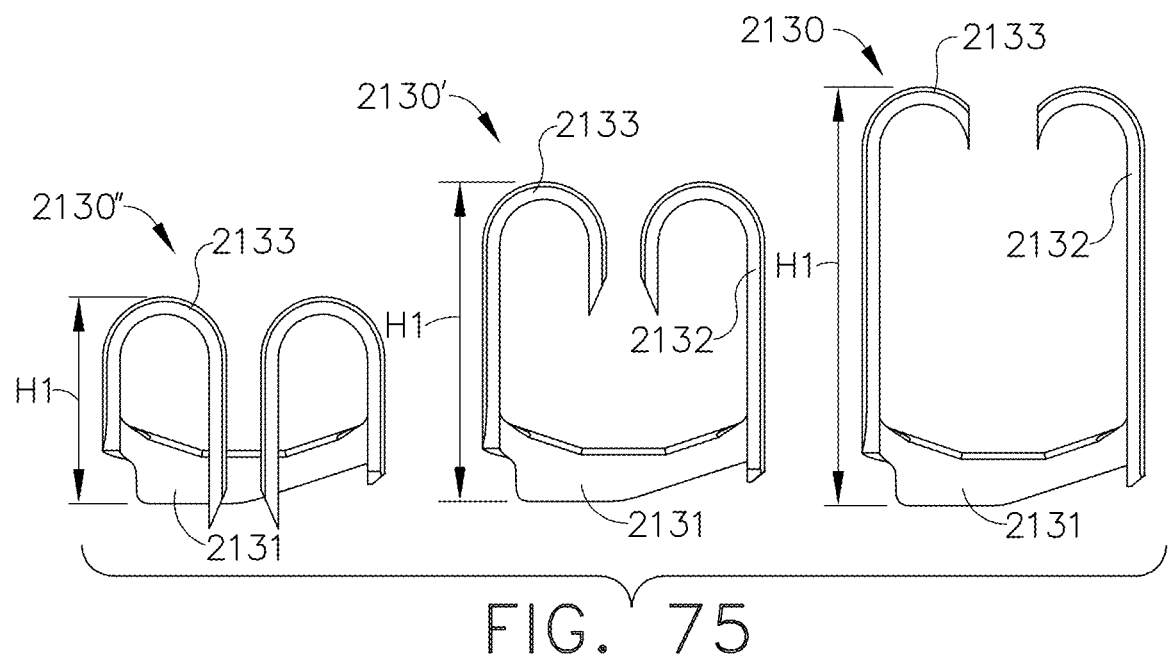
FIG. 75 illustrates the staples of the staple cartridge of FIG. 32 deformed to three different heights.
Figure 76:
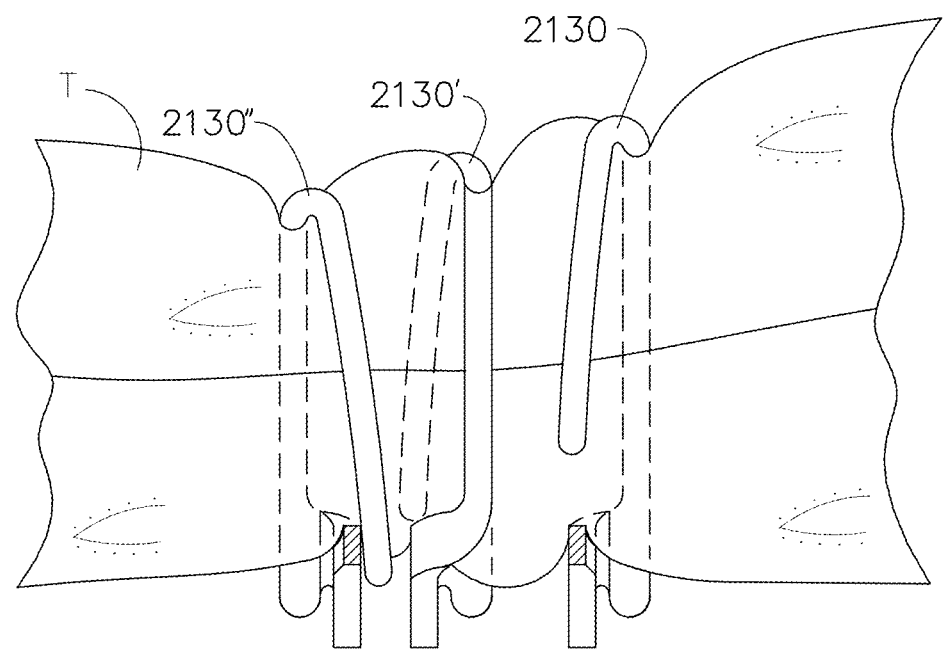
FIG. 76 illustrates the staples of the staple cartridge of FIG. 32 implanted in the tissue of a patient.

Turning now to FIGS. 74-76, staples having the same unformed height can be deformed to different formed heights. For example, a first longitudinal row of staples, represented by staples 2130", can be deformed to a first formed height, a second longitudinal row of staples, represented by staples 2130', can be deformed to a second formed height, and/or a third row of staples, represented by staples 2130, can be deformed to a third formed height. The first formed height is shorter than the second formed height, and the second formed height is shorter than the third formed height, for example. In such instances, the first group of staples can apply a larger pressure to the tissue than the second group of staples and, similarly, the second group of staples can apply a larger pressure to the third group of staples.

Figure 78:
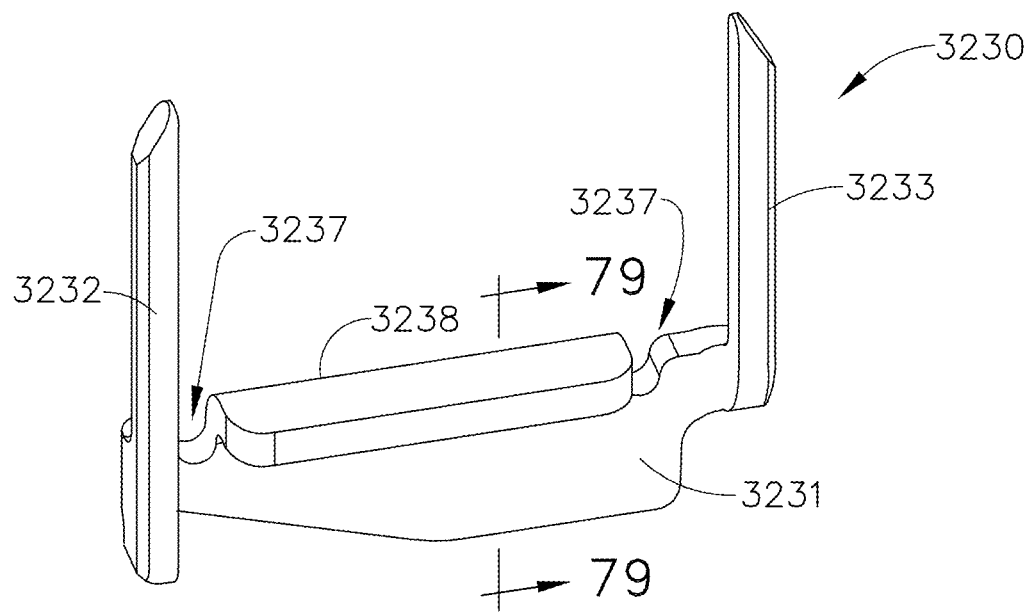
FIG. 78 is a perspective view of a staple in accordance with at least one embodiment.
Figure 79:
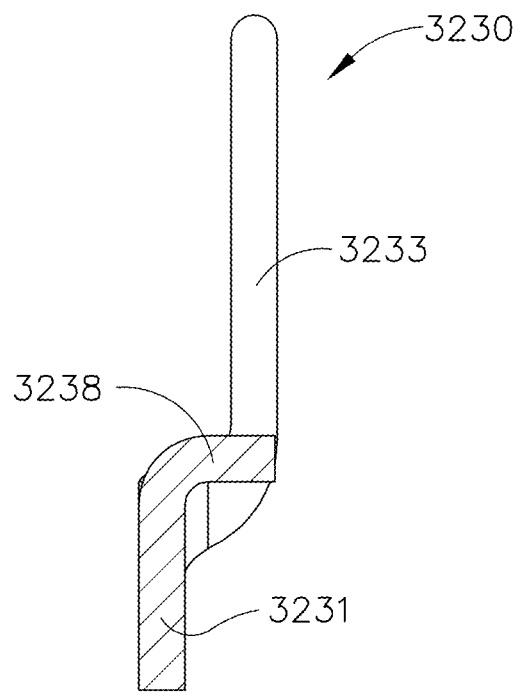
FIG. 79 is a cross-sectional view of the staple of FIG. 78.

A staple 3230 is illustrated in FIGS. 78 and 79. The staple 3230 comprises a base, or crown, 3231, a first leg 3232 extending from the base 3231, and a second leg 3233 extending from the base 3231. Similar to the base 2131 of the staple 2130, the base 3231 of the staple 3230 includes an inclined drive surface defined in a drive plane. Unlike staple 2130, however, the first leg 3232 and the second leg 3233 define a staple forming plane which is transverse to, or non-parallel to, the drive plane.

The staple 3230 further includes a platform 3238 extending from the base 3231. The platform 3238 is integrally formed with the base 3231 and has been folded over such that the platform 3238 extends laterally from the base 3231. The platform 3238 is not directly connected to the legs 3232, 3233. Instead, gaps 3237 are present between the platform 3238 and the legs 3232, 3233. In various other embodiments, the platform 3238 is directly connected to the first leg 3232 and/or the second leg 3233. The platform 3238 extends in a plane, i.e., a support plane, which is transverse to the drive plane and the staple forming plane; however, the platform 3238 can extend in any suitable direction. The platform 3238 is flat, or at least substantially flat; however, the platform 3238 can comprise any suitable shape.

In certain embodiments, the platforms 3238 of the staples 3230 can contact the tissue being stapled when the staples 3230 are implanted into the tissue. The wider platform 3238 can reduce the possibility of the staples 3230 tearing through the tissue.

In various embodiments, a staple cartridge assembly comprises a cartridge body including a deck and staple cavities defined in the deck. The staple cartridge assembly further comprises staples 3230 removably stored in the staple cavities and, in addition, an implantable layer positioned over the deck. The implantable layer can comprise any suitable adjunct such as a tissue thickness compensator and/or a buttress material, for example. A tissue thickness compensator can compensate for variations in the thickness of the tissue being stapled. The implantable layer can be comprised of a woven material and/or a non-woven material, for example.

Further to the above, the platforms 3238 of the staples 3230 can abut the layer when the staples 3230 are implanted into the tissue. In such instances, the platforms 3238 support the layer. Similar to the above, the platforms 3238 can also reduce the possibility of the staples 3230 tearing through the layer. The platforms 3238 of the staples 3230 and the layer can form a co-operative system which distributes the forces, stresses, and/or strains being applied to the tissue over a larger area.

The staple 3230 is formed from a flat sheet of material utilizing a stamping process. During the stamping process, material is removed from the sheet to create the general shape of the staple 3230. The first leg 3232 is bent in a first direction and the second leg 3233 is bent in a second direction; however, both the first leg 3232 and the second leg 3233 can be bent in any suitable direction by a die utilizing a single line of action. The platform 3238 is bent in the same direction as the first leg 3232 during the stamping process, and/or a different stamping process. In certain instances, the platform 3238 can be created utilizing the same single line of action that creates the legs 3232 and 3233. In other instances, the platform 3238 can be created utilizing a second line of action which is transverse or orthogonal to the first line of action.

Figure 86:
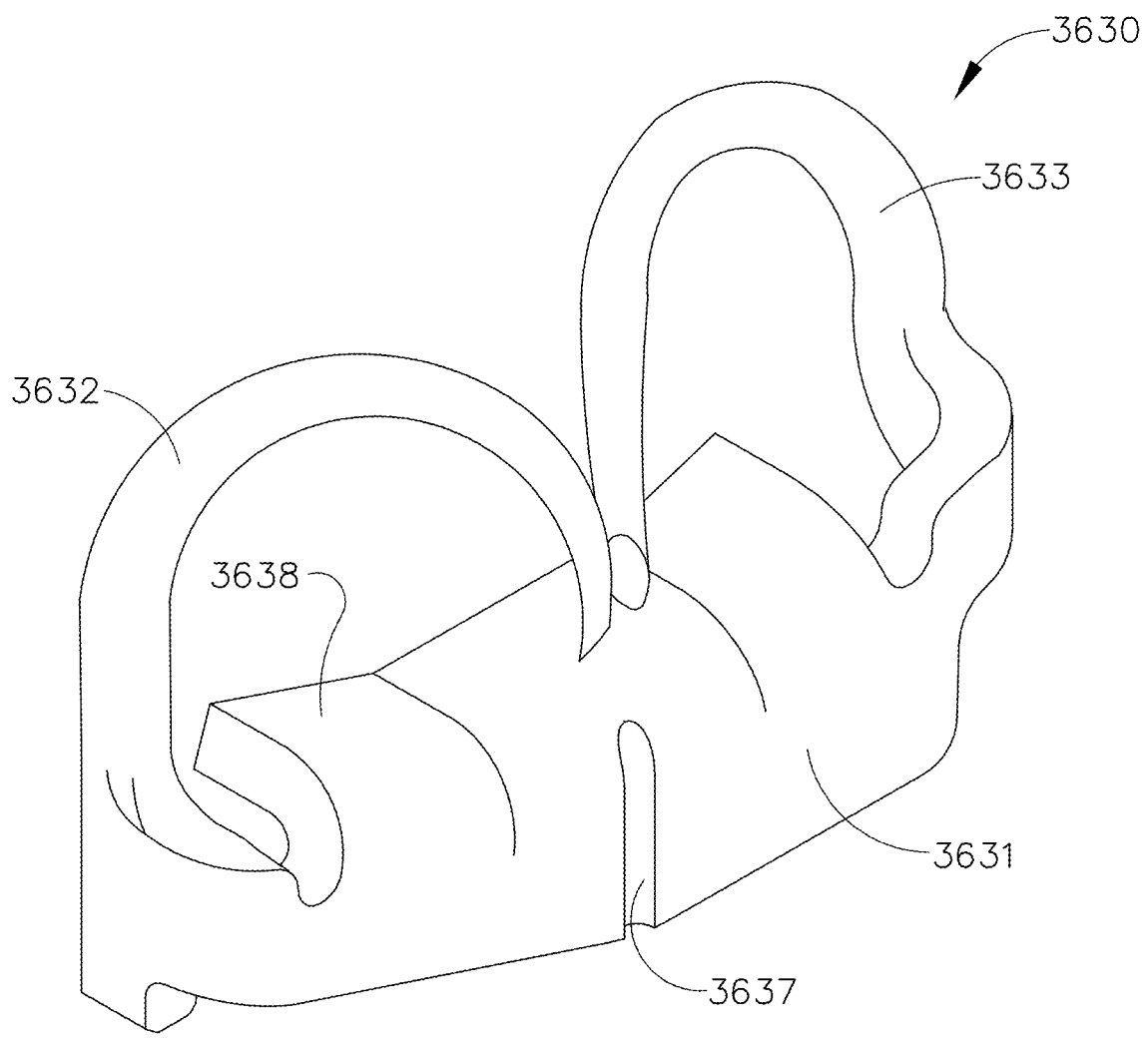
FIG. 86 is a perspective view of a staple in accordance with at least one embodiment illustrated in a deformed configuration.

Turning now to FIG. 86, a staple 3630 comprises a base, or crown, 3631, and legs 3632 and 3633 extending from the base 3631. Similar to the staple 3230, the staple 3630 further comprises a platform 3638 extending from the base 3631. The reader should appreciate that the platform 3238 of the staple 3230 and the platform 3638 of the staple 3630 can increase the moment of inertia, or stiffness, of the staples.

The staple 3630 comprises a relief, or flex, slot 3637 in the base 3631 which decreases the stiffness of the staple 3630, for example. Additionally, or alternatively, a relief slot could be provided in the platform 3638. In any event, more than one relief slot could be utilized to provide the desired stiffness of the staple 3630. Moreover, such relief slots could be adapted to any of the staples disclosed herein.

Figure 80:
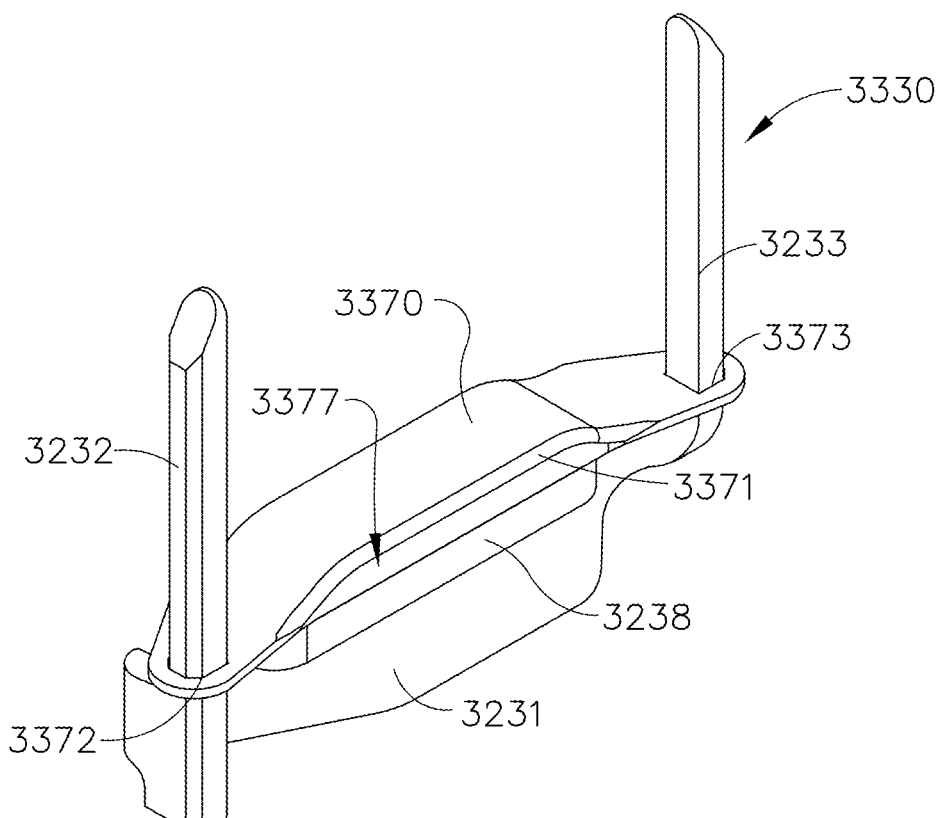
FIG. 80 is a perspective view of a staple assembly in accordance with at least one embodiment.
Figure 81:
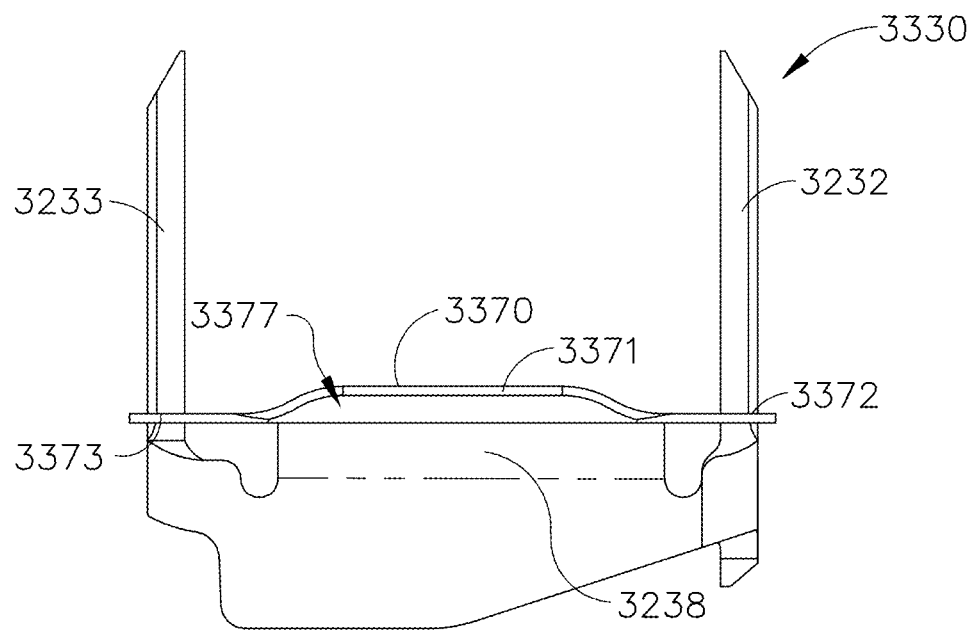
FIG. 81 is an elevational view of the staple assembly of FIG. 80.

In addition to or in lieu of the above, turning now to FIGS. 80 and 81, a staple assembly 3330 comprises a staple 3230 and an implantable adjunct 3370 attached to the staple 3230. The adjunct 3370 comprises a first end including a first aperture 3372 configured to receive the first leg 3232 of the staple 3230 and a second aperture 3373 configured to receive the second leg 3233. As a result, the adjunct 3370 is tethered to the staple legs 3232, 3233 and the movement of the adjunct 3370 relative to the staple 3230 is constrained.

Further to the above, the adjunct 3370 comprises a resilient portion 3371 which extends over the platform 3238 of the staple 3230. A gap 3377 is present between the resilient portion 3371 of the adjunct 3370 and the platform 3238 of the staple 3230 when the staple assembly 3330 is stored in a staple cartridge. When the staple assembly 3330 is ejected from the staple cartridge, the staple legs 3232, 3233 of the staples 3230 penetrate the tissue being stapled and the resilient portion 3371 of the adjunct 3370 comes into contact with the tissue. The resilient portion 3371 is configured to flex, deflect, and/or displace downwardly toward the platform 3238 when the adjunct 3370 comes into contact with the tissue. The resilient portion 3371 can apply a biasing force to the tissue when the tissue is captured within the staple 3230. The movement of the resilient portion 3371 is at least partially constrained by the platform 3238.

Figure 84:
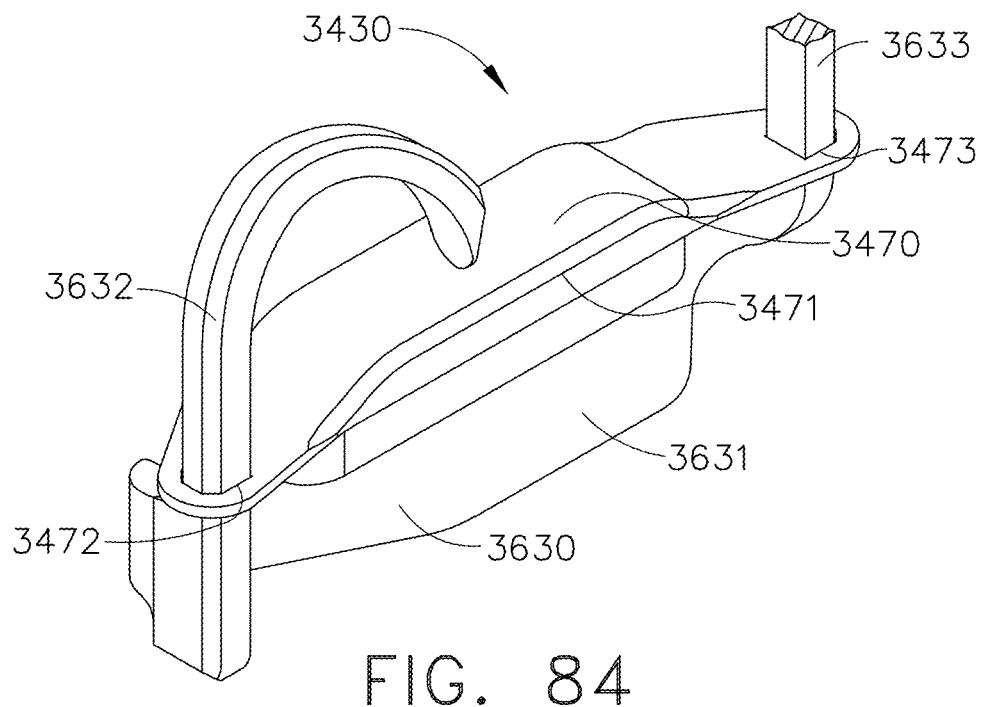
FIG. 84 is a partial perspective view of a staple assembly including the staple adjunct of FIG. 82.

In addition to or in lieu of the above, turning now to FIG. 84, a staple assembly 3430 comprises a staple 3630 and an implantable adjunct 3470 attached to the staple 3230. The adjunct 3470 comprises a first end including a first aperture 3472 configured to receive the first leg 3632 of the staple 3630 and a second aperture 3473 configured to receive the second leg 3633. As a result, the adjunct 3470 is tethered to the staple legs 3632, 3633 and the movement of the adjunct 3470 relative to the staple 3630 is constrained.

Figure 85:
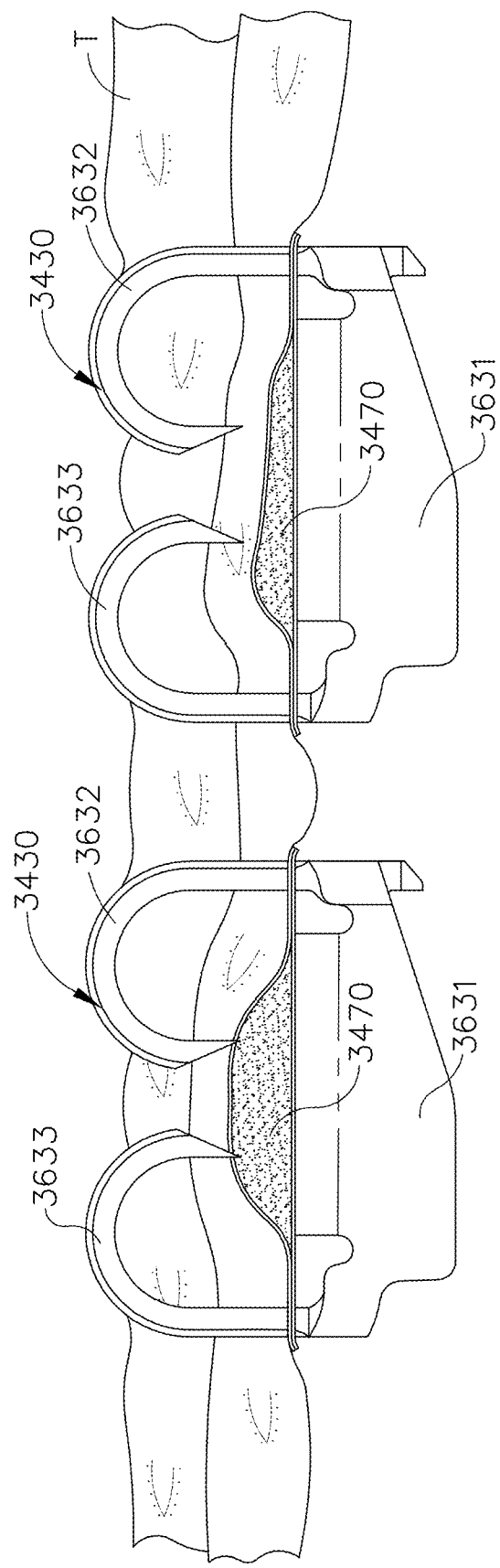
FIG. 85 illustrates the staple assembly of FIG. 84 implanted into tissue.

Further to the above, the adjunct 3470 comprises a resilient portion 3471 which extends over the platform 3638 of the staple 3630. Very little, if any, gap is present between the resilient portion 3471 of the adjunct 3470 and the platform 3638 of the staple 3630 when the staple assembly 3430 is stored in a staple cartridge. When the staple assembly 3430 is ejected from the staple cartridge, the staple legs 3632, 3633 of the staple 3630 penetrate the tissue being stapled and the resilient portion 3471 of the adjunct 3470 comes into contact with the tissue. Referring to FIG. 85, the resilient portion 3471 is configured to flex, deflect, and/or displace downwardly toward the platform 3638 when the adjunct 3470 comes into contact with the tissue. The resilient portion 3471 can apply a biasing force to the tissue when the tissue is captured within the staple 3630. The movement of the resilient portion 3471 is at least partially constrained by the platform 3638.

Figure 82:
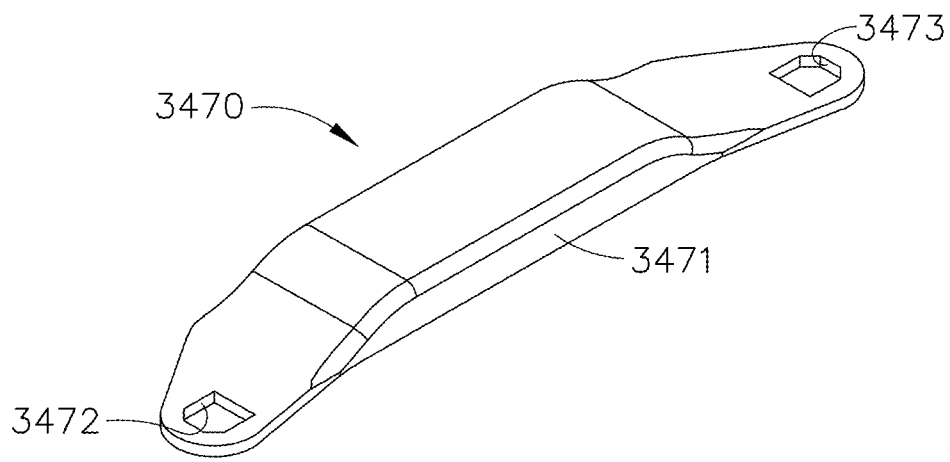
FIG. 82 is a perspective view of an implantable staple adjunct.
Figure 83:
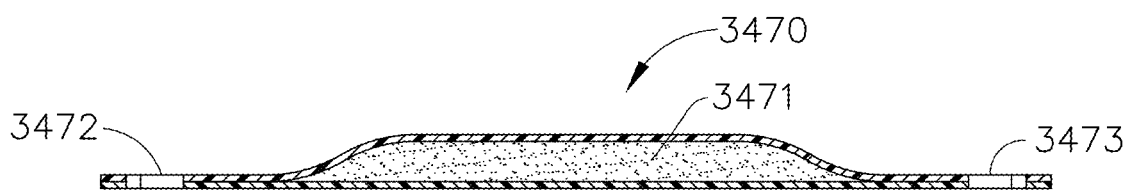
FIG. 83 is a cross-sectional view of the staple adjunct of FIG. 82.

Referring primarily to FIGS. 82 and 83, the resilient portion 3471 of the adjunct 3470 comprises an enclosure. The enclosure is sealed and includes at least one material therein. In various instances, the material comprises a medicament. The medicament is released from the enclosure when the enclosure is ruptured. The enclosure can rupture when the staple assembly 3430 is implanted in the tissue or after a period of time. The adjunct 3470 is comprised of any suitable biocompatible material and, when the biocompatible material comprises a bioabsorbable material, the adjunct 3470 can be absorbed in situ. After a sufficient amount of the adjunct 3470 has been absorbed, the medicament can be released from the adjunct 3470. In various alternative embodiments, an adjunct comprises two separate enclosures. In at least one such embodiment, a first enclosure can contain a first medicament and a second enclosure can contain a second medicament. The first medicament can mix with the second medicament when the enclosures have been ruptured.

Further to the above, the material in the chamber of the resilient portion 3471 can be selected for its mechanical properties such as its elasticity, for example, and can provide the resilient portion 3471 with desirable properties to apply a sufficient biasing force to the tissue. In at least one instance, it may be desirable for the resilient portion 3471 to have mechanical properties which closely resemble that of patient tissue. In other instances, it may be desirable for the resilient portion 3471 to have a stiffness less than the stiffness of patient tissue, for example. Such embodiments may provide a suitable constriction of blood flow within the tissue. In some instances, it may be desirable for the resilient portion 3471 to have a stiffness which is less than the stiffness of the base 3631 but greater than the stiffness of the patient tissue, for example. Such embodiments may provide strain relief to the tissue.

The adjuncts 3370, 3470 can be comprised of a woven material and/or a non-woven material. In at least one instance, the adjuncts 3370, 3470 comprise shells which are comprised of a woven material and/or a non-woven material. The adjuncts 3370, 3470 can be comprised of PGA and/or PLA, for example. In at least one instance, the adjuncts 3370, 3470 comprise shells which are comprised of PGA and/or PLA, for example.

The adjuncts 3370, 3470 are configured to be attached to a single staple. Stated another way, each adjunct 3370, 3470 are only attached to one staple. Such adjuncts can be referred to as pledgets. Alternative embodiments are envisioned in which two or more staples are connected by an adjunct.

Turning now to FIGS. 88 and 89, the various staples disclosed herein, such as staples 2130, for example, can be implanted into the tissue of a patient in longitudinal rows. Two longitudinal rows of staples 2130 are depicted in FIGS. 88 and 89. In various instances, the tissue may stretch in various directions, such as longitudinally, for example. The longitudinal stretch of tissue T is depicted in FIG. 89. As can be seen in FIG. 89, the rows of staples 2130 can stretch along with the tissue T. In such instances, the gaps between the staples 2130 can increase. This gap increase is readily apparent when comparing the unstretched gap distance X1 (FIG. 88) to the stretched gap distance X2 (FIG. 89). The staples 2130 in a third longitudinal row can be positioned and arranged such that they are aligned with or co-extensive with the gaps whether or not the gaps are stretched (X2) or unstretched (X1). Such concepts could be readily adapted to circular and/or curved staple rows, for example.

Figure 87:
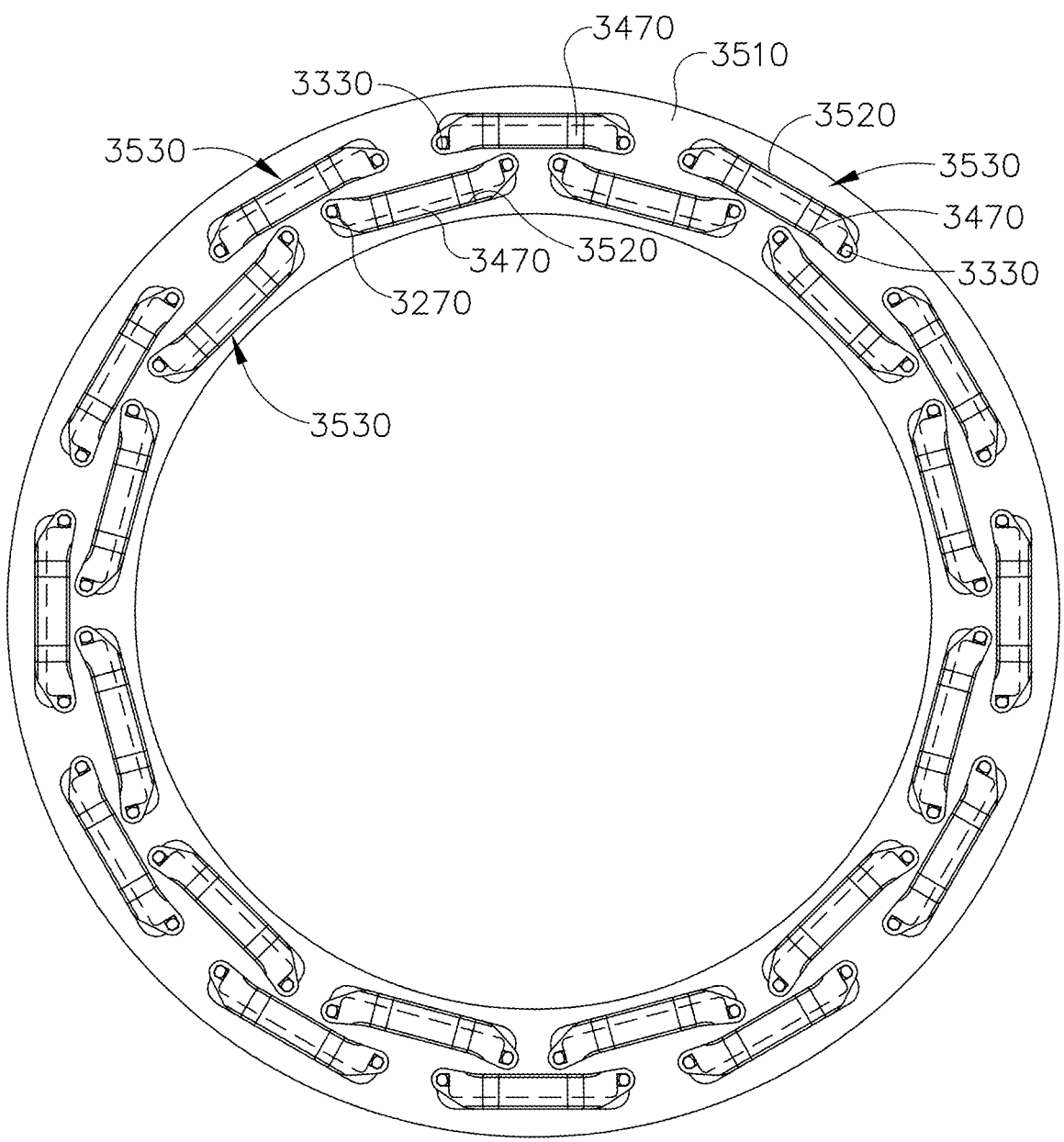
FIG. 87 is a plan view of a circular cartridge body comprising a plurality of the staple assemblies of FIG. 84 in accordance with at least one embodiment.

Turning now to FIG. 87, a circular cartridge body 3510, for example, can utilize the staple assemblies 3430. The cartridge body 3510 comprises a plurality of staple cavities 3520 arranged in circular, concentric rows. As illustrated in FIG. 87, each staple cavity includes a staple assembly 3430 positioned therein; however, any suitable staple could be utilized.

The staples disclosed herein can be comprised of any suitable material. In various instances, the staples are comprised of stainless steel and/or titanium, for example. In certain instances, the staples disclosed herein are comprised of magnesium. The entire disclosures of COMPARISON OF THE EFFECTS OF Mg-6Zn AND Ti-3Al-2.5V ALLOYS ON TGF-β/TNF-α/VEGF/b-FGF IN THE HEALING OF THE INTESTINAL TRACT IN VIVO, Biomed. Mater. 9 (2014) 025011, by Yan et al.; COMPARISON OF THE EFFECTS OF Mg-6Zn AND TITANIUM ON INTESTINAL TRACT IN VIVO, J. Mater. Sci.: Mater. Med., by Yan et al. which published online on Mar. 20, 2013; EVALUATION OF THE SOFT TISSUE BIOCOMPATIBILITY OF MgCa0.8 AND SURGICAL STEEL 316L IN VIVO: A COMPARATIVE STUDY IN RABBITS, Biomed. Eng. OnLine 2010 9:63, by Erdmann et al.; INVESTIGATION OF THE MECHANICAL AND DEGRADATION PROPERTIES OF Mg—Sr AND Mg—Zn—Sr ALLOYS FOR USE AS POTENTIAL BIODEGRADABLE IMPLANT MATERIALS, J. Mech. Behavior of Biomed. Mat. 7 (2012) 87-95, by Brar et al.; Mg—Zr—Sr ALLOYS AS BIODEGRADABLE IMPLANT MATERIALS, Acta Biomaterialia 8 (2012) 3177-3188, by Li et al.; ON THE BIODEGRADABILITY, MECHANICAL BEHAVIOR, AND CYTOCOMPATABILITY OF AMORPHOUS $Mg_{72}Zn_{23}Ca_5$ AND CRYSTALLINE $Mg_{70}Zn_{23}Ca_5Pd_2$ ALLOYS AS TEMPORARY IMPLANT MATERIALS, Soc. Biomat., by Pellicer et al., which published online on Aug. 28, 2012, are incorporated by reference herein. In at least one instance, the staples are comprised of a magnesium alloy including zinc and/or silver, for example. Staples including alloys of magnesium and zinc increase the healing performance of tissue. Staples including silver provide anti-microbial benefits. Staples including all three alloys provide a synergistic dynamic.

Staples comprised of magnesium, including those comprised of a magnesium alloy, can be treated to improve the hardness of the staples. In various instances, a magnesium nitride coating is applied to the magnesium staples. The magnesium nitride coating is applied the entirety of the magnesium staples in certain instances while, in other instances, the magnesium nitride coating is applied to only portions of the magnesium staples. For instance, it may be desirable to coat only the staple legs and/or the tips of the staple legs in magnesium nitride as the staple legs need to have a sufficient hardness to penetrate the tissue. In at least one such instance, a mask can be applied to the remainder of the magnesium staple when the magnesium nitride coating is applied to the staple legs. The magnesium nitride coating can be created by introducing the magnesium staples to a nitrogen-rich environment at an elevated temperature and/or pressure, for example.

In addition to or in lieu of the above, one or more surfaces of the magnesium staples can include a coating including carbon.

In addition to or in lieu of the above, other surface hardening techniques could be utilized. For example, the magnesium staples could be hardened using a laser hardening process and/or a plasma discharge hardening process. In at least one instance, a KERONITE ceramic surface treatment, by Keronite International, can be applied to the staples.

As discussed above, certain portions of the magnesium staples may undergo a hardening process while other portions of the magnesium staples may not undergo a hardening process. In some instances, certain portions of the magnesium staples can be hardened to a first hardness while other portions of the magnesium staples can be hardened to a second hardness which is different than the first hardness. The portions of the magnesium staples having a lower hardness will elude magnesium, zinc, and/or silver ions, for example, faster than the portions of the magnesium staples having a higher hardness.

In addition to or in lieu of the above, magnesium staples, including those comprised of a magnesium alloy, can be at least partially covered in a coating including silver. In at least one instance, the silver coating can include ionized silver, for example. In certain instances, an electroplating process can be utilized to apply the silver coating to the magnesium staples. In various instances, the entirety of the magnesium staples are covered in a silver coating. In at least one instance, a portion, or portions, of the magnesium staples are masked during the electroplating process such that the masked portions are not coated, or at least substantially coated, in silver.

In addition to or in lieu of the above, the staples disclosed herein can be coated, or at least partially coated, in an anti-microbial coating. Such a coating can comprise triclosan, for example. In at least one instance, the triclosan is mixed in an absorbable polymer coating. In certain instances, the coating can comprise LAE intermixed with sodium stearate, for example. The entire disclosure of WO 2012/013577 A1, entitled COMPOSITION FOR COATING MEDICAL DEVICES CONTAINING LAE AND A POLYCATIONIC AMPHOTERIC POLYMER, by Gaffar et al., is incorporated by reference herein.

Figure 90:
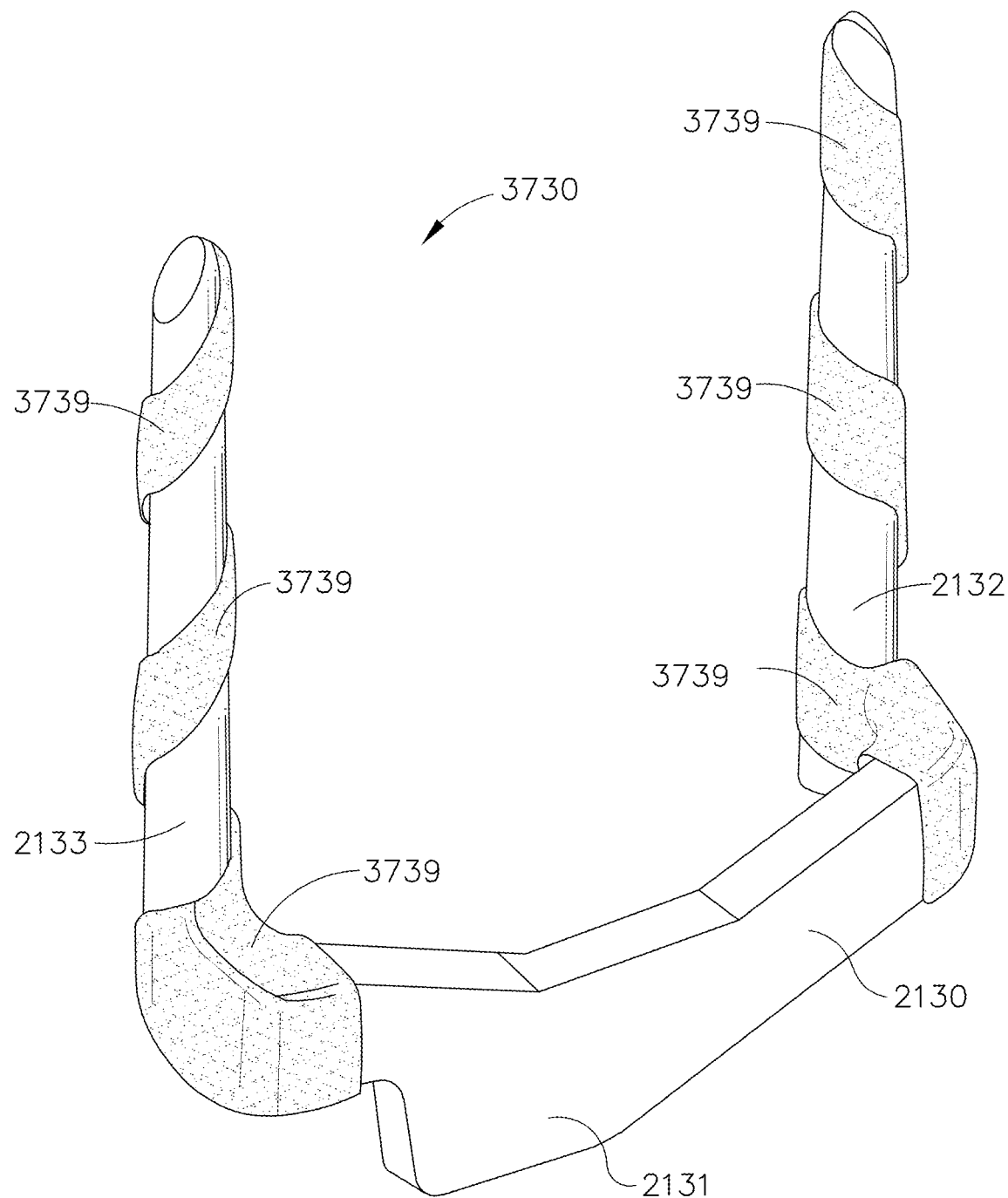
FIG. 90 is a perspective view of a staple in accordance with at least one embodiment.

Turning now to FIGS. 90-92, a staple 3730 comprises a metal frame and a coating 3739 on less than the entirety of the metal frame. The metal frame includes the staple 2130 and is comprised of magnesium and/or a magnesium alloy, for example. The coating 3739 includes a bioabsorbable polymer; however, the coating 3739 can comprise any suitable material. The coating 3739 extends around the legs 2132, 2133 of the metal frame 2130. More specifically, the coating 3739 spirals around each of the legs 2132, 2133; however, any suitable arrangement of the coating 3739 could be utilized. The coating 3739 also covers the transitions, or corners, between the legs 2132, 2133 and the base, or crown, 2131 of the metal frame 2130. The coating 3739 could also cover a portion of the base 2131. In various instances, the coating 3739 can be strategically applied to areas of the metal frame 2130 that are inherently susceptible to faster bioabsorption, such as the bends, edges, and/or corners of the metal frame 2130, for example. In any event, a portion of the metal frame 2130 is covered by the coating 3739 while a portion of the metal frame 2130 is exposed.

The magnesium, or magnesium alloy, metal frame 2130 is bioabsorbable. Referring primarily to FIG. 91, the portions of the metal frame 2130 that are not covered by the coating 3739 are directly exposed to the body when implanted, and, thus, immediately subjected to the body's natural absorption process. The portions of the metal frame 2130 that are covered by the coating 3739 are not directly exposed to the body, at least not initially, when implanted. The coating 3739 protects, or at least somewhat protects, the portions of the metal frame 2130 that it covers and delays the bioabsorption of such portions. Over time, referring primarily to FIG. 92, the unprotected portions of the metal frame 2130 will bioabsorb, leaving behind the portions of the metal frame 2130 that are protected by the coating 3739. The coating 3739 can substantially encapsulate the portions of the metal frame 2130 that it covers, at least until the coating 3739 itself is bioabsorbed and/or until the metal frame 2130 has sufficiently broken apart. At such point, the portions of the metal frame 2130 that the coating 3739 once protected are exposed and can be bioabsorbed by the body.

The bioabsorbable polymer of the coating 3739 can be comprised of PGA and/or PLA, for example; however, the coating 3739 can be comprised of any suitable material including, but not limited to, bioabsorbable polymers and non-bioabsorbable polymers. In certain instances, the coating 3739 comprises a non cross-linked polymer, for example. Such a polymer can cause the coating 3739 to swell and encapsulate any sharp edges of the metal frame 2130 that are created when the metal frame 2130 deteriorates.

In various embodiments, the coating 3739 can be arranged in a grid, mesh, and/or lattice arrangement on the metal frame 2130 In such an embodiment, the metal frame 2130 can be exposed in the openings in the grid which can allow the metal frame 2130 to be bioabsorbed in such openings. As the metal frame 2130 begins to deteriorate, the latticed coating 3739 can act as a net or cage and hold the fragments of the metal frame 2130 together, for example, at least until the coating 3739 is bioabsorbed.

The coating 3739 can be applied to the metal frame 2130 in any suitable manner. In at least one instance, the coating 3739 can be sprayed onto the metal frame 2130 such that the coating 3739 is applied in a random manner which creates random openings through which the metal frame 2130 can be bioabsorbed. In certain other instances, the coating 3739 can be applied to the metal frame 2130 in a pattern. In at least one such instance, the pattern can include a dot-matrix pattern having islands of coating surrounded by exposed portions of the metal frame 2130.

In certain alternative embodiments, a staple can include two or more coatings. In at least one such instance, a first coating can be bioabsorbed at a first rate and a second coating can be bioabsorbed at a second rate to expose different portions of the metal frame 2130 at different times during the healing process, for example. Such staples can still have uncovered portions; however, it is contemplated that every portion of a staple could be covered by at least one or more coatings.

The therapeutic benefits provided by the materials disclosed herein are a function of the surface area of the staples that is exposed to the patient's body. Staples having a larger surface area may deliver such therapeutic benefits faster than staples having a smaller surface area. That said, staples having a smaller surface area may provide such therapeutic benefits over a longer period of time. Nonetheless, the surface area of the staples disclosed herein can be increased by introducing apertures into the staples. For instance, one or more apertures, or through holes, can be created in the base, or crown, 2131 of the staple 2130, for example. The through holes can permit tissue to grow through the staple 2130 and improve the assimilation of the staple 2130 into the body.

In at least one embodiment, further to the above, the coating 3739 is not positioned in the apertures as the coating 3739 would reduce the available surface absorption area of the staple 2130. However, if delaying the bioabsorption of these staple portions is desired, the apertures in the staple 2130 could be filled, or at least partially filled, with the coating 3739. As discussed above, the coating 3739 can be configured to delay the absorption of the underlying metal frame; however, any suitable coating could be utilized. For example, a coating on the metal frame could encourage tissue ingrowth into the structure of the staple. In at least one such instance, the coating comprises small micropillars that create a porous and/or prickly interaction with the tissue.

In various embodiments, further to the above, a suture, or string, can extend through the apertures defined in the staples. Such a suture can tether the staples together. In various instances, the suture is threaded through the apertures while the staples are positioned in the staple cartridge. In other instances, the suture is threaded through the apertures after the staples have been implanted into the tissue. In at least one embodiment, the suture is positioned in a groove defined in the deck of the staple cartridge and the staples each comprise a slot or hook defined therein which is configured to catch the suture as the staples are being deployed. In any event, the suture can be pulled to gather the stapled tissue together, such as in a purse-string tissue gathering technique, for example.

In various embodiments, the staples disclosed herein can comprise barbs. In at least one instance, barbs are defined on the staple leg such that the barbs engage a layer that is implanted with the tissue. Such barbs can reduce relative movement between the layer and the staples. In certain embodiments, barbs are defined on the base of the staple. Such barbs can grip a layer of tissue positioned adjacent the implanted staples.

Figure 93:
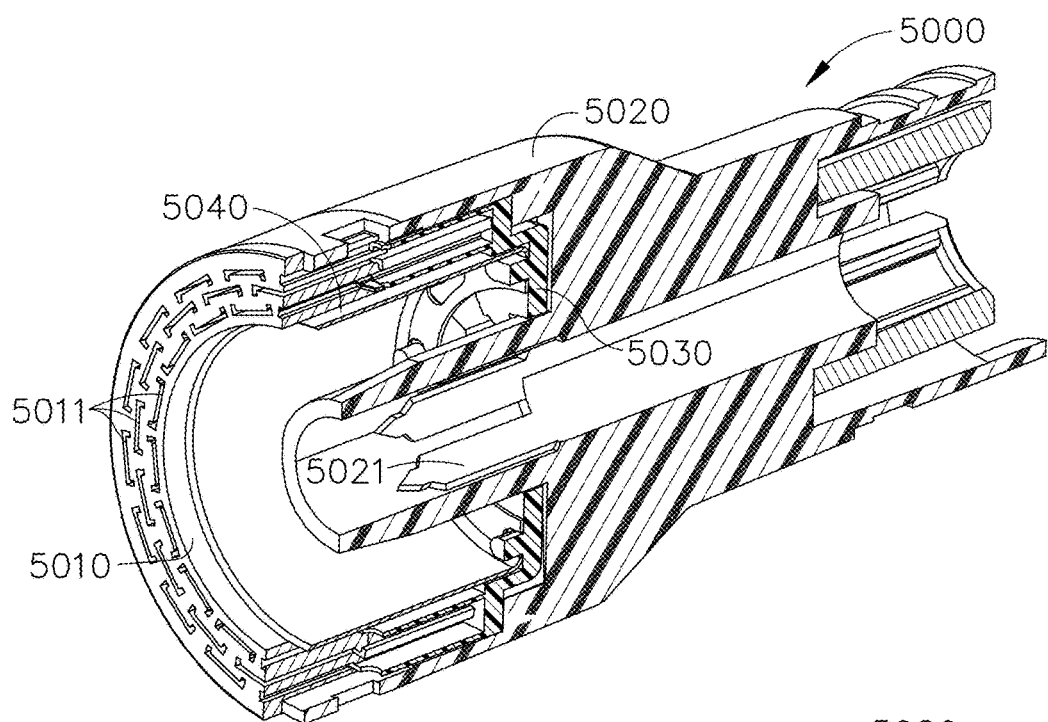
FIG. 93 is a cross-sectional perspective view of a portion of a circular surgical stapler in accordance with at least one embodiment.
Figure 94:
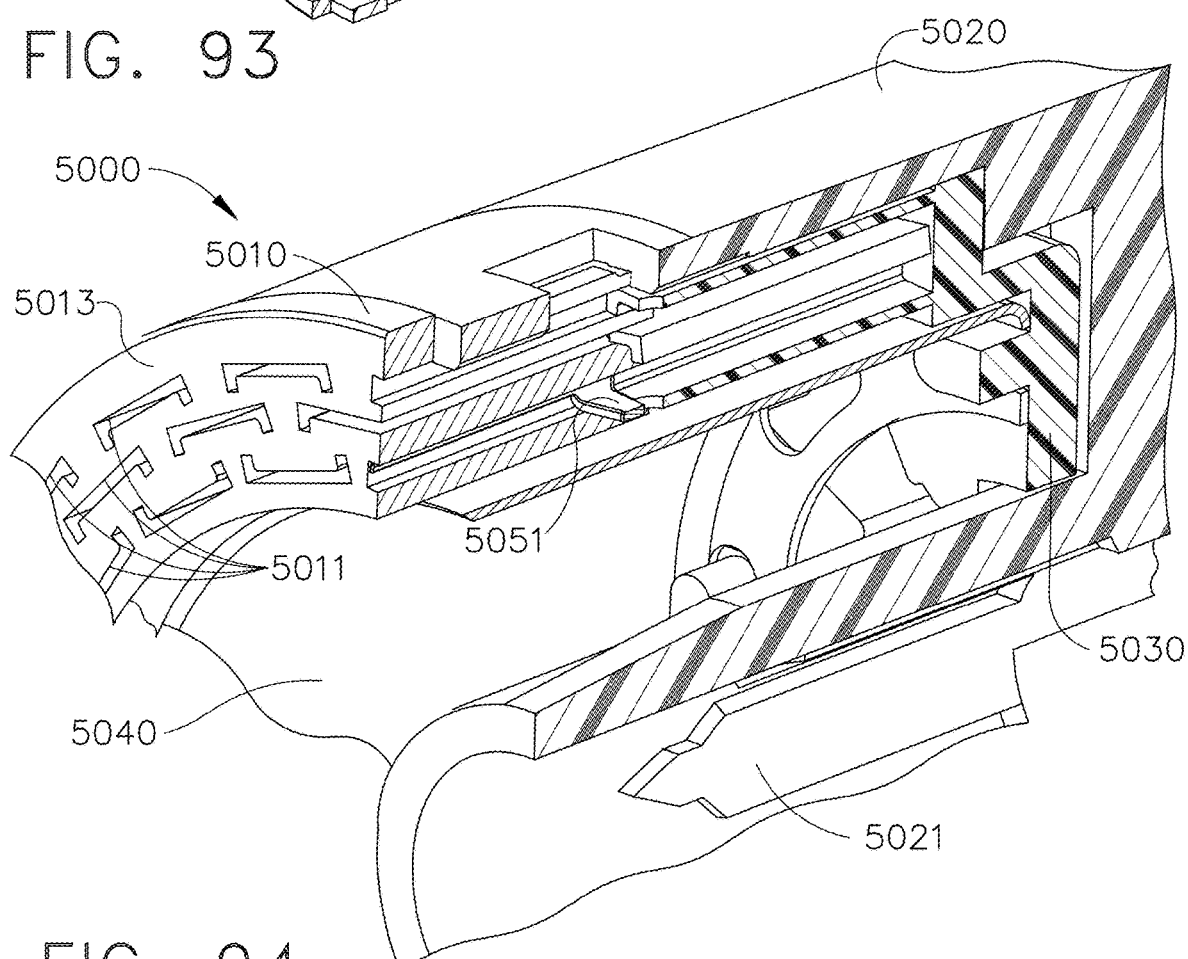
FIG. 94 is a partial cross-sectional perspective view of the circular surgical stapler of FIG. 93.
Figure 95:
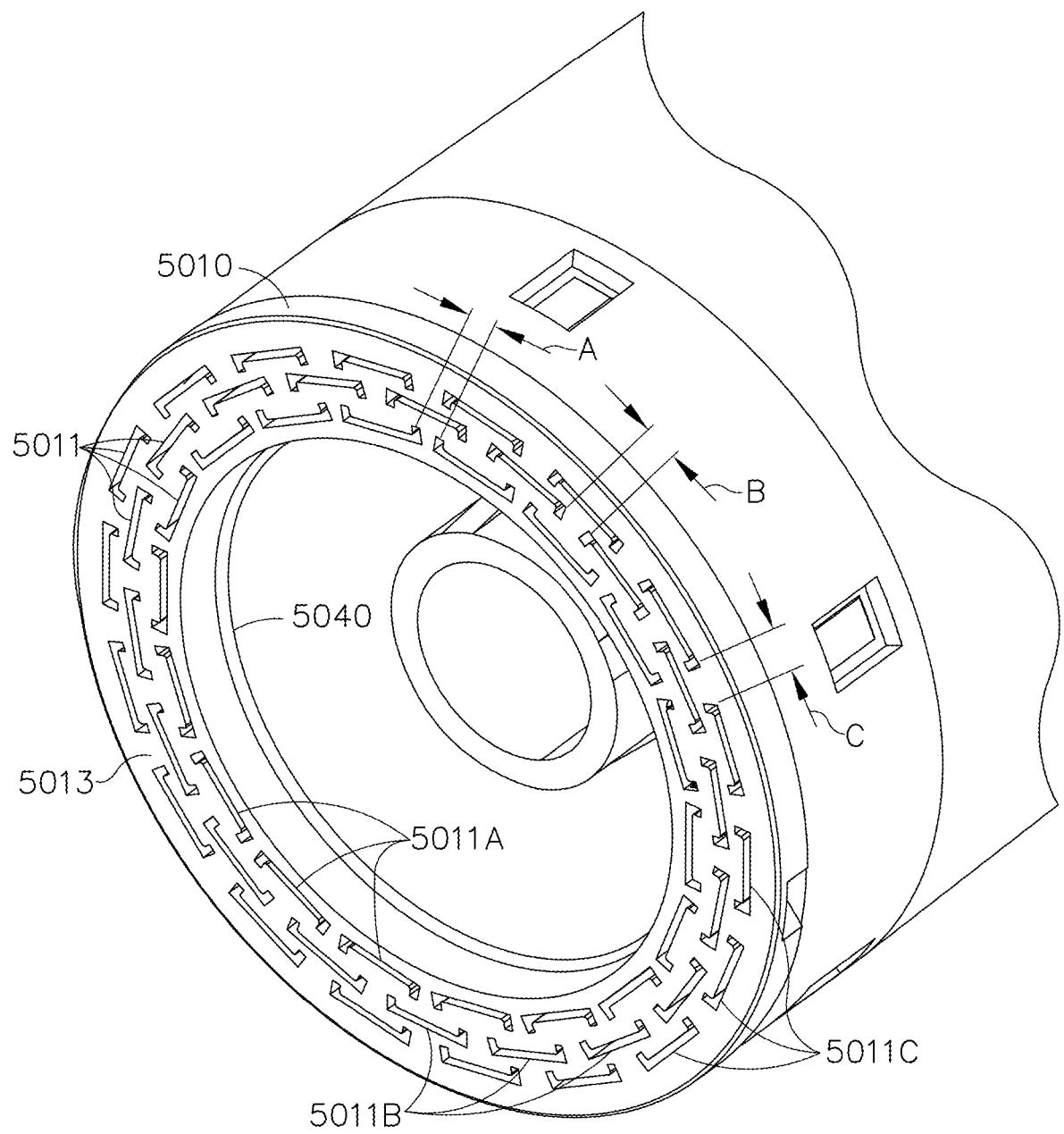
FIG. 95 is a partial perspective view of the circular surgical stapler of FIG. 93.

A circular surgical stapler 5000 is depicted in FIGS. 93-95. The circular surgical stapler 5000 comprises a frame assembly 5020 comprising an attachment portion 5021 configured to operably couple an anvil to the circular surgical stapler 5000. The circular surgical stapler 5000 further comprises a knife member 5040 configured to incise tissue captured by the circular surgical stapler 5000, a surgical staple cartridge 5010 which removably stores a plurality of staples 5051 therein, and a pusher assembly, or driver, 5030 configured to eject the staples 5051 out of the staple cartridge 5010. The surgical staple cartridge 5010 comprises a cartridge deck 5013 and a plurality of staple cavities 5011 defined in the cartridge deck 5013 which removably store the staples 5051. The staples 5051 are similar to the staples discussed in greater detail herein, however, any suitable staple may be used. The staples 5051 comprise staple legs in a plane which is offset from a plane defined by the staple base portion.

Referring primarily to FIG. 95, the staple cavities 5011 of the staple cartridge 5010 comprise an inner row of staple cavities 5011A, an intermediate row of staple cavities 5011B, and an outer row of staple cavities 5011C. Staple row spacing may can include any suitable spacing; however, nested rows may be closer together than non-nested rows. The intermediate row of staple cavities 5011B is positioned radially outward with respect to the inner row of staple cavities 5011A. The outer row of staple cavities 5011C is positioned radially outward with respect to the intermediate row of staple cavities 5011B. The staple cavities 5011A in the inner row comprise an orientation which orients the staple legs of the staples 5051 stored therein such that the staple legs extend radially outward with respect to the staple base. The intermediate row of staple cavities 5011B and the outer row of staple cavities 5011C comprise an orientation which orients the staple legs of the staples 5051 stored therein such that the staple legs extend radially inward with respect to the staple bases.

The staple cavities 5011A in the inner row define a plurality of first gaps therebetween having a distance A. The intermediate row of staple cavities 5011B define a plurality of second gaps with a distance B. The outer row of staple cavities 5011C define a plurality of third gaps with a distance C. The distance A is less than the distances B and C. The distance B is greater than the distance A but less than the distance C. The distance C is greater than the distances A and B. The cavities 5011 are arranged such that the first gaps comprise a distance which is greater than the distances of the second gaps and/or the third gaps. The cavities 5011 are arranged such that the third gaps comprise a distance which is less than the distances of the first gaps and/or the second gaps. Embodiments are envisioned where there are no gaps associated with one or more rows of staple cavities.

The intermediate row of staple cavities 5011B are arranged such that the cavities 5011B overlap the first gaps defined by the inner row of staple cavities 5011A in order to compensate for the lack of tissue ligation in the first gaps. The outer row of staple cavities 5011C are arranged such that the cavities 5011C overlap the second gaps defined by the intermediate row of staple cavities 5011B in order to compensate for the lack of tissue ligation in the second gaps. Overlapping these fastening gaps with such an arrangement increases the ligation ability of the circular surgical stapler 5000. This arrangement also permits the fastened tissue to flex upon fastening. Conventional arrangements utilize greater quantities of staples in the intermediate and/or outer rows in order to increase ligation efficiency; however, such conventional arrangements can limit tissue flexibility after fastening.

Figure 96:
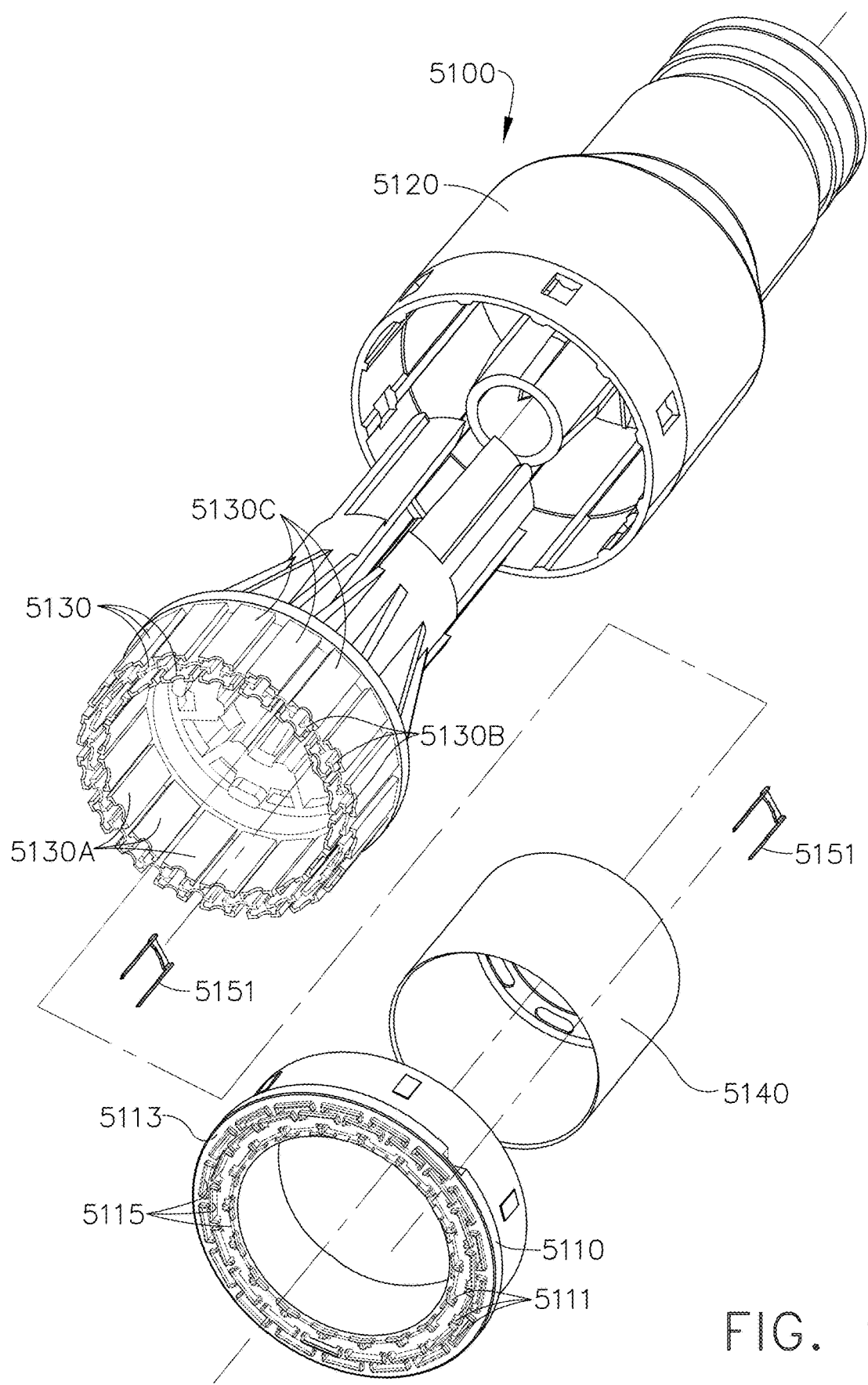
FIG. 96 is a partial exploded perspective view of a circular surgical stapler in accordance with at least one embodiment.
Figure 97:
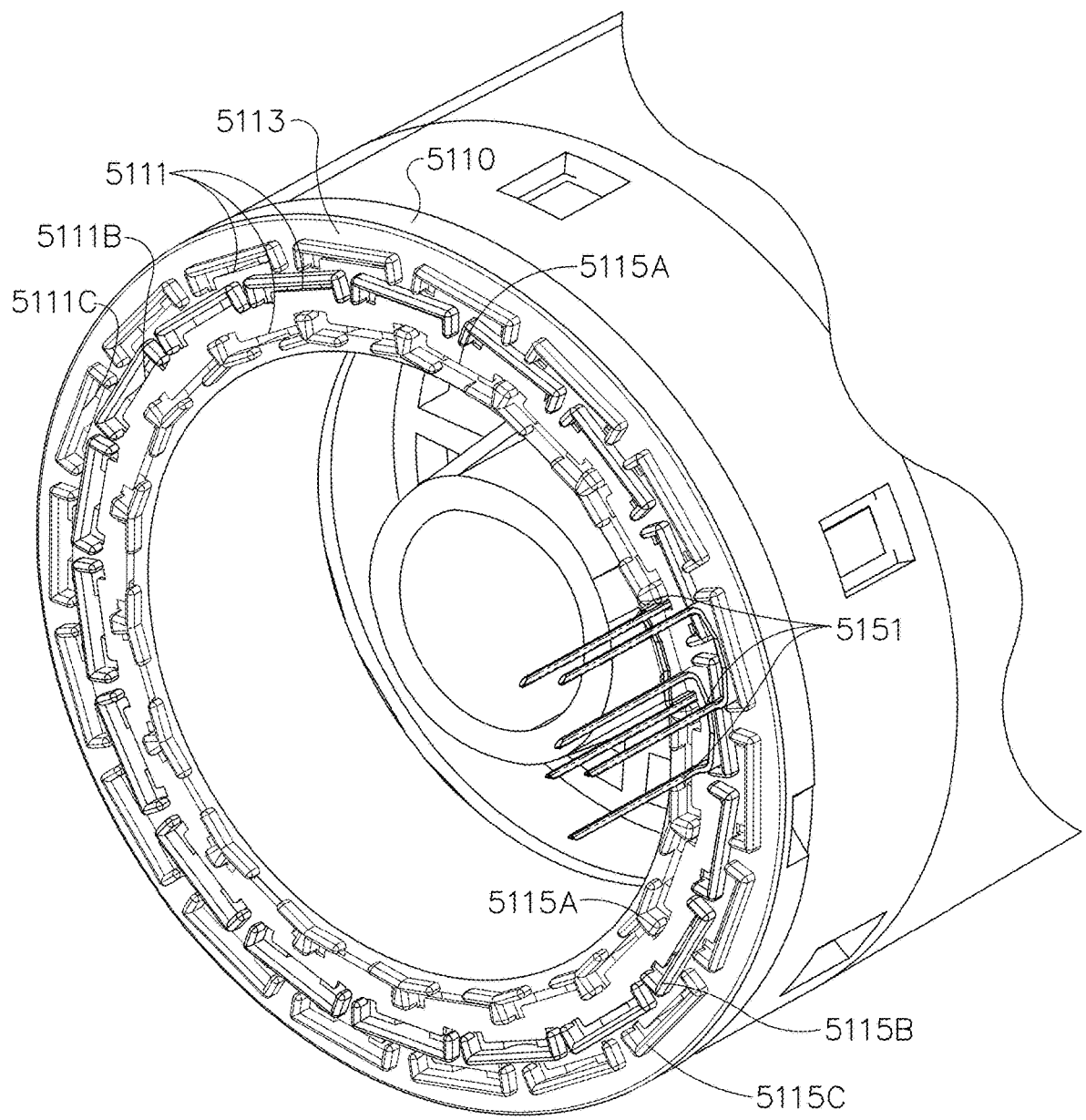
FIG. 97 is a partial perspective view of the circular surgical stapler of FIG. 96 illustrating staples in a preloaded position.
Figure 98:
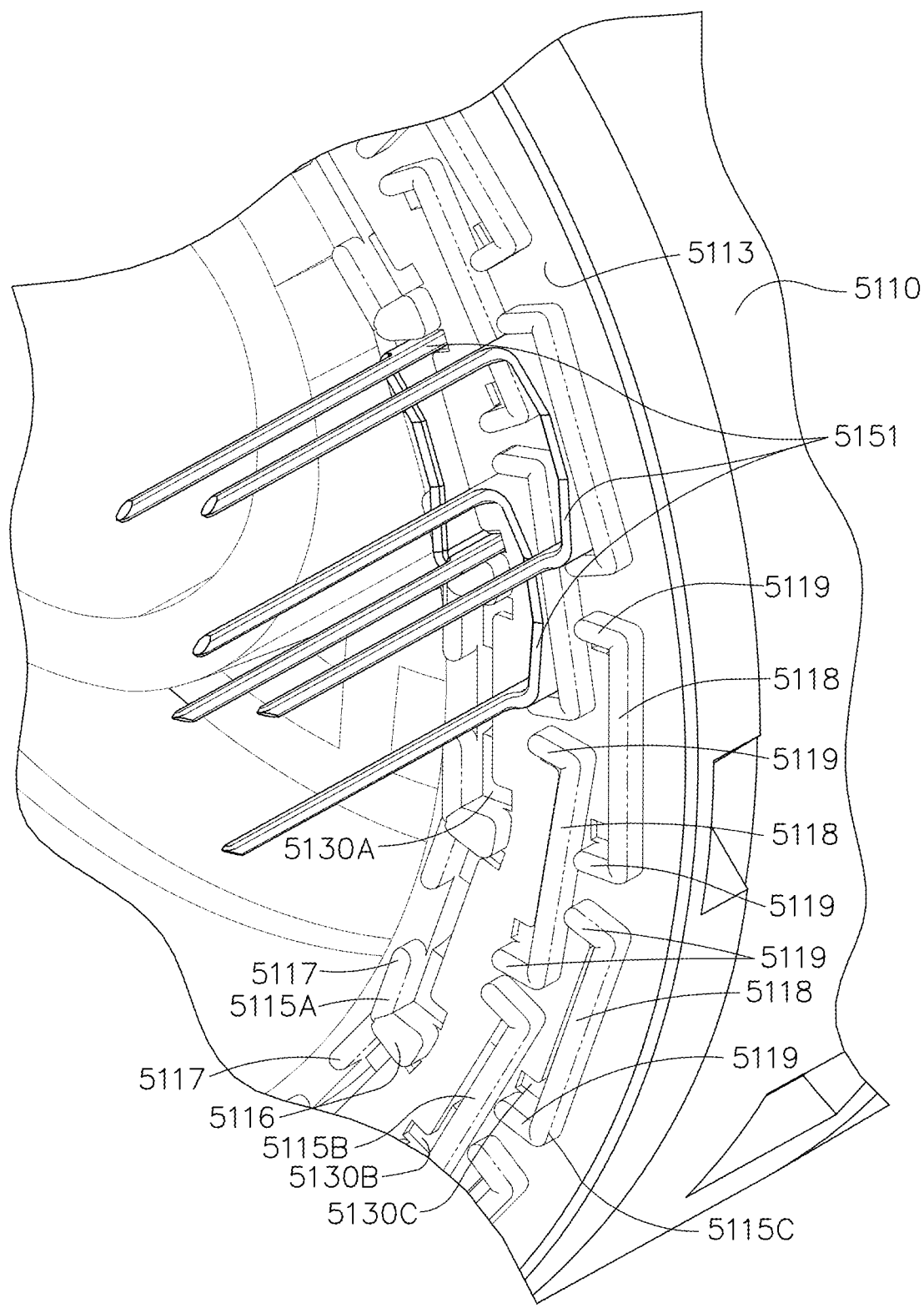
FIG. 98 is a partial perspective view of the circular surgical stapler of FIG. 96.

FIGS. 96-98 illustrate a circular surgical stapler 5100 in accordance with at least one embodiment. The circular surgical stapler 5100 comprises a frame assembly 5120 comprising an attachment portion configured to operably couple an anvil to the circular surgical stapler 5100. The circular surgical stapler 5100 further comprises a knife member 5140 configured to incise tissue captured by the circular surgical stapler 5100, a surgical staple cartridge 5110 which removably stores a plurality of staples 5151 therein, and a pusher assembly, or driver, 5130 configured to eject the staples 5151 out of the staple cartridge 5110. The pusher assembly 5130 comprises an inner row of staple drivers 5130A, an intermediate row of staple drivers 5130B, and an outer row of staple drivers 5130C. The surgical staple cartridge 5110 comprises a cartridge deck 5113 and a plurality of staple cavities 5111 defined in the cartridge deck 5113 which removably store the staples 5151 therein. The surgical staple cartridge 5110 further comprises a plurality of deck features, or staple supports, or guides, 5115 configured to support, guide, and/or control the staples 5151 when the staples 5151 are ejected from the staple cartridge 5110. The deck features, or cavity extenders, 5115 can have a multitude of purposes such as aiding in the gripping of tissue intermediate the anvil and the staple cartridge 5110 and/or storing, releasing, and delivering a medicament to tissue captured with the stapler 5100, for example.

The staple cavities 5111 of the staple cartridge 5110 are similar to the staple cavities 5011 in many respects. The staple cavities 5111 comprise an inner row of staple cavities 5111A, an intermediate row of staple cavities 5111B, and an outer row of staple cavities 5111C. The deck features 5115 comprise a plurality of first deck features 5115A, a plurality of second deck features 5115B, and a plurality of third deck features 5115C. Each first deck feature 5115A comprises an intermediate portion 5116 and two outer portions 5117 to define a T-configuration. The intermediate portion 5116 sits between two staple cavities 5111A and extends from the deck 5113 to guide and/or support neighboring staple legs. The outer portions 5117 branch off of the intermediate portion 5116 in at least substantially opposite directions and extend from the deck 5113 to guide and/or support a portion of a staple base. Combining deck features for more than one cavity in such a manner can save space on the cartridge deck 5113.

Each second deck feature 5115B and each third deck feature 5115C comprise an intermediate portion 5118 and two outer portions 5119 to define a cavity-surrounding configuration. The intermediate portion 5118 extends from the deck 5113 to guide and/or support staple bases of staples removably stored in the intermediate row of staple cavities 5111B and the outer row of staple cavities 5111C. The two outer portions 5119 branch off from the intermediate portion 5118 to support the staple legs that extend from the staple base that the intermediate portion 5118 is guiding and/or supporting.

Figure 99:
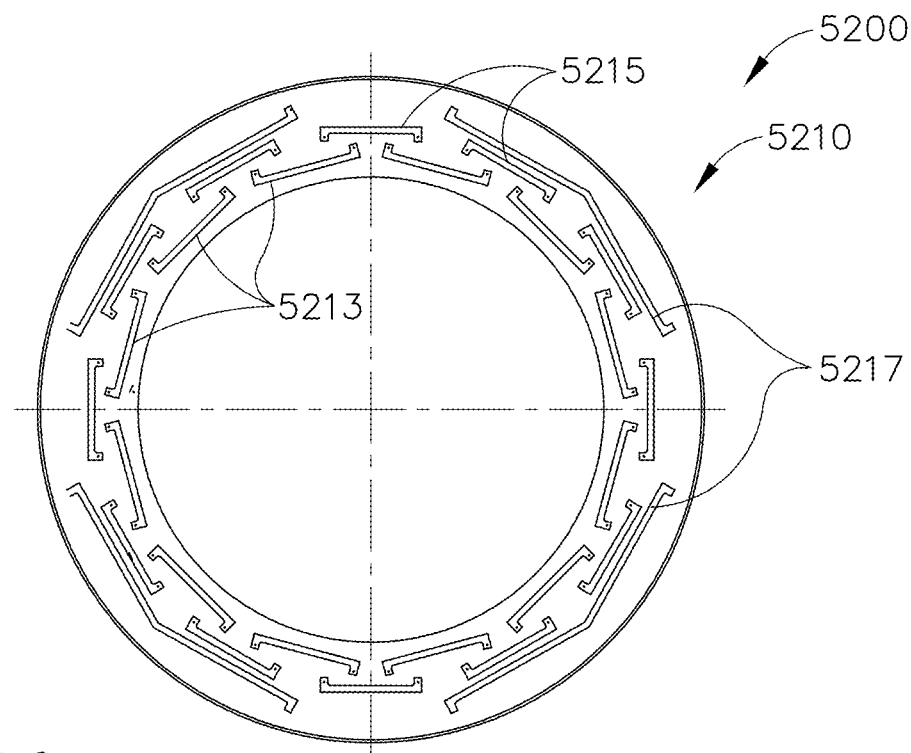
FIG. 99 is an end view of a circular surgical stapling configuration in accordance with at least one embodiment.

FIG. 99 illustrates a circular stapling configuration 5200 for use with a circular surgical stapler in accordance with at least one embodiment. The circular stapling configuration 5200 is an arrangement of staples employable with a circular staple cartridge. A circular staple cartridge employing the circular stapling configuration 5200 comprises corresponding staple cavities to removably store the staples discussed herein. The circular stapling configuration 5200 comprises a plurality of staples 5210 comprising an inner row of staples 5213, an intermediate row of staples 5215, and an outer row of staples 5217. Each staple 5213 is orientated such that its staple legs face outward toward the outer row of staples 5217. Each staple 5215 is orientated such that its staple legs face inward toward the inner row of staples 5113. Each staple 5217 is orientated such that its staple legs face outward away from the inner row of staples 5213 and the intermediate row of staples 5215. Each staple row may reside a certain distance from each other staple row and/or the cutting member to better control blood flow and/or predict tissue behavior at certain points within the stapled tissue.

The outer row of staples 5217 comprise different characteristics than the inner and/or intermediate row of staples 5213, 5215. For example, in various instances, the outer row of staples 5217 are formed into a larger "B" formation resulting in a greater capture volume and/or taller staple forming height to alleviate high tissue compression near the outer row of staples 5217. A larger B formation may also improve blood flow toward the inner rows. In various instances, the outer row of staples 5217 comprise a greater resistance to unfolding by utilizing a larger staple crown, staple leg widths, and/or staple leg thicknesses.

The quantity of staples used in each row of staples can vary in a circular and/or linear surgical staple cartridge. The outer row of staples 5217 comprise a first quantity, the intermediate row of staples 5215 comprise a second quantity, and the inner row of staples 5213 comprise a third quantity. FIG. 99 illustrates a scenario where the first quantity is equal to the second quantity, but, greater than the third quantity. In various embodiments, the first quantity, the second quantity, and the third quantity are different. In various embodiments, the first quantity is greater than the second quantity and the second quantity is greater than the third quantity.

Varying staple crown widths between staple rows can provide an effective and/or efficient stapling arrangement. For example, each outer row staple 5217 comprises a staple crown having a width that is greater than the crown width of each inner row staple 5213 and each intermediate row staple 5215. The staple crown of each outer row staple 5217 is bent laterally in order have a larger crown width staple while maintaining the compact circular stapling arrangement. Some embodiments are envisioned where the crown of each outer row staple 5217 is curved. One advantage of bending or curving the crown of the outer row staples 5217 can include being able to nest the outer row staples 5217 closer to the intermediate row staples 5215 and the inner row staples 5213, for example. Each outer row staple 5217 spans a plurality of gaps defined between the inner row staples 5213 and/or the intermediate row staples 5215. Each intermediate row staple 5215 spans, overlaps, or covers each gap defined between the inner row of staples 5213.

In various embodiments the gaps defined by the inner row staples 5213 can be varied based on the radial position of the row of inner staples. For example, a row of inner staples having a diameter much less than the diameter of the intestine being stapled may comprise much larger gaps between the inner row staples to provide radial flexibility, and/or expansion. A row of inner staples having a diameter less than, but closer to, the diameter of the intestine being stapled may comprise smaller gaps between the inner row staples because, in this instance, vast expansion and/or flexibility may not be necessary.

Figure 100:
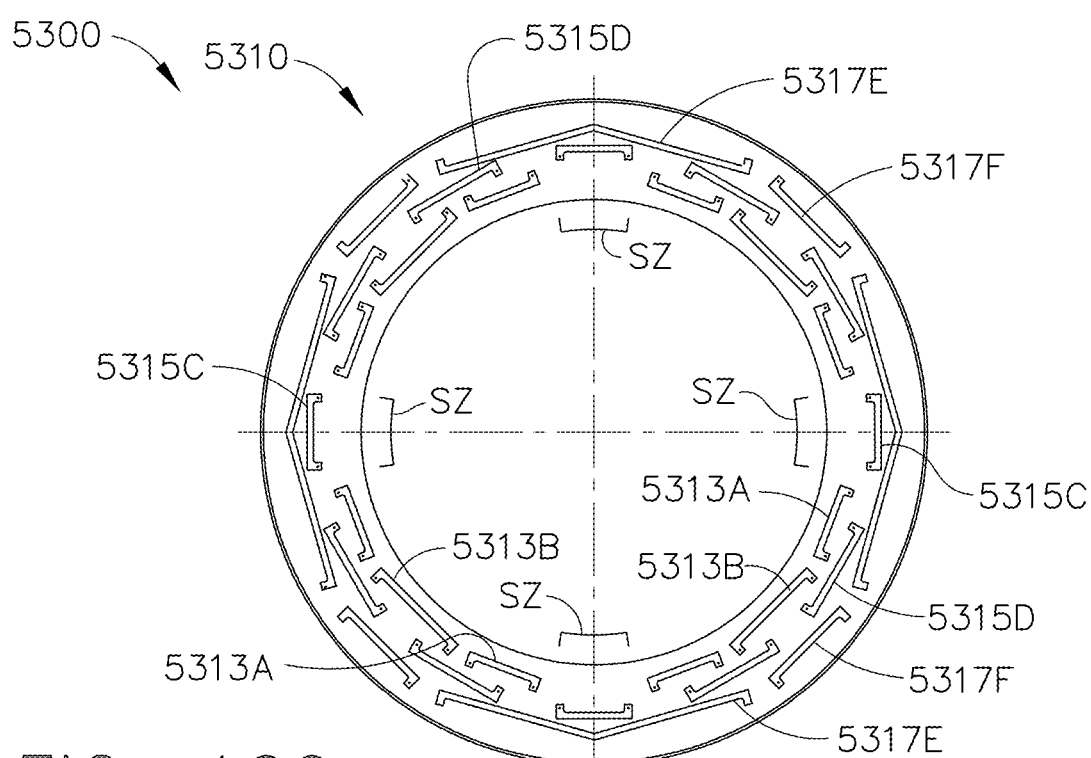
FIG. 100 is an end view of a circular surgical stapling configuration in accordance with at least one embodiment.

FIG. 100 illustrates a circular stapling configuration 5300 for use with a circular surgical stapler in accordance with at least one embodiment. The circular stapling configuration 5300 is an arrangement of staples employable with a circular staple cartridge. A circular staple cartridge employing the circular stapling configuration 5300 comprises corresponding staple cavities to removably store the staples discussed herein. The circular stapling configuration 5300 comprises a plurality of staples 5310 comprising inner row staples 5313A, 5313B, intermediate row staples 5315C, 5315D, and outer row staples 5317E, 5317F. Each staple 5313A, 5313B is orientated such that the staple legs thereof face outward toward the outer row staples 5317E, 5317F. Each staple 5315C, 5315D is orientated such that the staple legs thereof face inward toward the inner row staples 5313A, 5313B. Each staple 5317E, 5317F is orientated such that the staple legs thereof face outward away from the inner row staples 5313A, 5313B and the intermediate row staples 5315C, 5315D. Embodiments are envisioned where various staples within the same row face opposite directions. Embodiments are envisioned where every staple in every row faces the same direction. Embodiments are envisioned where the inner row staples face inward, the intermediate row staples face outward, and the outer row staples face inward, for example.

Varying staple crown widths between and within staple rows can also provide an effective and/or efficient stapling arrangement. For example, the inner row staples 5313A, 5313B each comprise a different crown width, the intermediate row staples 5315C, 5315D each comprise a different crown width, and the outer row staples 5317E, 5317F each comprise a different crown width. In various embodiments, the crown widths of each staple 5313A, 5313B, 5315C, 5315D, 5317E, and 5317F are all different. Embodiments are envisioned where crown widths of certain staples in one row are equal to crown widths of certain staples in another row. The inner row staples define a stretch zone labeled SZ. The stretch zone SZ can comprise a gap defined between the staples 5313A, for example. The stretch zone SZ permits the stapled tissue to flex.

Figure 101:
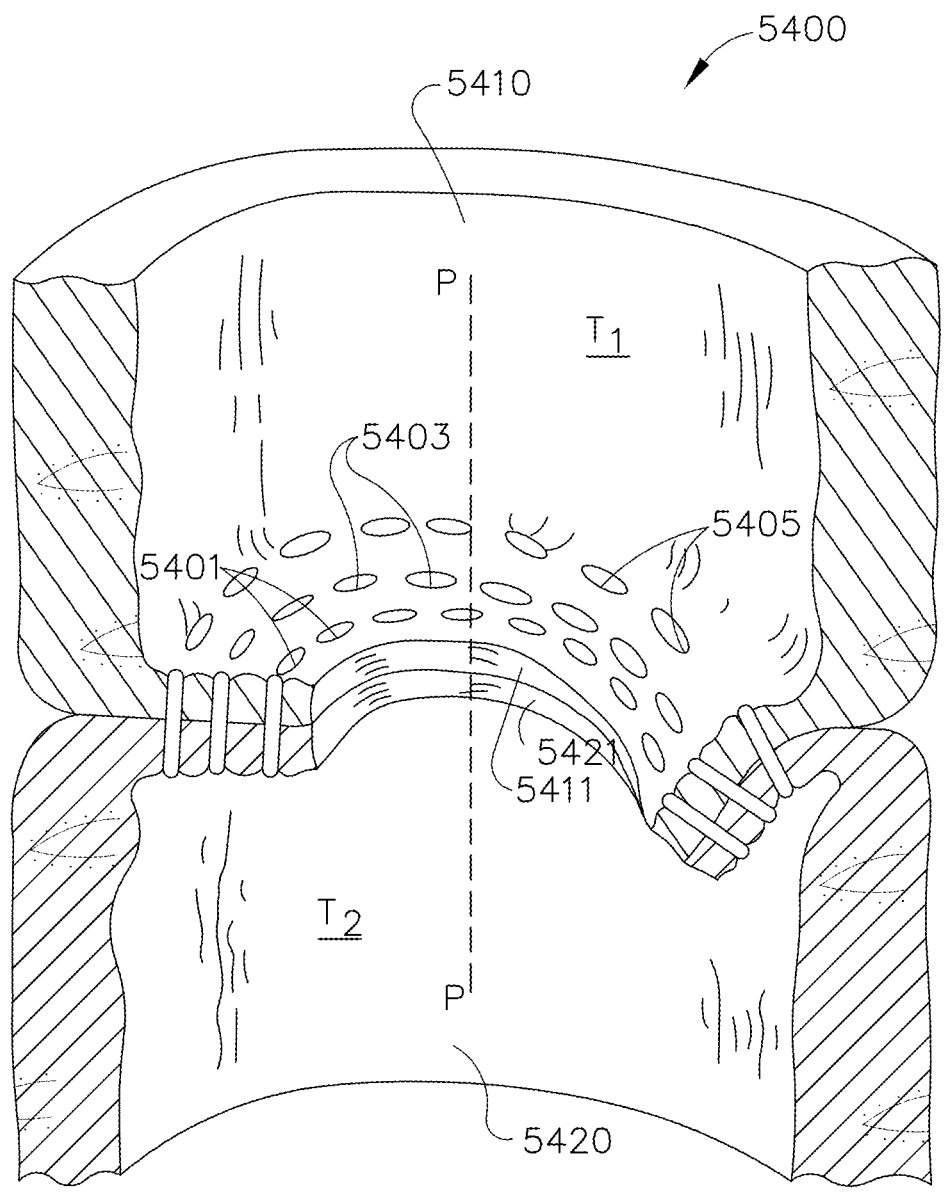
FIG. 101 is partial cross-sectional view of a colon stapled with a circular stapling instrument disclosed herein.

The circular surgical staplers, circular staple cartridges, and/or circular stapling configurations may be employed in a colectomy procedure, for example. FIG. 101 illustrates an example of a part of a colectomy procedure where two portions of intestine are joined providing a new pathway, or passage, 5400 for the digestive system. One portion of intestine $T_1$ comprises an inner wall 5410 and a second portion of intestine $T_2$ comprises an inner wall 5420. The intestine portions $T_1$ and $T_2$ are stapled with inner staples 5401, intermediate staples 5403, and outer staples 5405. The intestine portions $T_1$ and $T_2$ are incised creating a new passage P-P for digestive material to pass. The incision creates cut portions 5411 and 5421 of the intestine portions $T_1$ and $T_2$. The change in diameter between the inner walls 5410, 5420 of the intestine portions $T_1$ and $T_2$ and the cut portions 5411, 5421 can, in some cases, constrict, or narrow, the passage P-P making it difficult for digestive material to pass. It can be desirable to have flexibility of the staple portion starting with the inner staples 5401. One method for providing flexibility utilizes staple gaps defined between staples in the various rows in which the staples are arranged. Another method for providing flexibility utilizes larger sized staples with larger staple crowns. In various instances, gaps between the staples and staple rows permit flexibility of the stapled portion allowing digestive material to pass more easily. In various instances, different size staples permit tissue flexibility.

Figure 102:
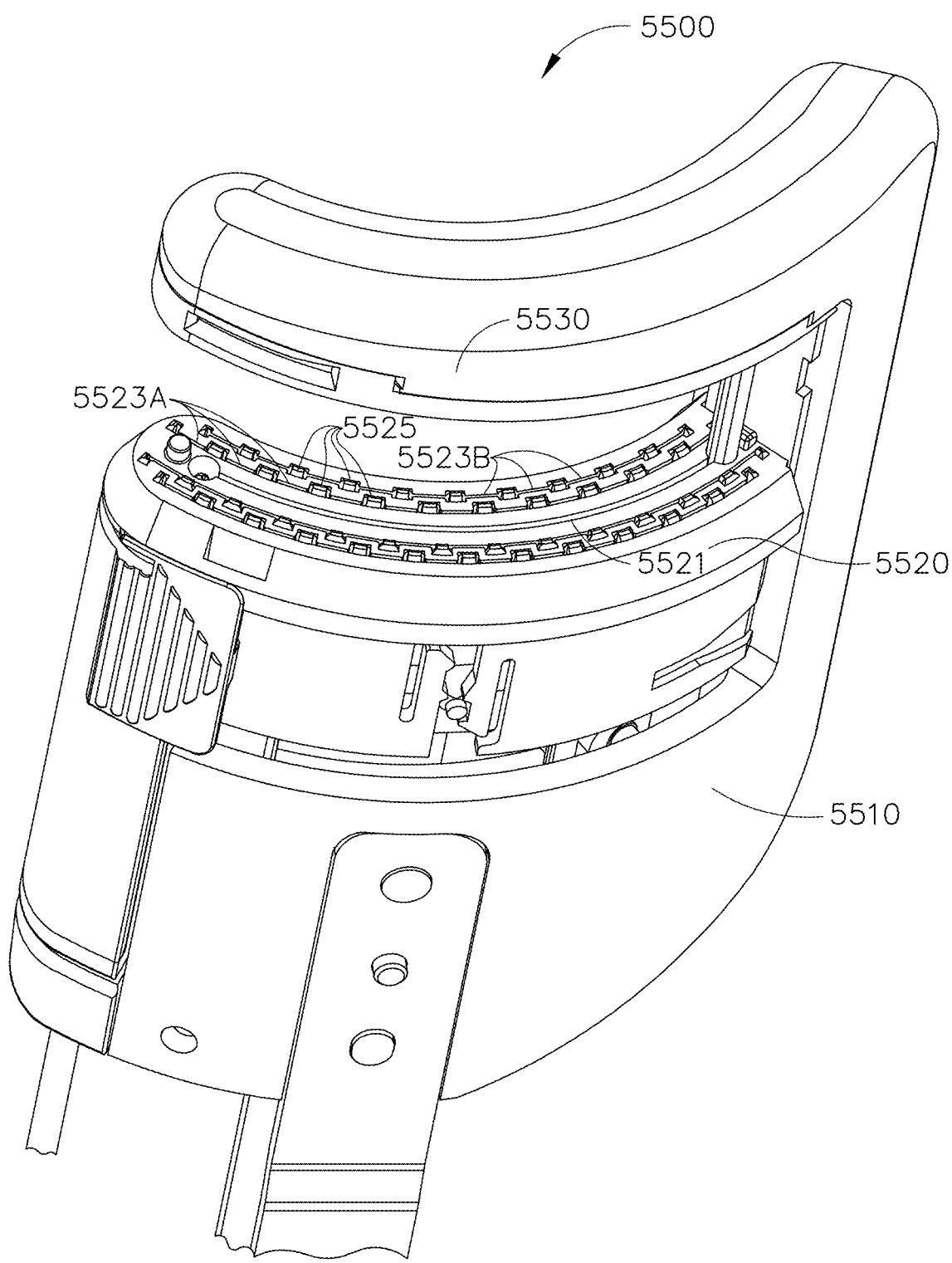
FIG. 102 is a partial perspective view of a curved stapler in accordance with at least one embodiment.
Figure 103:
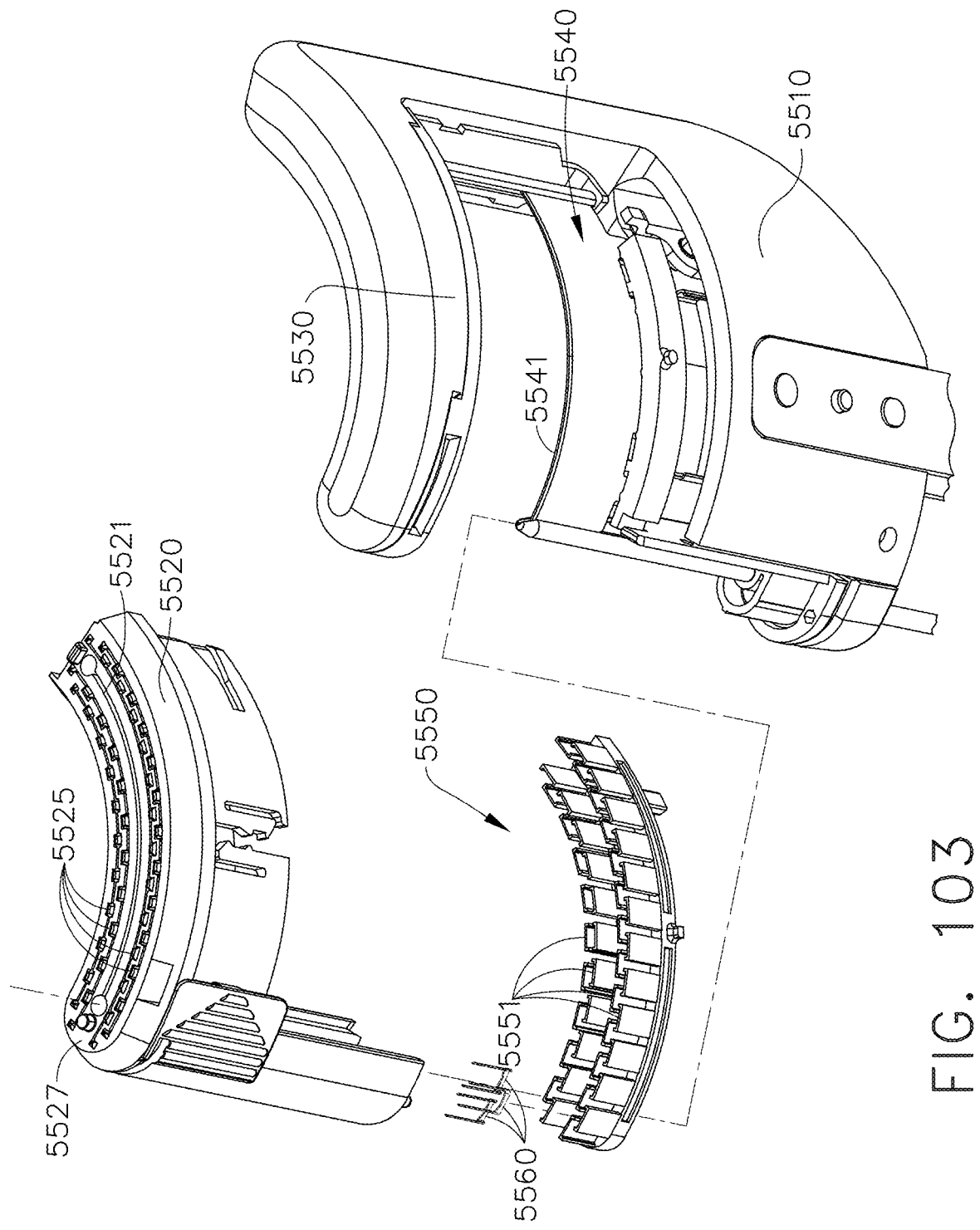
FIG. 103 is a partial exploded view of the curved stapler of FIG. 102.
Figure 104:
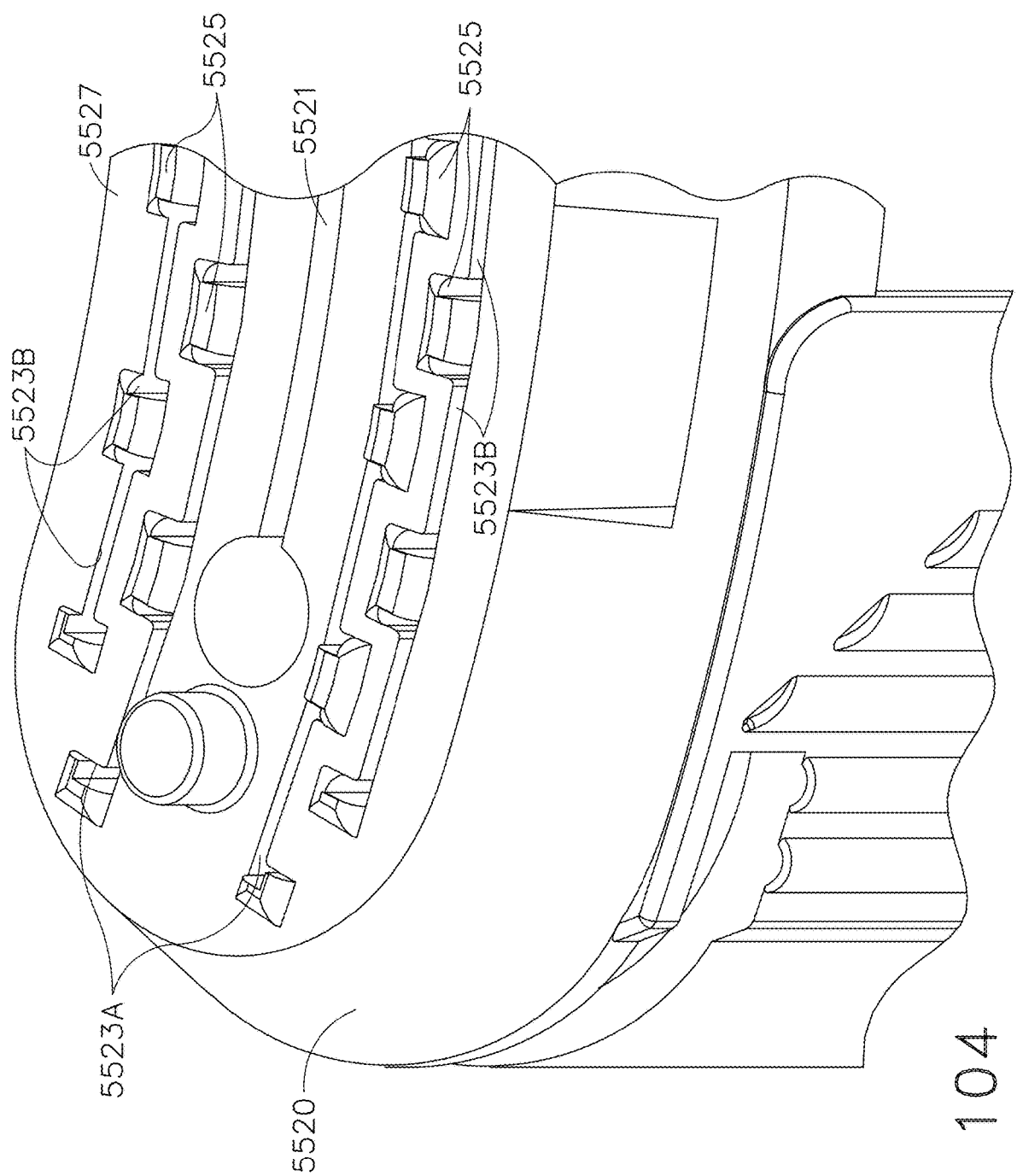
FIG. 104 is a partial perspective view of the curved stapler of FIG. 102.

FIGS. 102-104 depict a curved stapling instrument 5500 in accordance with at least one embodiment configured to capture, incise, and staple tissue. The curved stapling instrument 5500 comprises a frame assembly 5510, a staple cartridge 5520, and an anvil 5530. Upon receiving a first actuation force, the staple cartridge 5520 is driven toward the anvil 5530 to capture tissue therebetween. The curved stapling instrument 5500 further comprises a knife assembly 5540 comprising a cutting member 5541 configured to incise the tissue captured between the staple cartridge 5520 and the anvil 5530. The staple cartridge 5520 comprises a deck 5527 comprising a cutting slot 5521 configured to receive the cutting member 5541, a plurality of staple cavities 5523A and 5523B, and a plurality of staples 5560 removably stored within the staple cavities 5523A, 5523B. The curved stapling instrument 5500 further comprises a driver assembly 5550 comprising a plurality of staple drivers 5551 configured to drive the staples 5560 toward the anvil 5530 upon the application of a second actuation force. The second actuation force is responsible for lifting the driver assembly 5550 and the knife assembly 5540 vertically relative to the curved stapling instrument 5500 in order to incise and staple the tissue.

The staple cartridge 5520 further comprises a plurality of deck features 5525 extending from the deck 5527. Embodiments are envisioned where the deck features 5525 are separate portions configured to be attached to the deck 5527. The deck features 5525 can be extensions of the staple cavities 5523A, 5523B in order to support, guide, and/or control the staples 5560 while loading the staples 5560 into the cartridge 5520, while housing, or supporting, the staples 5560 before ejecting the staples 5560, and/or while ejecting the staples 5560 from the cartridge 5520. A single deck feature 5525 supports two different staple legs of neighboring staples. The deck features 5525 can comprise multiple support walls configured to support one or more sides, faces, and/or edges of each staple leg. Embodiments are envisioned where the deck features 5525 on the outer staple rows, rows furthest from the slot, only correlate with every other staple cavity in each outer row. Staple features may increase in density the closer to the incision the staple features are positioned.

Figure 105:
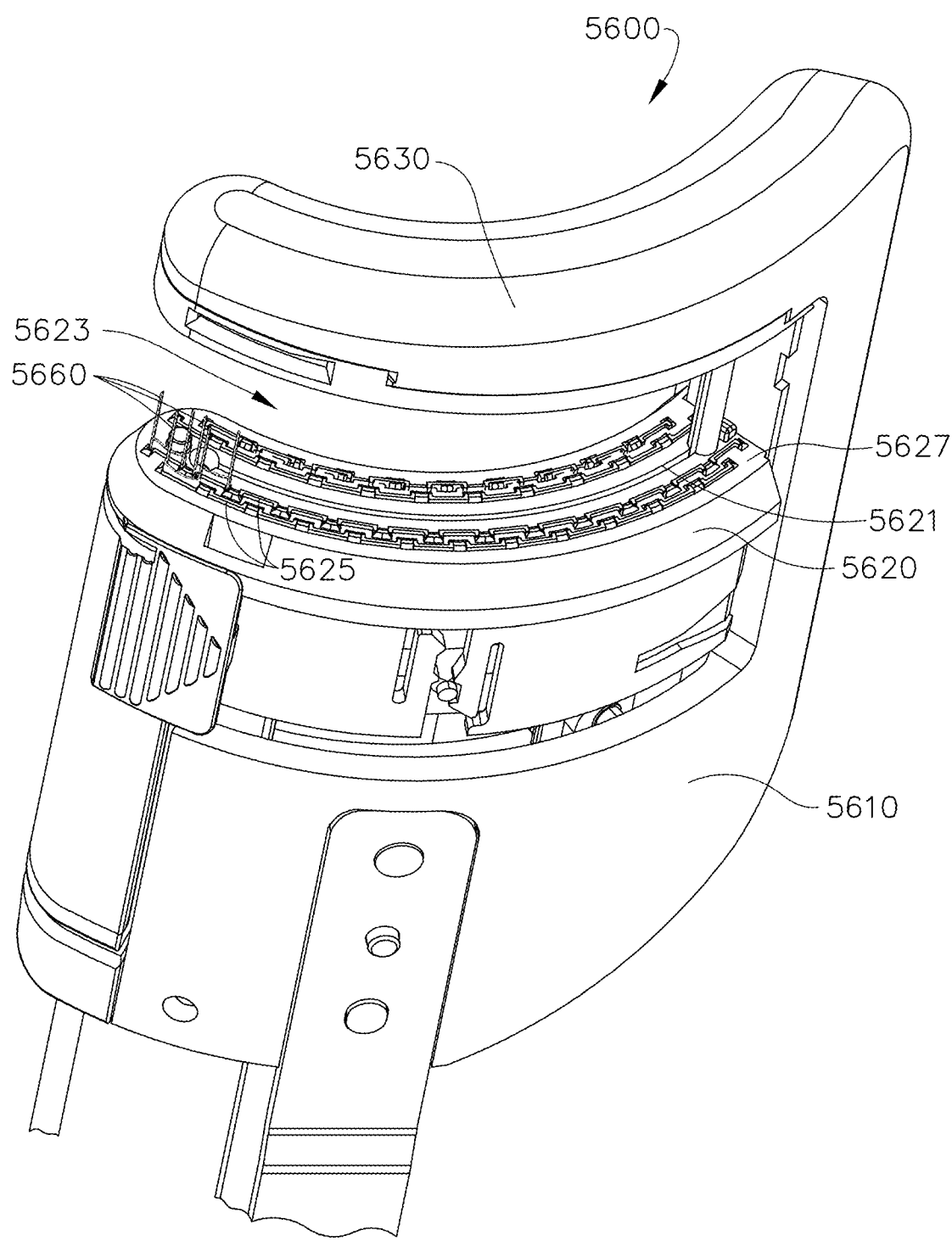
FIG. 105 is a partial perspective view of a curved stapler in accordance with at least one embodiment.
Figure 106:
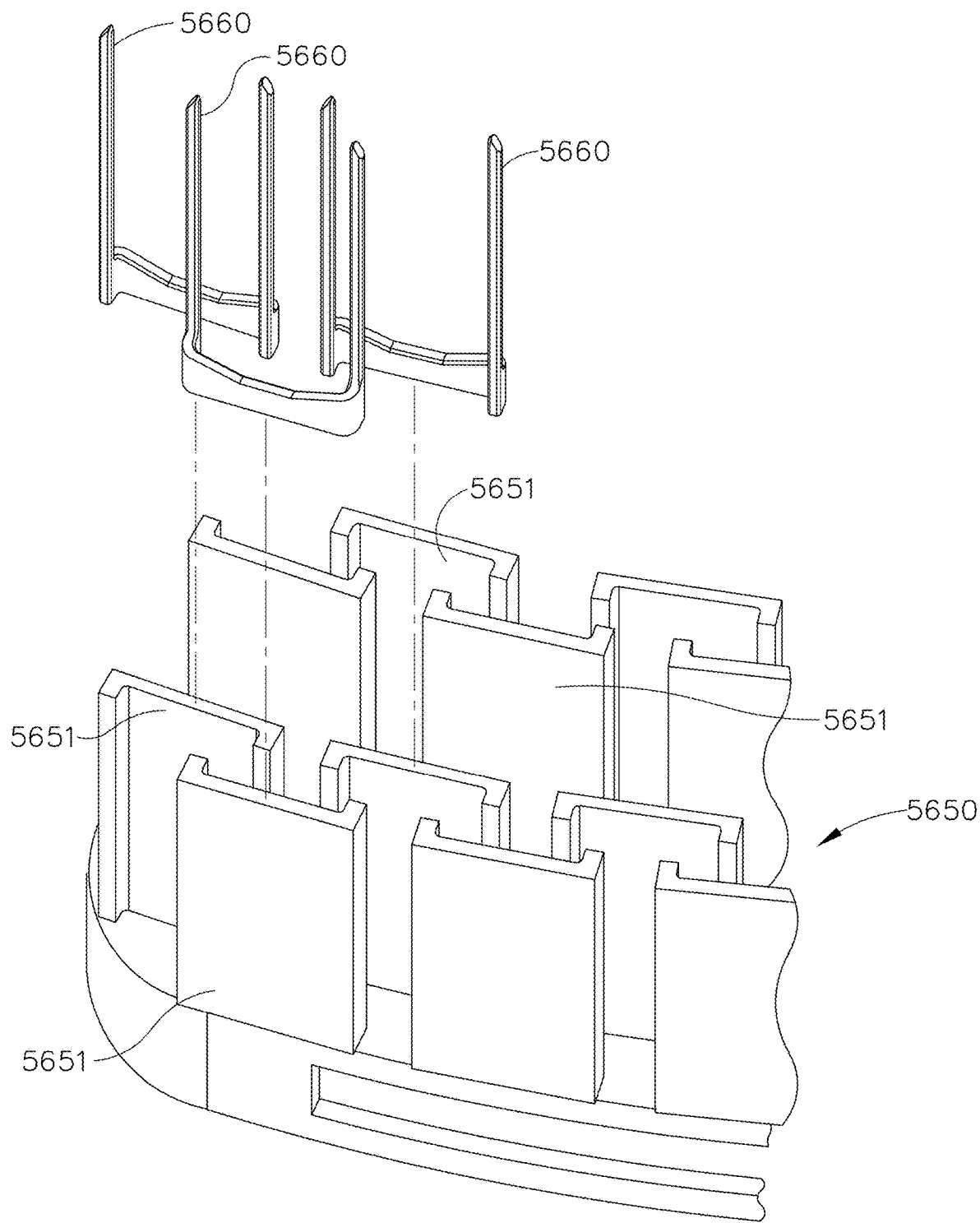
FIG. 106 is a partial perspective view of the curved stapler of FIG. 105.

FIGS. 105 and 106 depict a curved stapling instrument 5600 in accordance with at least one embodiment configured to capture, incise, and staple tissue. The curved stapling instrument 5600 comprises a frame assembly 5610, a staple cartridge 5620, and an anvil 5630. Upon receiving a first actuation force, the staple cartridge 5620 is driven toward the anvil 5630 to capture tissue therebetween. The curved stapling instrument 5600 further comprises a knife assembly comprising a cutting member configured to incise the tissue captured between the staple cartridge 5620 and the anvil 5630. The staple cartridge 5620 comprises a deck 5627 comprising a cutting slot 5621 configured to receive the cutting member, a plurality of staple cavities 5623, and a plurality of staples 5660 removably stored within the staple cavities 5623. The curved stapling instrument 5600 further comprises a driver assembly 5650 comprising a plurality of staple drivers 5651 configured to drive the staples 5660 toward the anvil 5630 upon the application of a second actuation force. The second actuation force is responsible for lifting the driver assembly 5650 and the knife assembly vertically relative to the curved stapling instrument 5600 in order to incise and staple the tissue.

The staple cartridge 5620 further comprises a plurality of deck features 5625 extending from the deck 5627. Embodiments are envisioned where the deck features 5625 are separate portions configured to be attached to the deck 5627. The deck features 5625 can be extensions of the staple cavities 5623 in order to support, guide, and/or control the staples 5660 while loading the staples 5660 into the cartridge 5620, while housing, or supporting, the staples 5660 before ejecting the staples 5660, and/or while ejecting the staples 5660 from the cartridge 5620. The deck features 5625 can comprise multiple support walls configured to support one or more sides, faces, and/or edges of each staple leg. The deck features 5625 extend from at least one of the staple leg walls and at least one of the staple base walls of the staple cavities.

The staple drivers 5651 comprise a flat profile which is at least substantially the same as the bottom profile of the staples 5660. Having similar, or the same, profiles permits an adequate force distribution by the staple drivers 5651 over the staple base portions of the staples 5660. When being formed against the anvil 5630, the similar profiles between the drivers 5651 and the staples 5660 prevents the staples 5660 becoming misaligned.

The entire disclosures of:
U.S. Pat. No. 5,403,312, entitled ELECTROSURGICAL HEMOSTATIC DEVICE, which issued on Apr. 4, 1995;
U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
U.S. Pat. No. 7,670,334, entitled SURGICAL INSTRUMENT HAVING AN ARTICULATING END EFFECTOR, which issued on Mar. 2, 2010;
U.S. Pat. No. 7,753,245, entitled SURGICAL STAPLING INSTRUMENTS, which issued on Jul. 13, 2010;
U.S. Pat. No. 8,393,514, entitled SELECTIVELY ORIENTABLE IMPLANTABLE FASTENER CARTRIDGE, which issued on Mar. 12, 2013;
U.S. patent application Ser. No. 11/343,803, entitled SURGICAL INSTRUMENT HAVING RECORDING CAPABILITIES, now U.S. Pat. No. 7,845,537;
U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, plasma peroxide, or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical staple, comprising:
   (a) a bioabsorbable frame including a crown and a pair of legs integrally connected with the crown; and
   (b) a bioabsorbable coating disposed on the bioabsorbable frame such that a first portion of each leg includes the bioabsorbable coating and a second portion of each leg omits the bioabsorbable coating, wherein the bioabsorbable coating is configured to delay bioabsorption of the bioabsorbable frame when the surgical staple is implanted in tissue.

2. The surgical staple of claim 1, wherein each of the legs terminates at a tip, wherein the bioabsorbable coating is absent on the tips and is present on a remainder of the bioabsorbable frame.

3. The surgical staple of claim 1, wherein the bioabsorbable coating comprises a bioabsorbable polymer.

4. The surgical staple of claim 3, wherein the bioabsorbable polymer comprises at least one of polylactic acid (PLA) or polyglycolic acid (PGA).

5. The surgical staple of claim 1, further comprising an anti-microbial material.

6. The surgical staple of claim 5, wherein the anti-microbial material comprises triclosan.

7. The surgical staple of claim 1, wherein the bioabsorbable frame comprises a magnesium alloy.

8. A surgical staple assembly, comprising:
(a) the surgical staple of claim 1, wherein each of the legs terminates at a tip; and
(b) an adjunct through which the legs of the staple are configured to extend when the staple is applied to tissue, wherein the adjunct is configured to reside between the crown and the tips of the staple when the legs are formed in the tissue.

9. The surgical staple assembly of claim 8, wherein the adjunct is at least one of resilient or bioabsorbable.

10. The surgical staple assembly of claim 8, further comprising an anti-microbial coating disposed on at least one of the adjunct or the surgical staple.

11. A surgical staple cartridge, comprising:
(a) a cartridge body including a deck and a plurality of staple cavities defined in the deck; and
(b) a plurality of staples disposed in the staple cavities, wherein the plurality of staples includes the surgical staple of claim 1.

12. The surgical staple cartridge of claim 11, in combination with an adjunct, wherein the legs of the surgical staple are configured to extend through the adjunct when the surgical staple is applied to tissue, wherein the adjunct is configured to reside between the crown and the tips of the surgical staple when the legs of the surgical staple are formed in the tissue.

13. A surgical staple, comprising:
(a) a crown;
(b) a pair of legs integrally connected with and extending away from the crown, wherein the crown and the legs are bioabsorbable; and
(c) a bioabsorbable coating disposed on the legs such that a first portion of each leg includes the bioabsorbable coating and a second portion of each leg omits the bioabsorbable coating, wherein the bioabsorbable coating is configured to delay bioabsorption of the legs when the surgical staple is implanted in tissue.

14. The surgical staple of claim 13, wherein the crown and the legs define a bioabsorbable frame that comprises a magnesium alloy.

15. The surgical staple of claim 13, wherein each of the legs terminates at a tip, wherein the bioabsorbable coating is omitted from the tips.

16. The surgical staple of claim 13, wherein the bioabsorbable coating comprises at least one of polylactic acid (PLA) or polyglycolic acid (PGA).

17. The surgical staple of claim 13, further comprising an anti-microbial coating.

18. A surgical staple assembly, comprising:
(a) a staple including:
(i) a crown,
(ii) a pair of legs integrally connected with the crown, wherein each of the legs terminates at a tip, and
(iii) a bioabsorbable coating disposed on the legs such that a first portion of each leg includes the bioabsorbable coating and a second portion of each leg omits the bioabsorbable coating; and
(b) an adjunct through which the legs of the staple are configured to extend when the staple is applied to tissue, wherein the adjunct is configured to reside between the crown and the tips of the staple when the legs are formed in the tissue.

19. The surgical staple assembly of claim 18, wherein the crown and the legs define a bioabsorbable frame of the staple, wherein the bioabsorbable coating is configured to delay bioabsorption of the bioabsorbable frame when the staple is implanted in tissue.

20. The surgical staple assembly of claim 19, wherein the bioabsorbable frame comprises a magnesium alloy, wherein the bioabsorbable coating comprises at least one of polylactic acid (PLA) or polyglycolic acid (PGA).

* * * * *